United States Patent
Kramer et al.

(10) Patent No.: US 6,428,490 B1
(45) Date of Patent: Aug. 6, 2002

(54) GONIOMETER-BASED BODY-TRACKING DEVICE AND METHOD

(75) Inventors: James F. Kramer, Menlo Park; John M. Ananny, San Francisco; Loren F. Bentley, Palo Alto; Paul L. Korff, Sunnyvale; Allen R. Boronkay, San Jose; Conor McNamara, San Francisco, all of CA (US)

(73) Assignee: Virtual Technologies, Inc., San Jose, CA (US)

( * ) Notice: Subject to any disclaimer, the term of this patent is extended or adjusted under 35 U.S.C. 154(b) by 0 days.

(21) Appl. No.: 09/503,104

(22) Filed: Feb. 11, 2000

Related U.S. Application Data

(63) Continuation of application No. 09/064,637, filed on Apr. 12, 1998, now Pat. No. 6,050,962
(60) Provisional application No. 60/044,495, filed on Apr. 21, 1997, and provisional application No. 60/054,745, filed on Aug. 4, 1997.

(51) Int. Cl.[7] .............................................. A61B 5/00
(52) U.S. Cl. .................................................... 600/595
(58) Field of Search .............................. 600/587, 595, 600/594

(56) References Cited

U.S. PATENT DOCUMENTS 3,919,691 A 11/1975 Noll
3,923,166 A 12/1975 Fletcher et al.

(List continued on next page.)

OTHER PUBLICATIONS

"Animation: The New 'Full Body' Motion Capture–Digital Acting/Virtual Reality—Suit" Analogus Corporation, Fremont, California (author and date unknown).

Erdman, et al., "Kinematic and Kinetic Analysis of the Human Wrist by Stereoscopic Instrumentation" Transactions of the ASME, vol. 101, pp. 124–133, May 1979.

(List continued on next page.)

*Primary Examiner*—Max Hindenburg
(74) *Attorney, Agent, or Firm*—Paul M. Thyfault; James Riegel

(57) ABSTRACT

A sensing system is provided for measuring various joints of a human body for applications for performance animation, biomechanical studies and general motion capture. One sensing device of the system is a linkage-based sensing structure comprising rigid links interconnected by revolute joints, where each joint angle is measured by a resistive bend sensor or other convenient goniometer. Such a linkage-based sensing structure is typically used for measuring joints of the body, such as the shoulders, hips, neck, back and forearm, which have more than a single rotary degree of freedom of movement. In one embodiment of the linkage-based sensing structure, a single long resistive bend sensor measures the angle of more that one revolute joint. The terminal ends of the linkage-based sensing structure are secured to the body such that movement of the joint is measured by the device. A second sensing device of the sensing system comprises a flat, flexible resistive bend sensor guided by a channel on an elastic garment. Such a flat sensing device is typically used to measure various other joints of the body which have primarily one degree of freedom of movement, such as the elbows, knees and ankles. Combining the two sensing devices as described, the sensing system has low sensor bulk at body extremities, yet accurately measures the multi-degree-of-freedom joints nearer the torso. Such a system can operate totally untethered, in real time, and without concern for electromagnetic interference or sensor occlusion.

23 Claims, 57 Drawing Sheets

U.S. PATENT DOCUMENTS

| Patent No. | | Date | Inventor | Ref |
|---|---|---|---|---|
| 4,046,262 A | | 9/1977 | Vykukal et al. | |
| 4,108,164 A | | 8/1978 | Hall, Sr. | |
| 4,302,138 A | | 11/1981 | Zarudiansky | |
| 4,414,537 A | | 11/1983 | Grimes | |
| 4,414,984 A | | 11/1983 | Zarudinasky | |
| 4,444,205 A | * | 4/1984 | Jackson | 600/595 |
| 4,461,085 A | | 7/1984 | Dewar et al. | |
| 4,542,291 A | | 9/1985 | Zimmerman | |
| 4,557,275 A | | 12/1985 | Dempsey, Jr. | |
| 4,575,297 A | | 3/1986 | Richter | |
| 4,584,625 A | | 4/1986 | Kellogg | |
| 4,664,130 A | | 5/1987 | Gracovetsky | |
| 4,676,002 A | | 6/1987 | Slocum | |
| 4,715,235 A | * | 12/1987 | Fukui et al. | 600/595 |
| 4,757,453 A | | 7/1988 | Nasiff | 364/415 |
| 4,853,874 A | | 8/1989 | Iwamoto et al. | |
| 4,874,998 A | | 10/1989 | Hollis, Jr. | |
| 4,937,444 A | | 6/1990 | Zimmerman | |
| 4,986,280 A | | 1/1991 | Marcus et al. | |
| 4,988,981 A | | 1/1991 | Zimmerman et al. | |
| 5,004,391 A | | 4/1991 | Burdea | |
| 5,038,137 A | | 8/1991 | Lloyd | |
| 5,047,952 A | | 9/1991 | Kramer et al. | 364/513.5 |
| 5,086,785 A | * | 2/1992 | Gentile et al. | 600/595 |
| 5,121,747 A | | 6/1992 | Andrews | |
| 5,143,505 A | | 9/1992 | Burdea et al. | |
| 5,166,463 A | | 11/1992 | Weber | |
| 5,184,009 A | | 2/1993 | Wright et al. | |
| 5,184,319 A | | 2/1993 | Kramer | |
| 5,185,561 A | | 2/1993 | Good et al. | |
| 5,186,629 A | | 2/1993 | Rohen | |
| 5,193,963 A | | 3/1993 | McAffee et al. | |
| 5,203,563 A | | 4/1993 | Loper, III | |
| 5,280,265 A | | 1/1994 | Kramer et al. | 338/210 |
| 5,289,827 A | * | 3/1994 | Orkin et al. | 600/595 |
| 5,296,871 A | | 3/1994 | Paley | |
| 5,316,017 A | | 5/1994 | Edwards et al. | 128/782 |
| 5,354,162 A | | 10/1994 | Burdea et al. | |
| 5,442,729 A | * | 8/1995 | Kramer et al. | 600/595 |
| 5,451,924 A | | 9/1995 | Massimino et al. | |
| 5,562,707 A | | 10/1996 | Prochazka et al. | |
| 5,587,937 A | | 12/1996 | Massie et al. | |
| 5,592,401 A | | 1/1997 | Kramer | |
| 5,631,861 A | | 5/1997 | Kramer | |
| 5,676,157 A | | 10/1997 | Kramer | 128/782 |
| 5,813,406 A | | 9/1998 | Kramer et al. | |

OTHER PUBLICATIONS

Fisher, "Telepresence master glove controller for dexterous robotic end–effectors" SPIE vol. 726 Intelligent Robots and Computer Vision: Fifth in a Series (1986).

Foley, "Interfaces for Advanced Computing" Scientific American, No. 4, pp. 83–90, Oct. 1987.

Jespersen et al., "Joint Angle Position Sensor" $40^{th}$ ACEMB, Niagra Falls, NY, p. 104, Sep. 1987.

Bergamasco et al., "Advanced Interfaces for Teleoperated Biomedical Robots" IEEE Engineering in Medicine & Biology Society $11^{th}$ Annual International Conference, pp. 12–13, 1989.

Eddy, "Power Glove Get A Grip On Your Games" VideoGames & Computer Entertainment, pp. 19–20, 1989.

Wright, "Altered States– A software developer's vision of the future of virtual reality" Computer Graphics World, pp. 77–83, Dec. 1989.

Orr, "Exotic CAD– Given what's happening in R&D, tomorrow's CAD system may be something you wear" Computer Graphics World, pp. 88–92, Jul. 1989.

Gardner, "The Power Glove" Design News, pp. 63–68, Dec. 1989.

Weiss, "A Gallium Arsenide Strain–Optic Voltage Monitor" Sensors, pp. 37–40, Oct. 1995.

* cited by examiner

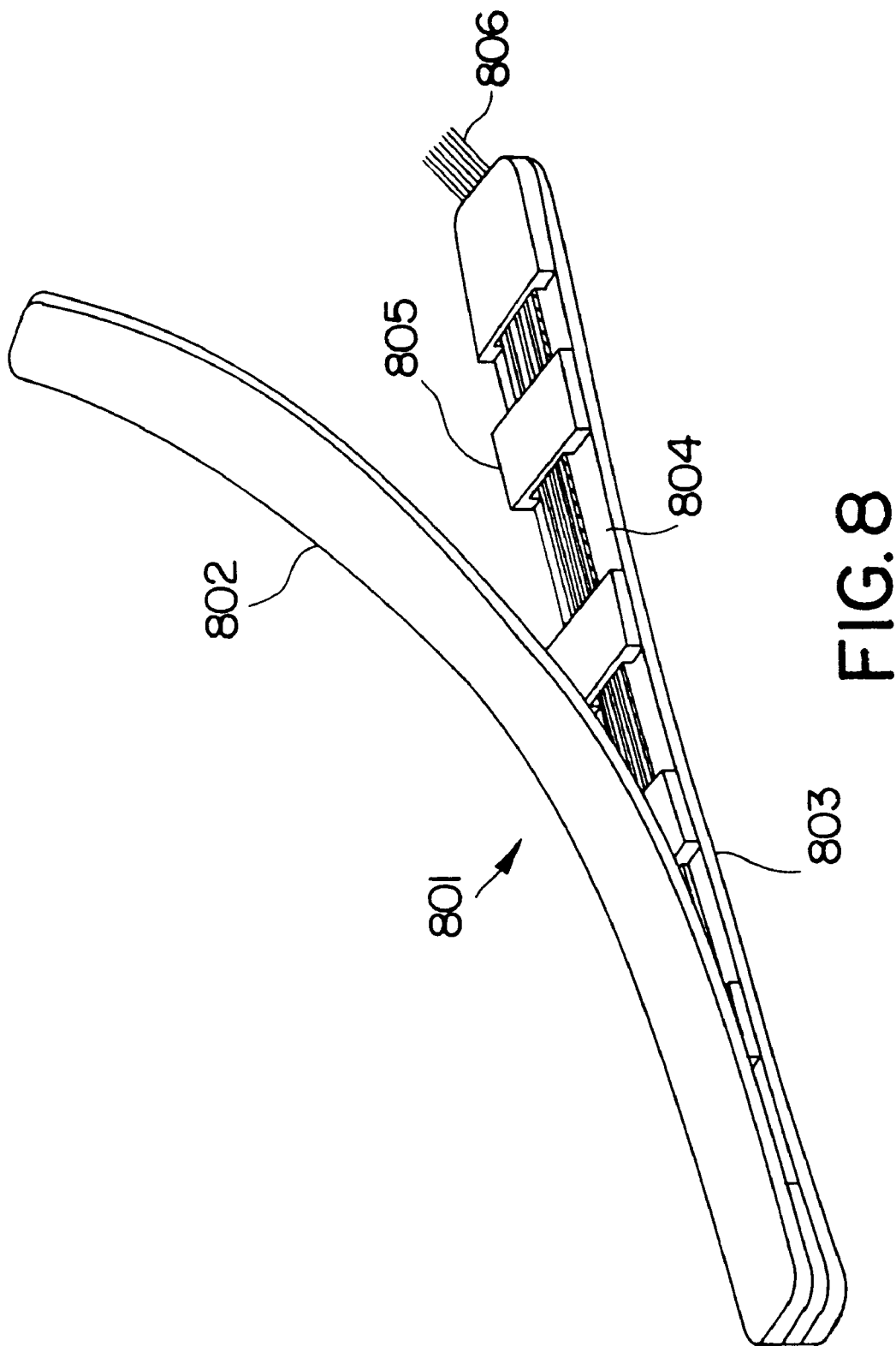

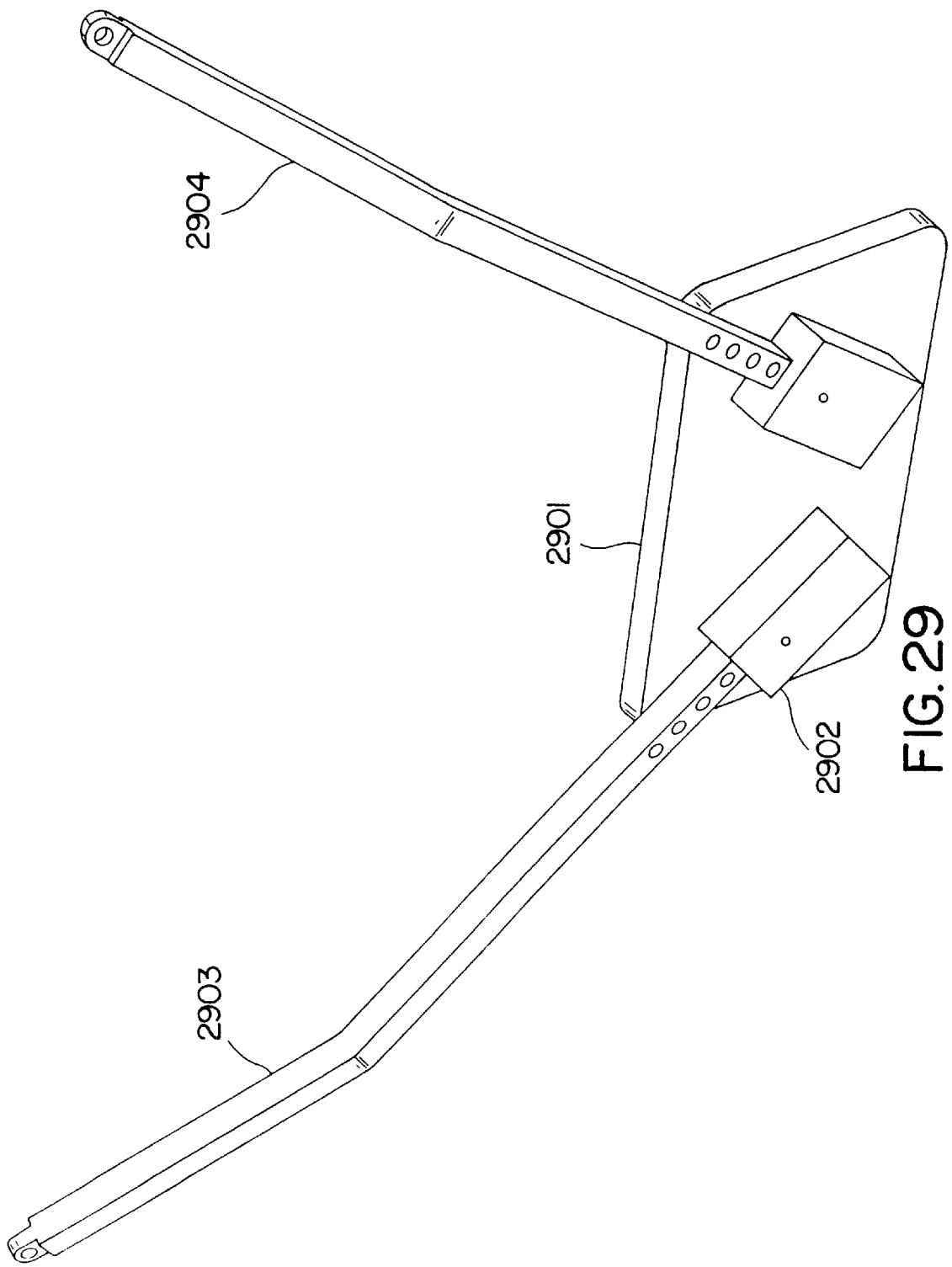

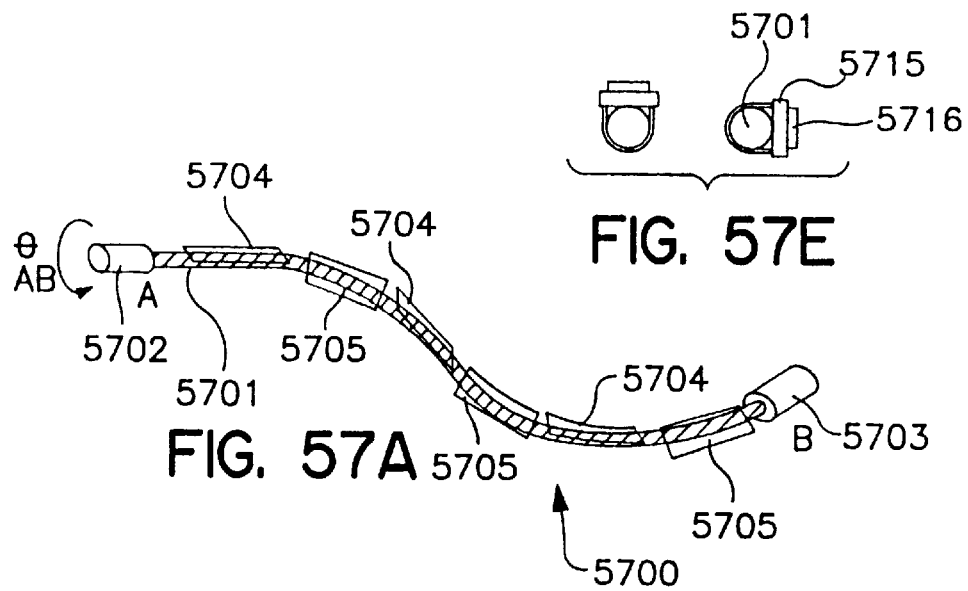
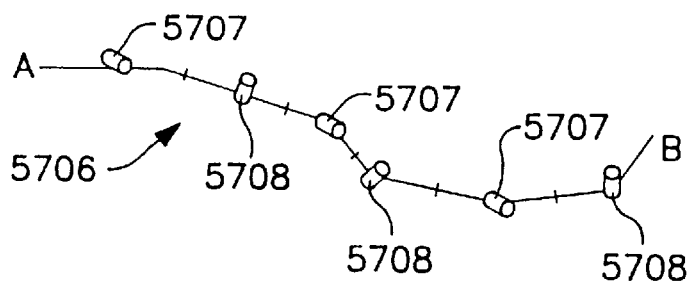
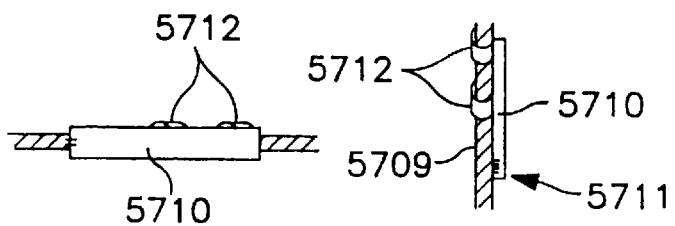
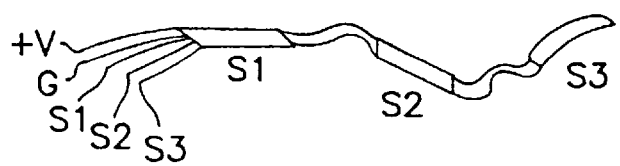

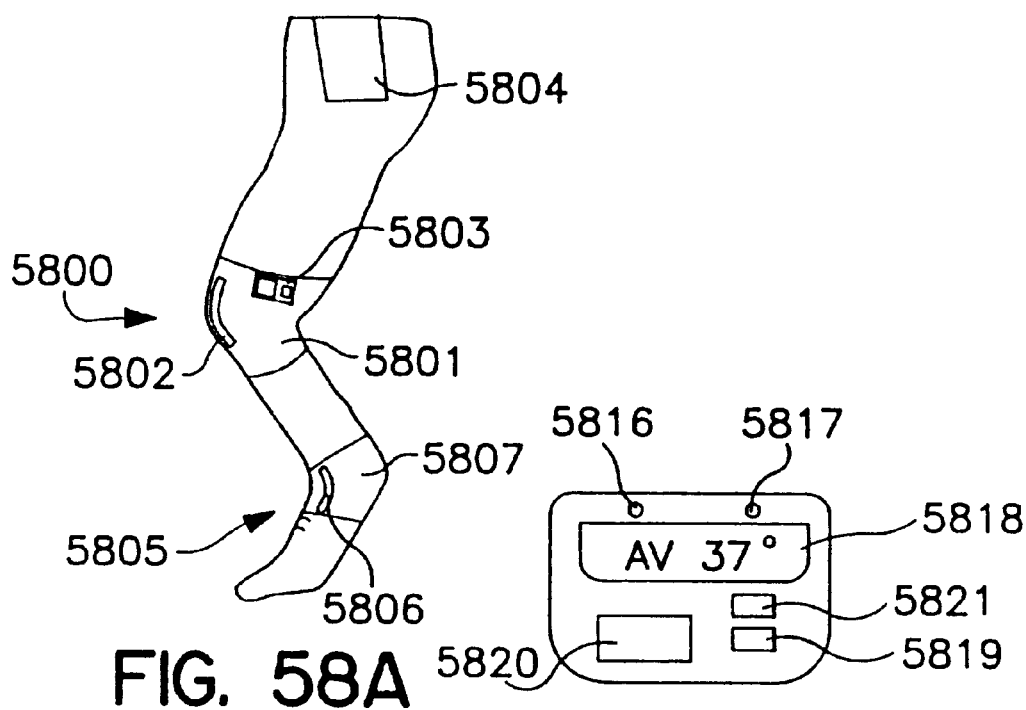
FIG. 58A
FIG. 58D
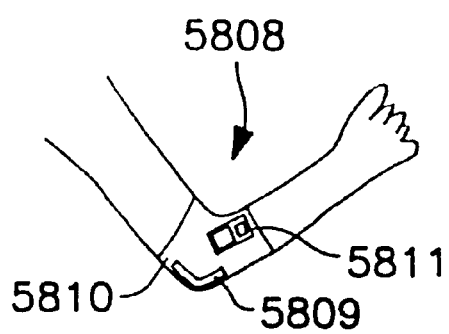
FIG. 58B
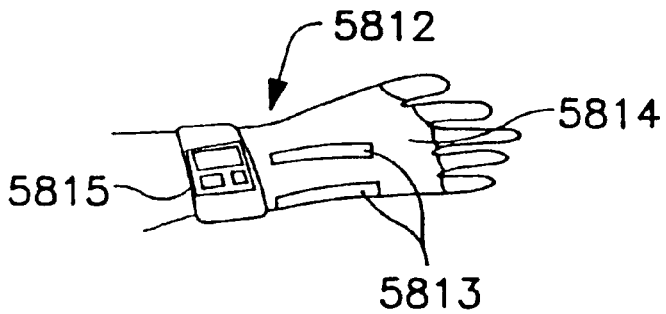
FIG. 58C

GONIOMETER-BASED BODY-TRACKING DEVICE AND METHOD

This is a continuation of application Ser. No. 09/064,637 filed Apr. 12, 1998 now U.S. Pat. No. 6,050,962.

CROSS-REFERENCE TO RELATED APPLICATIONS

This application is a continuation-in-part of U.S. Provisional Application Serial No. 60/044,495, filed Apr. 21, 1997, and No. 60/054,745, filed Aug. 4, 1997.

INTRODUCTION

1. Background

A growing market has developed for tools and systems that track humans and other bodies at rest and in motion. The applications for such systems vary considerably, and include such areas as the creation of computer-generated and graphical animations, the analysis of human-computer interaction, the assessment of performance athletics and other biomechanics activities, and the evaluation of workplace and other activities for general ergonomical fitness.

The possible sample uses for a body-tracking system are wide and varied. For example, a user interested in creating a realistic computer animation of a gymnast might be interested in tracking the full-body movements of the gymnast during a brief tumbling run characterized by high-velocity, high-acceleration activity. A second sample user might instead be interested in measuring the upper-body movements of a typical clerical worker over a full workday, in order to assess the role of various activities in causing repetitive stress injury. A third sample user might wish to record the motions of a high-performance skier or snowboarder over a mile-long section of mountain in order to study and possibly improve his or her technique.

The most general functional requirement of a body-tracking (or motion-capture) device is that it accurately and reliably measure and report the configuration of the various articulating members (limbs) of the body over a particular duration of interest. In order to be most useful, however, a motion-capture device must also satisfy additional criteria. It must be sufficiently lightweight and unencumbering to allow the free performance of the activity being measured. (A system that prevents an athlete or performer from acting naturally, either due to the addition of weight, to an impeding of balance and flexibility, or to the presence of other physical constraints is clearly of lessened utility as a motion-capture device). It must also allow for a performance space appropriate to the motion being measured, i.e., it must allow the user the freedom to move through space as needed to complete the activity being measured.

Various contributions to the prior art have addressed themselves to the general problem of motion capture. Electromagnetic (E/M) tracking systems, such as those manufactured by Polhemus and Ascension, use multiple elements consisting of three orthogonally wound coils. At least one such element is designated as a transmitter, and at least one such element is designated as a receiver. By energizing, in turn, the coils in a transmitter element, and measuring the signal induced in the receiver elements(s), the relative position of the transmitter and receiver element(s) can be calculated. Such E/M tracking systems are sensitive to the presence of metal in the close surroundings and, in addition, have a workspace limited by the requirement that the receiver(s) remain within several feet of their corresponding transmitter. Another disadvantage of E/M technology is that it typically includes lag time which renders the position data non-real time.

As with E/M position sensing technology, ultrasonic (US) and infrared (IR) position sensing technologies do not require a direct tether between the hand and monitor. US and IR technologies have the disadvantage, however, that they both require direct line of sight. Thus, when one hand passes in front of the other, the position signal can be lost. Additionally, US technology, in particular, is very sensitive to ambient acoustic noise. Both technologies can introduce lag time, again rendering the position data non-real time.

Another example of a prior art solution to the problem of motion capture is a passive, optically-based body-tracking system, such as that produced by Motion Analysis. In such a system, multiple reflective markers are attached to the surface of the limbs of interest, such that these markers are placed on either side of the articulating joints. Multiple cameras record the positions of these markers over time, and this marker position data is used to extract (via "inverse kinematics") the corresponding configurations of the various limbs and joints of interest. Such optical tracking systems have an inherent workspace limitation that comes from the need to use cameras, namely that the user of the system is limited to the relatively small workspace that is both visible to the cameras and in focus. Tracking problems occur when markers become occluded, since data cannot be recorded. In addition, such a system requires a non-trivial amount of post-processing of the data; while it is expected that computing power and cost efficiency will continue to increase, optical systems still do not deliver on-the-spot, "real-time" data.

Still another example of a prior art solution is an active, optically-based body-tracking system. Such a system is conceptually similar to the passive system described above, but with several differences. The markers in such a system typically actively emit light, instead of being simple, passive reflectors. This allows the controlling software to energize each of the markers in turn, and if properly synchronized with the computer doing the data analysis, can help prevent problems that occur when the control software loses track of "which marker is which." Otherwise, the workspace, marker-occlusion, and post-processing shortcomings of such active optical systems are similar to that of the passive ones.

A Toronto-based company, Vivid Group, uses camera-based technology called Mandela to monitor human motion without requiring the user to wear any special devices. The system, however, only tracks body movements in two dimensions (2D). Most motion capture (MC) systems require the user to wear some form of element that either is a sensor itself, or is one component of a sensing system where other components are located off the user.

Still another example of a prior art solution is a theoretical simulation of the desired motion. By building a kinematic model of a human, attributing that model with realistic masses, rotational interias and other properties, and specifying all relevant initial-condition and boundary constraints, it is theoretically possible to solve the dynamic equations of motion for a complex body. Once a solution has been generated, such information could be used to create graphical animations or other imagery. There are several drawbacks, however. For example, such algorithmic solutions to motion capture are just now in their infancy and can be applied only in the most limited and constrained of activities. Also for example, the human brain is very good at detecting "incorrect" motion, so the performance demands on such a theoretical simulation will be very exacting. Also for examples such a system does not help at all with the problem of measuring the motion of living humans and is of little utility in biomechanics and ergonomic applications.

There still remains a need for a position-sensing device which is accurate, insensitive to environmental influences, has little lag time and has high data rates.

2. Relevant Literature

U.S. Pat. No. 5,676,157, "Determination of Kinematically Constrained Multi-Articulated Structures", J. F. Kramer, describes kinematically constrained multi-articulated structures.

SUMMARY OF THE INVENTION

A general overview of the inventive structure and method is now provided. The subject invention provides improvements, enhancements, and additional patentable subject matter to the prior provisional patent application numbers U.S. Patent Application Serial No. 60/044,495, filed Apr. 21, 1997, and No. 60/054,745, filed Aug. 4, 1997, which provisional applications are incorporated herein in their entireties. In particular, the subject invention provides new shoulder- and hip-sensing structures and techniques. In particular for each shoulder sensor assembly, this new structure and technique employs five long, thin, flexible strain-sensing goniometers to measure the overall angle of one or more contiguous parallel-axis revolute joint sets. The shoulder-sensing assembly is able to measure the angle of the humerus relative to a fixed point on the back. A hip-sensing assembly similar in construction to the shoulder sensor is able to measure the angle of the femur relative to a fixed point on the pelvis. Multiple parallel-axis joints provide extensibility, such as a prismatic joint function, in addition to providing the overall angle between the distal links of the two most extreme joints. In contrast, typical prismatic joints comprised of one cylinder sliding inside another often exhibit sliding friction and frequently bind if the forces between the cylinders are off axis. By building a "prismatic joint" from revolute joints, binding can be eliminated and resistance to movement greatly reduced.

As provided in this and the afore described provisional patent applications, a very thin linkage with small diameter joints may be fabricated, where flat, flexible bend sensors are used to measure the arc subtended by the distal links. To hold the bend sensors against the linkage structure, special guides may be used. These guides provide a channel in which each sensor slides against its associated linkage as a structural joint is rotated. The guides also limit the range of motion of the neighboring joints. One or more guides may be fastened to a link. The guides for adjacent links are typically designed to come into contact at a pre-determined joint angle, thus limiting joint range by preventing the joint from bending further. The guides may be fastened to the intended link in any convenient manner. In particular, the guides may have clips which allow them to snap around the intended link.

By way of overview, the Virtual Technologies' goniometer-based body-tracking device, equivalently referred to as the Range-Of-Motion Suit (ROMS) or the CyberSuit®, uses a bend-sensing technology to measure five degrees of freedom of the leg and foot, and six degrees of freedom of the arm and wrist. The degrees of freedom (DOF) measured by one embodiment of the present structure includes: ankle flexion, knee flexion, hip abduction, hip flexion, hip rotation, wrist flexion, wrist abduction, elbow flexion, shoulder flexion, shoulder abduction, and shoulder rotation. The present design directly extends to measurement of flexion, abduction and rotation of the lumbar and thoracic regions of the back, in addition to the neck. Means are also provided for measuring forearm rotation.

The CyberSuit measurement system includes a Lower Extremity Assembly (LEA), an Upper Extremity Assembly (UEA), a Waist Pack Assembly (WPA), and VirtualBody® graphical body-simulation software. The LEA and UEA are Lycra®-based garments with pockets and fixtures for removable sensor assemblies. The WPA is a belt-mounted pack that contains all the instrumentation electronics for data collection and logging. VirtualBody software contains utilities for user calibration, graphical body model, and real-time data acquisition via the WPA. A hand-held controller with LCD and six buttons serves as an optional user interface.

An overview of the CyberSuit is now described. The patented Virtual Technologies, Inc. (Palo Alto, Calif.) resistive bend sensor (goniometer) (Kramer, et al, U.S. Pat. Nos. 5,047,952 and 5,280,265, which are hereby incorporated by reference) is the basis of the angle-sensing technology used in the CyberSuit. Sensors similar to those used in the Virtual Technologies CyberGlove product have been incorporated into innovative multisensor assemblies to accommodate the larger joints of the knee, ankle, elbow and wrist, and the complex ball and socket joints of the shoulder and hip. Mechanically, the sensors are thin strips approximately 0.01" thick, 0.20" wide (minor axis), and variable length (major axis). The sensor measures the angle between the tangents at its endpoints when the sensor assembly experiences pure bending about the minor axis. The CyberSuit incorporates assemblies which use these sensors to accurately measure 1, 2 or 3 degrees of freedom, as appropriate, at each joint. Both the LEA and the UEA incorporate two types of sensor assemblies, a 1-DOF assembly used on the ankle, knee, and elbow, and a 3-DOF assembly used on the hip and shoulder. The UEA also includes a 2-DOF sensor assembly, used on the wrist.

The CyberSuit incorporates the sensors in a Lycra suit with an embedded wiring harness, sensor pockets, connector pockets, and base plates. The sensor pockets hold flat sensors used in 1-DOF and 2-DOF assemblies, which measure angles directly on the body. The base plates serve as fixation points for mechanical assemblies consisting of multiple, light, rigid links. The sensors are attached to the linkages in such a way that they measure three degrees of freedom between relevant major bones while bypassing intermediary body segments.

The inventive structure and method incorporate numerous design details and innovative elements, some of which are summarized below. Other inventive structures, methods, and elements are described in the detailed description.

One innovative element, the 3-DOF assemblies, include the above-mentioned mechanical linkages, with attached sensors, and the base plate, fabric, and strap configuration which secures the linkage to the body segments between which the relative orientation is being measured. The linkage assemblies typically consist of at least three segments, each of which contains many individual links but bends only in one plane. This compound planar series of linkages measures the angle between linkage endpoints while permitting some translation of one end-link with respect to the other. Using several of these linkage segments achieves X-Y-Z translation and full range of motion for a body joint. The linkage endpoints mirror the orientation of one bone with respect to another so the sensors effectively measure the particular bone-to-bone angular orientation. The base plates are held to the suit in fabric pockets including straps which can be adjusted for each user in such a way as to maintain a known fixed orientation between the linkage endpoint and the bones being measured. This linkage design and application allows for user-independent calibration of the linkage assemblies themselves. Due to the details of the linkage and joint geometries, the design employs a method of attaching the sensors to the linkages which captures and protects the sensor, maintains a fixed tangency with the linkage endpoints, and accommodates length changes which occur throughout the full joint range of motion. The use of multi-link planar segments allows significant translation without orientation change, which permits measurement over a full range of motion for a wide range of users. The link lengths are adjustable for different users of more variant body types.

Another innovative element are the 2-DOF assemblies. The sensor configuration used on the wrist is designed to handle the special case of a joint in which two degrees of freedom are measured and there is a limited range of motion. This design includes fan-shaped pockets and corresponding tabbed bend sensor guides which physically decouple the two degrees of freedom being measured and allow each one to be accurately measured with a single linear 1-DOF sensor.

The 1-DOF assemblies include 1-DOF joints which are directly measured with a sensor assembly encased in a flat fabric pocket sewn to the Lycra material of the suit. The assembly consists of three layers: bottom and top guide layers of smooth plastic and a middle sensor layer. The guides are designed to protect and enclose the sensor while allowing free sliding within the pocket and relative sliding between the sections to prevent buckling. The guide and pocket are also designed to maintain sensor endpoint tangency with the body part being measured. The design also allows the sensors to be used by users with different limb lengths and joint geometries and to accommodate these variations without adjustment. The sensor layer can consist of one long sensor or multiple sensors of various lengths which are electrically cascaded in series. These guides include devices to maintain endpoint tangency between consecutive segments while allowing sliding.

BRIEF DESCRIPTION OF THE DRAWINGS

FIG. 8 is a diagrammatic illustration showing an exemplary 1-DOF sensor assembly.

FIG. 29 is a diagrammatic illustration showing an exemplary Spine Plate.

FIGS. 57A–57C are diagrammatic illustrations showing the addition of bend sensors to the flexible axial rotation sensor.

FIGS. 58A–58C are diagrammatic illustrations showing various specialty joint-sensing devices.

DESCRIPTION OF SPECIFIC EMBODIMENTS

Figure 1A:
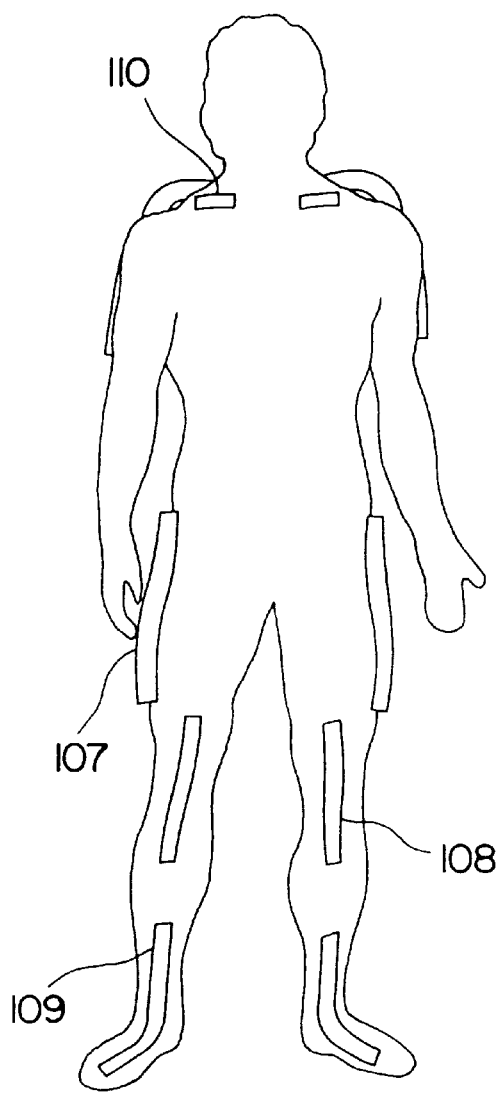
FIG. 1 is a diagrammatic illustration showing front (a) and rear (b) views of an exemplary embodiment of a 39-DOF Sensor Configuration.

The inventive structure and method are now described in the context of specific exemplary embodiments. For convenience, but not by way of limitation, the description is partitioned into a system overview, a description of the kinematic foundation of the mechanical components and assemblies, and a description of elements, components, sensors, assemblies, and the like corresponding to the attached figures.

We now describe an overview of the inventive system and apparatus. In accordance with the subject invention, apparatuses are provided which employ multiple links connected by revolute joints, for measuring body parts, usually human body parts. The link and revolute joint assembly has terminal links for fitting to mounts for the body parts. The mounts secure the terminal links to the body part to minimize movement of the terminal links independent of the movement of the body part. Sensors are provided, where the sensor may extend past a plurality of joints or the sensor may extend over a single joint, with the assembly comprising a plurality of the single sensor joints. Each of these structures has advantages for use in particular situations depending on the information to be processed from the apparatus.

A goniometer-based body-tracking system, referred to herein as the Range-Of-Motion-Suit (ROMS), has been designed as a general measurement tool for determining the positions of various joints on the human body. The principal components of the system are the Lower Extremity Assembly (LEA), the Upper Extremity Assembly (UEA) and the Waist Pack Assembly (WPA). The LEA, which measures lower-body joints, and the UEA, which measures upper-body joints, can be used either separately or together. The WPA is a belt- or desk-mounted device containing the Data Acquisition System (DAS) and various other power-supply and communications functions.

The LEA is a tights-like garment with protective fabric pockets housing sensors to measure the ankle, knee and hip joints. It includes a pair of socked feet to allow ankle instrumentation, mechanical stiffeners to improve measurement accuracy and repeatability, and a series of fabric channels to enclose sensor cabling, and connector pockets to prevent snagging during use.

The UEA is an elastic garment extending from neck to mid-thigh, and covering the arms and hands. It includes fabric pockets housing sensors to measure the wrist, elbow and shoulder joints. Like the LEA, it also incorporates fabric channels to enclose sensor cabling, and connector pockets to prevent snagging.

Resistive bend sensors, such as those described in U.S. Pat. Nos. 5,047,952 and 5,280,265, (each of which is hereby incorporated by reference) form the basis of the angle-sensing technology used in this system. The bend sensors are thin, flexible strips that include two variable-resistance elements. An encapsulant insulates and protects the sensing elements and the electrical connections from external damage. Four wires connect to solder tabs at one end of each sensor. A typical sensor is shown in FIG. 4.

As a sensor element is bent about its minor axis, it undergoes a change in resistance. This change varies linearly with the change in angle between the ends of the sensor. The resistance is also moderately dependent on any twist resulting from torsion about the sensor's major axis. For accurate measurement, therefore, it is important to allow only pure bending of the sensor about its minor axis. The definition of the angle measured by the sensor and an equivalent electrical circuit for the device are shown in FIG. 7 and FIG. 4 respectively.

Figure 5:
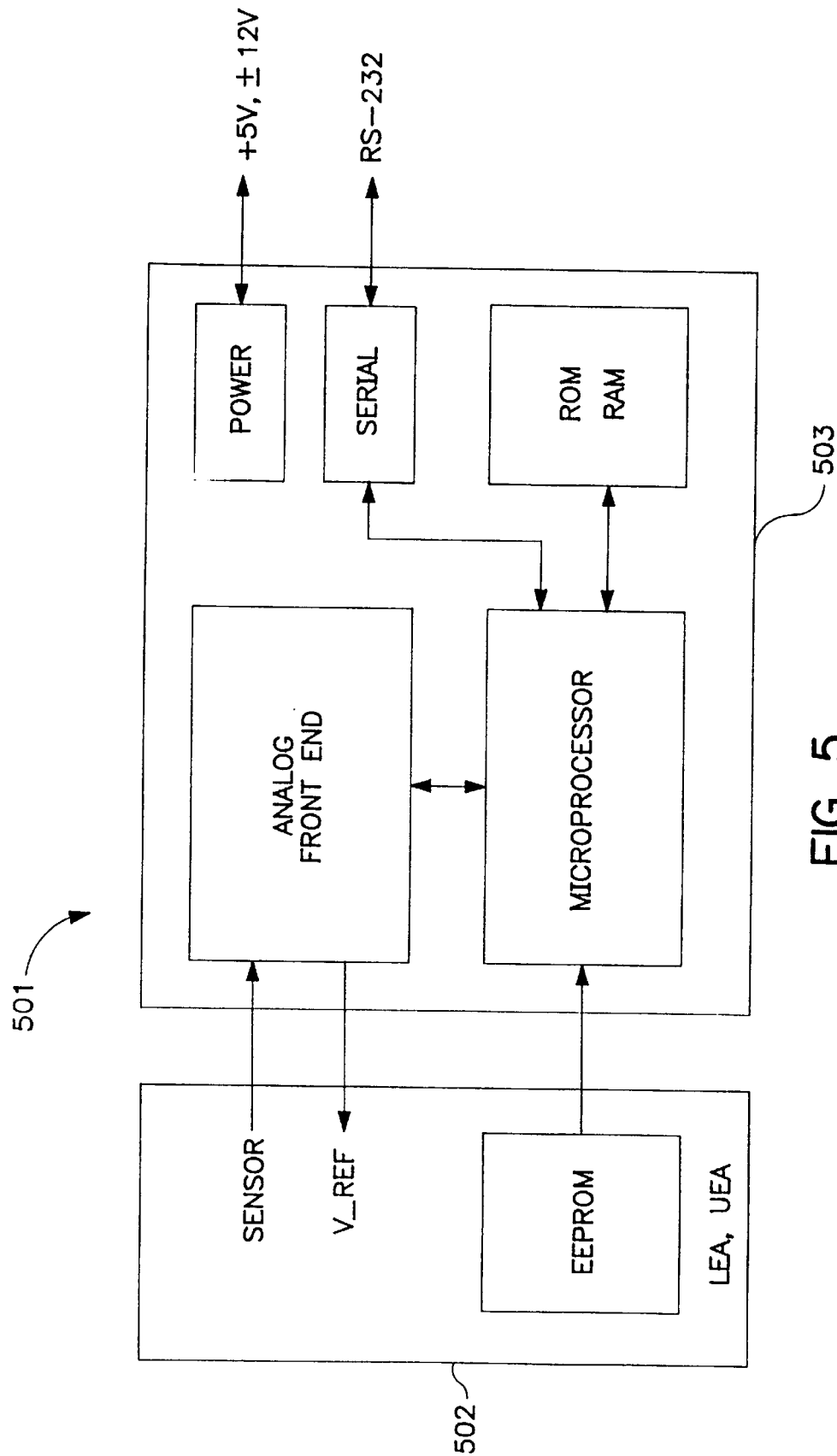
FIG. 5 is a diagrammatic functional block diagram showing the major system functional blocks.
Figure 6:
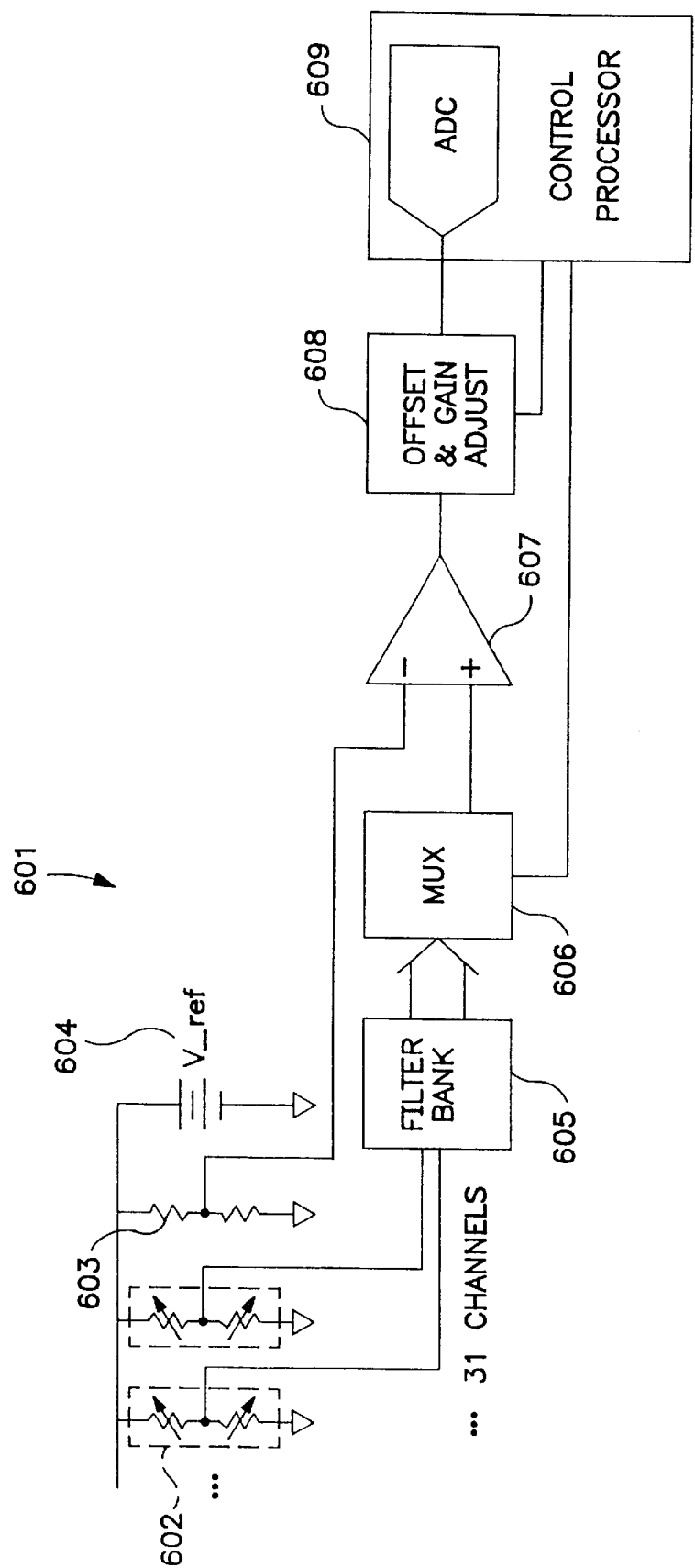
FIG. 6 is a diagrammatic illustration showing an overview of exemplary signal amplification instrumentation contained in the Data Acquisition System.

The system must convert the small change in sensor resistance produced during bending into a usable signal. The instrumentation hardware that performs this function is the Data Acquisition System (DAS). The analog circuitry in the DAS conditions the sensor signals, multiplexes between sensor channels, performs fixed-gain amplification of the sensor signal, applies channel-specific amplification offset and gain correction, and converts the resulting analog signal to a digital value. Each of these operations is explained and discussed below. The functional blocks in the overall DAS and the behavior of the analog signal-conditioning circuitry are shown in FIG. 5 and FIG. 6, respectively.

The DAS measures changes in bend sensor resistance using a Wheatstone bridge circuit. Each sensor provides two piezoresistive elements for the bridge; the other half of the bridge consists of two high-precision reference resistors. The reference resistors are part of every sensor bridge, as an analog multiplexer is used to cycle through all of the sensors in turn. The output of the Wheatstone bridge circuit is conditioned with a single-pole low-pass filter with a 3 dB frequency of 100 Hz. The choice of cutoff frequency strikes a balance between noise rejection and frequency response requirements.

A 31-channel cascaded multiplexing system maps a particular sensor side of the bridge to one input of a fixed-gain instrumentation amplifier. The other differential input of the amplifier is always connected to the pair of precision reference resistors, which forms the reference side of the Wheatstone bridge. A fixed-gain amplification stage, common for all sensor channels, converts the differential bridge signal to a single-ended voltage. To map each individual sensor signal optimally into the range of the analog-to-digital converter (ADC), each sensor has an associated offset and gain value stored in EEPROM. As the DAS multiplexes through the sensor channels, it recalls the corresponding gain and offset from EEPROM and uses them to set programmable components in the second amplification stage.

The sensor assemblies consist of two basic types: flat single degree-of-freedom (1-DOF) assemblies that permit bending about one axis only, and articulated mechanical (multi-DOF) assemblies that allow full rotation between their endpoints. Both types of assemblies can be combined as needed to measure joints of interest on the human body. The sensor assemblies are typically held in pockets sewn into the stretch fabric body of the LEA and UEA garments. The flat 1-DOF assemblies typically slide into long slender pockets and are held firmly against the body by the elasticity in the LEA or UEA garment. The multi-DOF assemblies are typically held in functional relation to the body by an arrangement of fabric pockets, mounting plates, straps and buckles.

We now discuss some of the kinematic foundations of the mechanical assemblies. The underlying mathematical structure of the linkage-based mechanical sensor assemblies is one involving kinematic transformation equations. These matrix equations describe the relative position and orientation of two rigid bodies with respect to one another. Applying several such transformations in succession allows for the determination of the position and orientation of one end of an articulating mechanical assembly with respect to the other. The following paragraphs give a very brief introduction to transformation kinematics in order to explain the function of the mechanical sensor assemblies, such as the right shoulder assembly that is used as the canonical example. For a much more rigorous treatment of this material, see a standard robotics or dynamics text such as "Introduction to Robotics," by John J. Craig, 1989.

Consider two R3 coordinate systems, characterized by two sets of orthonormal basis vectors designated as frame A and frame B. The position of a point P in space is independent of either of these two frames, and can therefore be given equally well in terms of either of the two frame coordinate systems. The x, y, and z positions of point P in frames A and B can be given by the following 4×1 matrices:

$$P_A = \begin{bmatrix} x_A \\ y_A \\ z_A \\ 1 \end{bmatrix} \quad P_B = \begin{bmatrix} x_B \\ y_B \\ z_B \\ 1 \end{bmatrix}$$

A matrix equation is used to translate the coordinates of point P in frame A to a different set of coordinates corresponding to the position of point P in frame B. This equation is:

$$P_A = \begin{bmatrix} R_{00} & R_{01} & R_{02} & x_{AB} \\ R_{10} & R_{11} & R_{12} & y_{AB} \\ R_{20} & R_{21} & R_{22} & z_{AB} \\ 0 & 0 & 0 & 1 \end{bmatrix} P_B$$

where R is a 3×3 direction cosines matrix expressing the relative orientation of frame B with respect to frame A. (As a brief reminder, the three columns of R consist of the projections of the basis vectors of frame B onto the basis vectors of frame A.) The first three elements of the fourth column give the relative displacement of the two frames, i.e., this triad gives the coordinates for the origin of frame B in terms of the basis vectors of frame A. If multiple successive transformations are applied, then the matrices for each individual transformation are multiplied together in order to determine the overall transformation.

The resistive bend sensor used in the current implementation of this invention, as described in U.S. Pat. Nos. 5,047,952 and 5,280,265, (each of which are hereby incorporated by reference) measures the total angle over which it spans, and therefore allows for the lumping together of multiple parallel-axis revolute joints into "joint sets" that can be characterized with a single angle measurement. If this is done, however, it is no longer possible to determine the translation (fourth-column) vector between frames attached to two successive joint sets. Therefore, for simplicity, in all subsequent matrix derivations the translation vector in the fourth column of the generalized transformation matrix is replaced with three zero values, and all subsequent discussion will concentrate on the rotational component of the general transformation matrix.

When all of the transformation matrices for moving from one frame to the next have been multiplied together, the resulting matrix gives the net rotation from the first frame to the last. This information can be used to translate the coordinates of a point from one frame to the other, but it can also be used to describe the relative orientation of the two frames without reference to a specific point. This is the technique used with the mechanical linkage sensor assemblies.

When using a multi-segment linkage assembly to measure the relative orientation of two body parts, such is as done at the hip and shoulder joints, there are generally four frames of interest:

Frame P, which fixed to the first (proximal) body part

Frame A, which is fixed to the proximal end of the linkage assembly

Frame Z, which is fixed to the distal end of the linkage assembly

Frame D, which is fixed to the second (distal) body part

The three basic components of any orientation measured by a linkage assembly are therefore:

$T_{PA}$, which gives the orientation of the start of the linkage with respect to the first body part $T_{AZ}$, which gives the orientation of the end of the linkage with respect to the start of the linkage $T_{ZD}$, which gives the orientation of the second body part with respect to the end of the linkage. For both the typical hip and shoulder examples, the distal link is assumed to be always parallel to the distal body part. This matrix, therefore, reduces to a simple one containing only terms from the set {−1, 0, 1}.

Multiplying these three matrices together gives the net orientation of the second body part with respect to the first body part:

$$T_{PD} = T_{PA} T_{AZ} T_{ZD}$$

Once $T_{PD}$ has been determined, it is a straightforward matter to express the relative orientation of the two body parts using any of several desired representation schemes. Examples of methods for describing the relative orientation two coordinate frames include, but are not limited to:

Direction cosine matrices, which are 3×3 matrices that give the basis vectors of the second frame in terms of those for the first frame Fixed-frame (space) angle triads, where the second frame is initially aligned with the first, then given three successive rotations about the first (stationary) frame axes.

Euler (body) angle triads, where the second frame is initially aligned with the first, then given three successive rotations about its own (non-stationary) frame axes.

Angle-axis vectors, where the second frame is initially aligned with the first, then given one rotation scalar about a single axis vector to bring it into its final position.

Quaternions, which use four parameters to express the rotation of frame 2 with respect to frame 1 in a mathematically useful way.

For this invention, the resulting $T_{PD}$ is characterized using Euler angle triads. This method happens to be convenient in this application, as it tends to be more human-readable and intuitive than the other methods that require matrix or vector notation, but any of the above may alternatively be used instead. When using the resulting information to build and render the image of a human body, for example, it may be more efficient to express the rotation using a direction cosines matrix, especially if the computer hardware being used has been optimized to perform very rapid matrix multiplication.

We now describe the inventive structure and method in the context of particular exemplary structures, devices, elements, and assemblies illustrated relative to the figures.

Figure 1B:
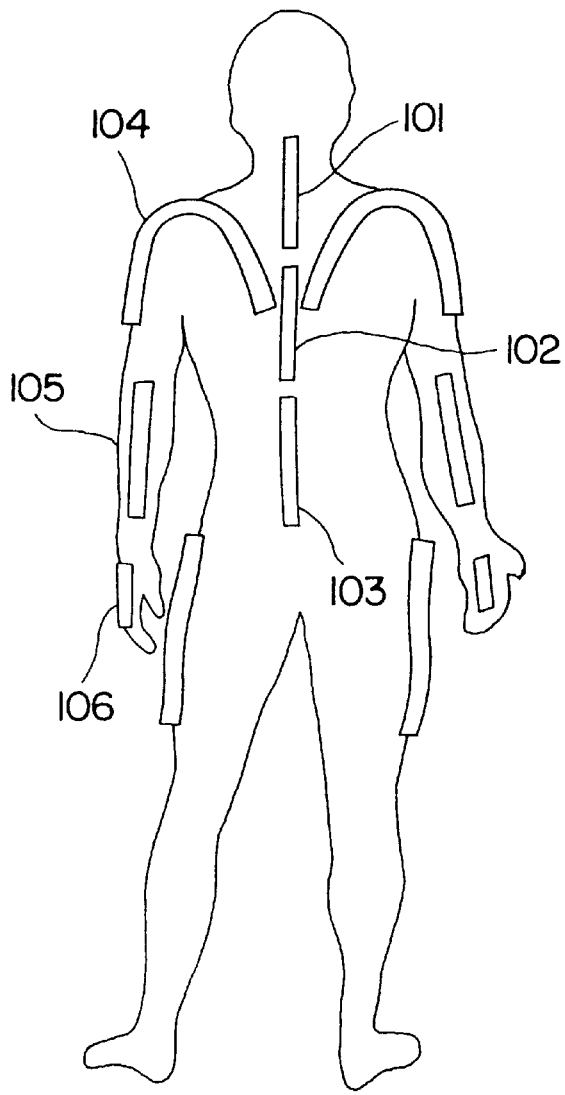

FIG. 1 shows an exemplary arrangement for placing sensor assemblies on a human body. This configuration instruments most of the major joints on the body, and (combined with devices to measure hand motion, e.g., a CyberGlove® instrumented glove made commercially available by Virtual Technologies, Inc., of Palo Alto, Calif., and a $5^{th}$ Glove made commercially available by 5DT Corporation, South Africa) affords body coverage that may, depending on the application, be considered as essentially complete. Sensors assemblies marked with a "(3)" after the name (not to be confused with a drawing reference numeral) measure a full three rotational degrees of freedom. Sensors marked with a "(1)" or a "(2)" are located on joints with less than complete rotational freedom, and are therefore simpler devices. Assemblies include the upper back (3) assembly (101), Middle Back (3) assembly (102), Lower Back (3) assembly (103), Shoulders (3) assembly (104), Shoulder "Shrug" (2) assembly (106), Elbow (1) assembly (105), Forearm and Wrist (3) assembly (106), Hip (3) assembly (107), Knee (1) assembly (108), and Ankle (2) assembly (109). Each of these components or assemblies is disposed proximate or adjacent the associated human body part or parts as illustrated in the figure.

Figure 2A:
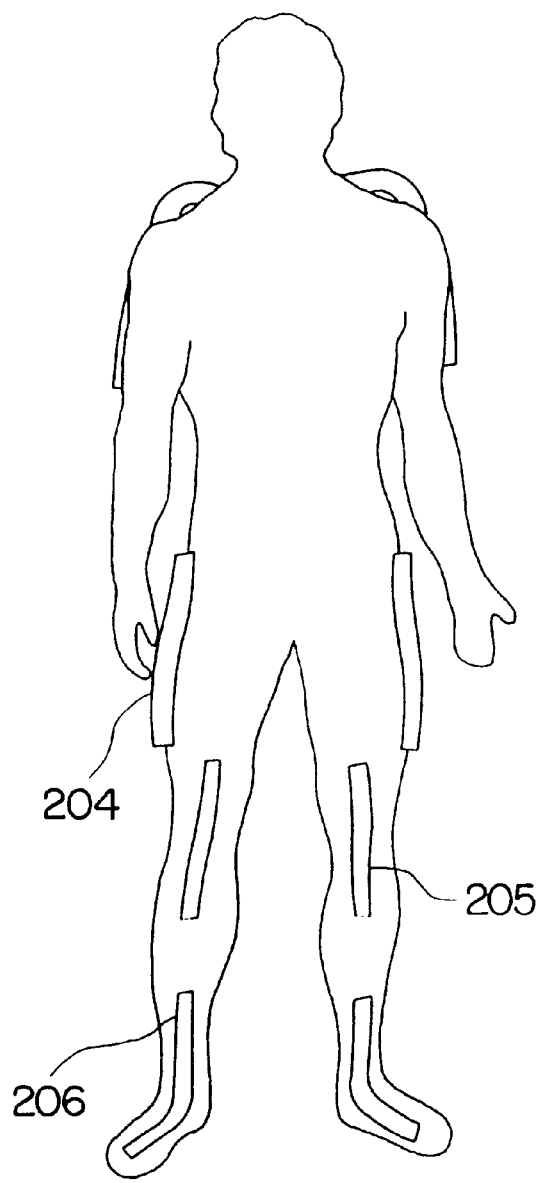
FIG. 2 is a diagrammatic illustration showing front (a) and rear (b) views of an exemplary embodiment of a 22-DOF Sensor Configuration.
Figure 2B:
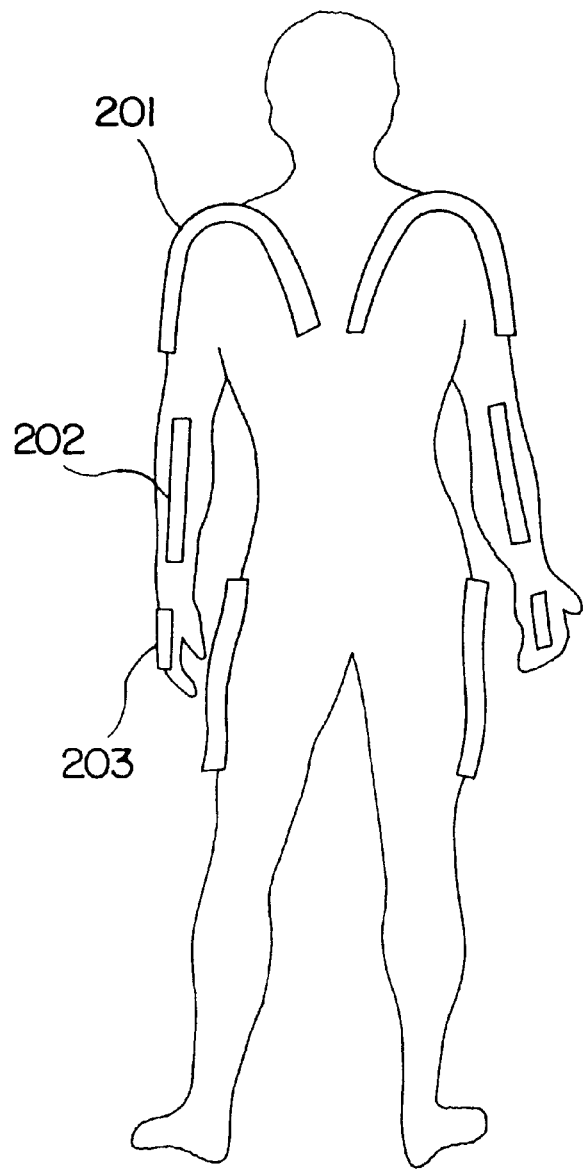

A particularly useful subset of the assemblies illustrated and described relative to FIG. 1, is now described relative to FIG. 2. The assemblies in FIG. 2 include: Shoulders (3) assembly (201), Elbow (1) assembly (202), Wrist (2) assembly (203), Hip (3) assembly (204), Knee (1) assembly (205), and Ankle (2) assembly (206). Again, each of these assemblies are disposed proximate or adjacent to the associated human body part or parts as illustrated in the figure.

Figure 3A:
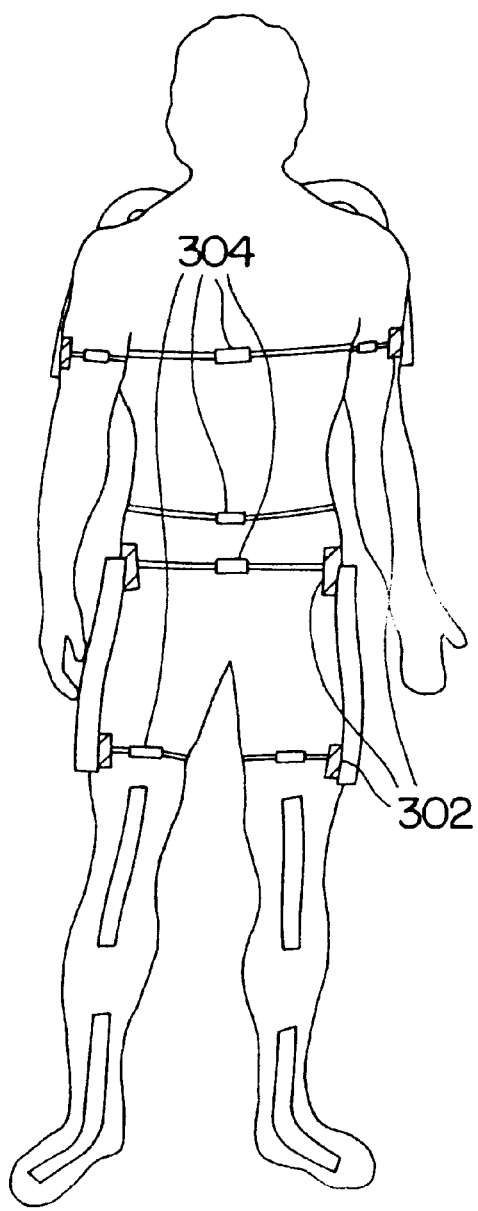
FIG. 3 is a diagrammatic illustration showing front (a) and rear (b) views of an exemplary embodiment of the 22-DOF Configuration illustrated in FIG. 2, including mounting details.
Figure 3B:
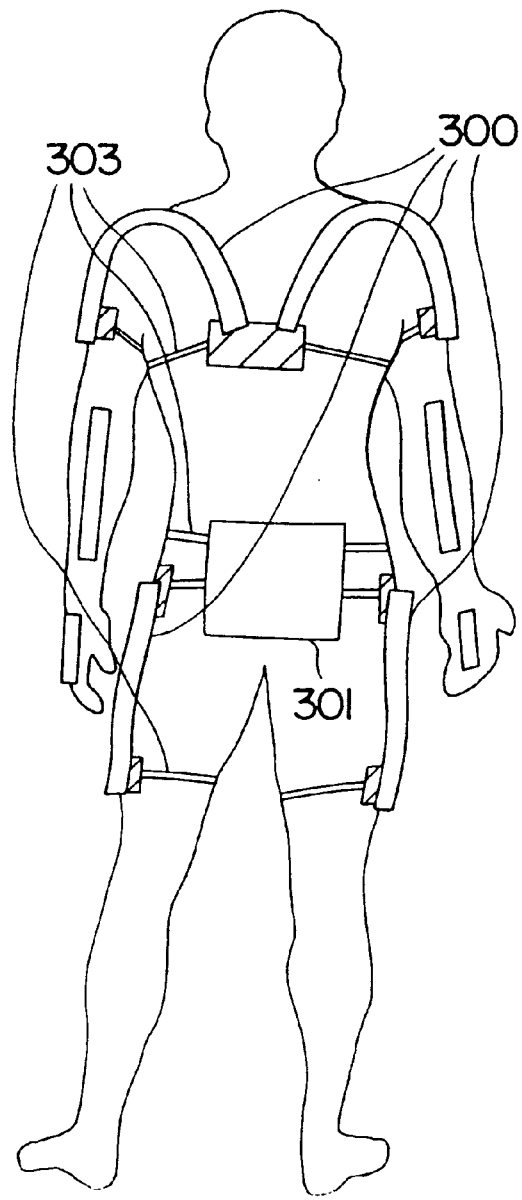
Figure 4A:
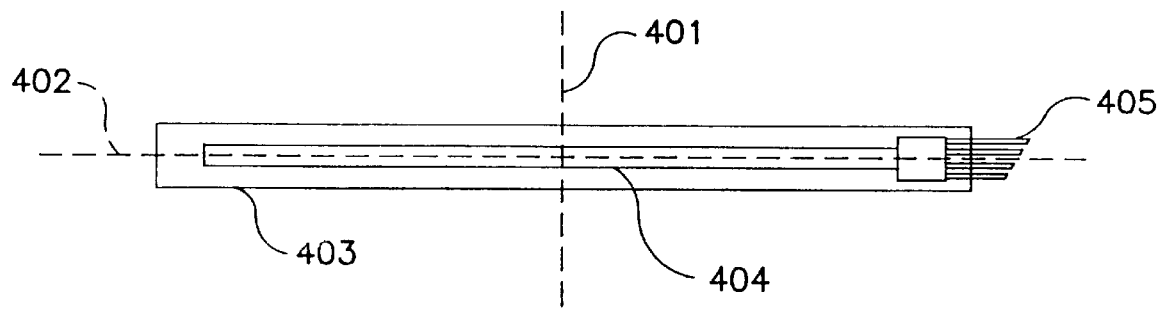
FIG. 4 is a diagrammatic illustration showing fundamental features of an exemplary resistive bend sensor, including (a) a mechanical structure and (b) the equivalent electrical circuit.
Figure 4B:
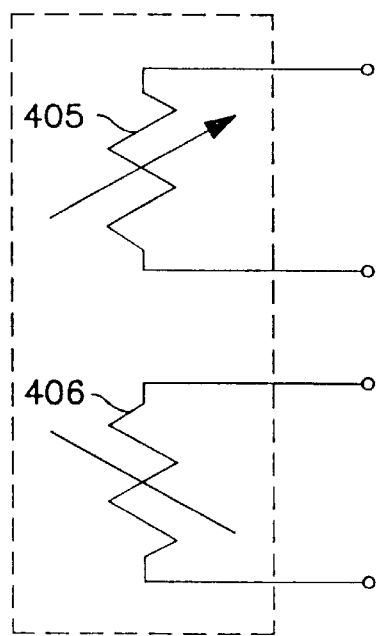

FIG. 3 shows further details for the sensor configuration given in FIG. 2. Each of the three degree-of-freedom linkage-based assemblies (300) is shown with corresponding endpoint plates (301), straps (303) and buckles (304). These hold the assembly in functional arrangement on the body, and permit the mechanism to be firmly affixed to the corresponding body parts. FIG. 3 also shows the belt-mounted Waistpack Assembly (WPA) (301), which includes the Data Acquisition System (DAS) and other system electronics. It can also be used in a desk-mounted mode or otherwise supported, using extension cables to transmit signal information from the sensors to the WPA FIG. 4a shows a mechanical overview of a resistive bend sensor package, including the minor axis (401) about which bending is intended to occur. FIG. 4b shows an equivalent electrical circuit for the device, which consists of two resistive elements (405 and 406) arranged such than bending the sensor causes one resistance to increase and the other to decrease.

FIG. 5 shows an overview (501) of the major functional blocks in the main system. It consists of the sensors held in the LEA and UEA garments (502), plus a Data Acquisition System (503) to process and transmit sensor data to a host computer, including a processor (or microprocessor) input/ouptut port(s), memory, and other conventional computer elements.

FIG. 6 shows an overview (601) of the signal amplification instrumentation contained in the DAS. Each pair of resistive sensing elements (602) is selected in turn by an analog multiplexer (606), then compared with a pair of reference resistors (603) and excitation voltage (604) in a Wheatstone bridge configuration. Each sensor signal is sent through a first-order low-pass filter (605) with a corner frequency of 100 Hz and is then preamplified (607). Each sensor signal is given a channel-specific gain and offset correction (608) to ensure that it is in the correct range for the subsequent analog-to-digital converter (609).

Figure 7A:
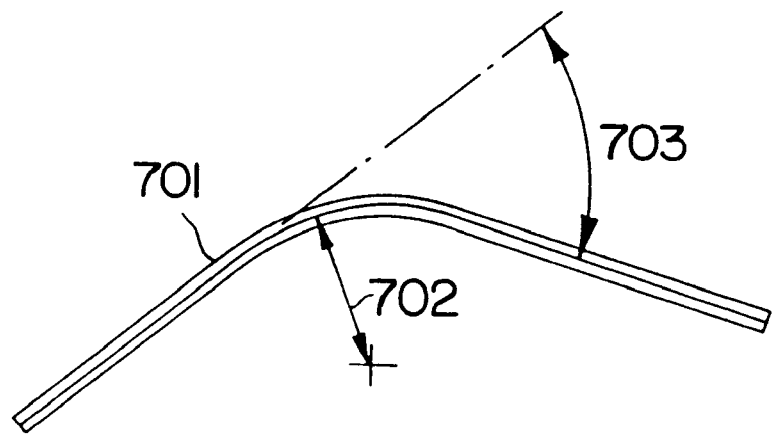
FIG. 7 is a diagrammatic illustration showing (a) principles of operation of a bend sensor and (b) an exemplary single resistive bend sensor spanning two parallel-axis joints of a three-link mechanism.
Figure 7B:
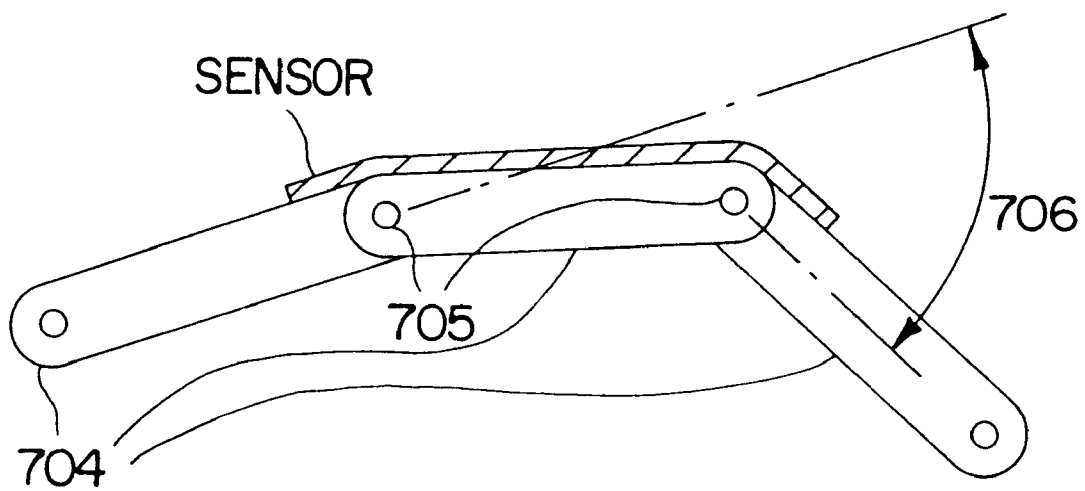

FIG. 7a shows the fundamental operating principles of the resistive bend sensor (701) of U.S. Pat. Nos. 5,047,952 and 5,280,265. This sensor produces a signal whose output change is proportional to the change in angle (703) between its ends. This behavior makes it ideal for measuring the sum of the angles about multiple parallel axes. FIG. 7b shows a single resistive bend sensor spanning two parallel-axis joints (705) of a three-link (704) mechanism. As this figure shows, the angle (706) reported by the resistive bend sensor is equal to the sum of the individual angles spanned by this instrument. This principle can be also be used to measure the combined angle across three or more parallel-axis joints.

FIG. 8 shows a sensor assembly (801) that uses the resistive bend sensor (804) to measure a single rotational degree of freedom. In this implementation, the sensor is constrained by two long flat plastic guides (802 and 803), as well as a number of guiding spacers (805). This arrangement ensures that the sensor bends about its short axis only, so that it neither twists nor yaws. Such assemblies are flat and low-profile, and are appropriate for measuring body joints with only one clear axis of rotation. Examples of such joints include the knee and the elbow.

Figure 9:
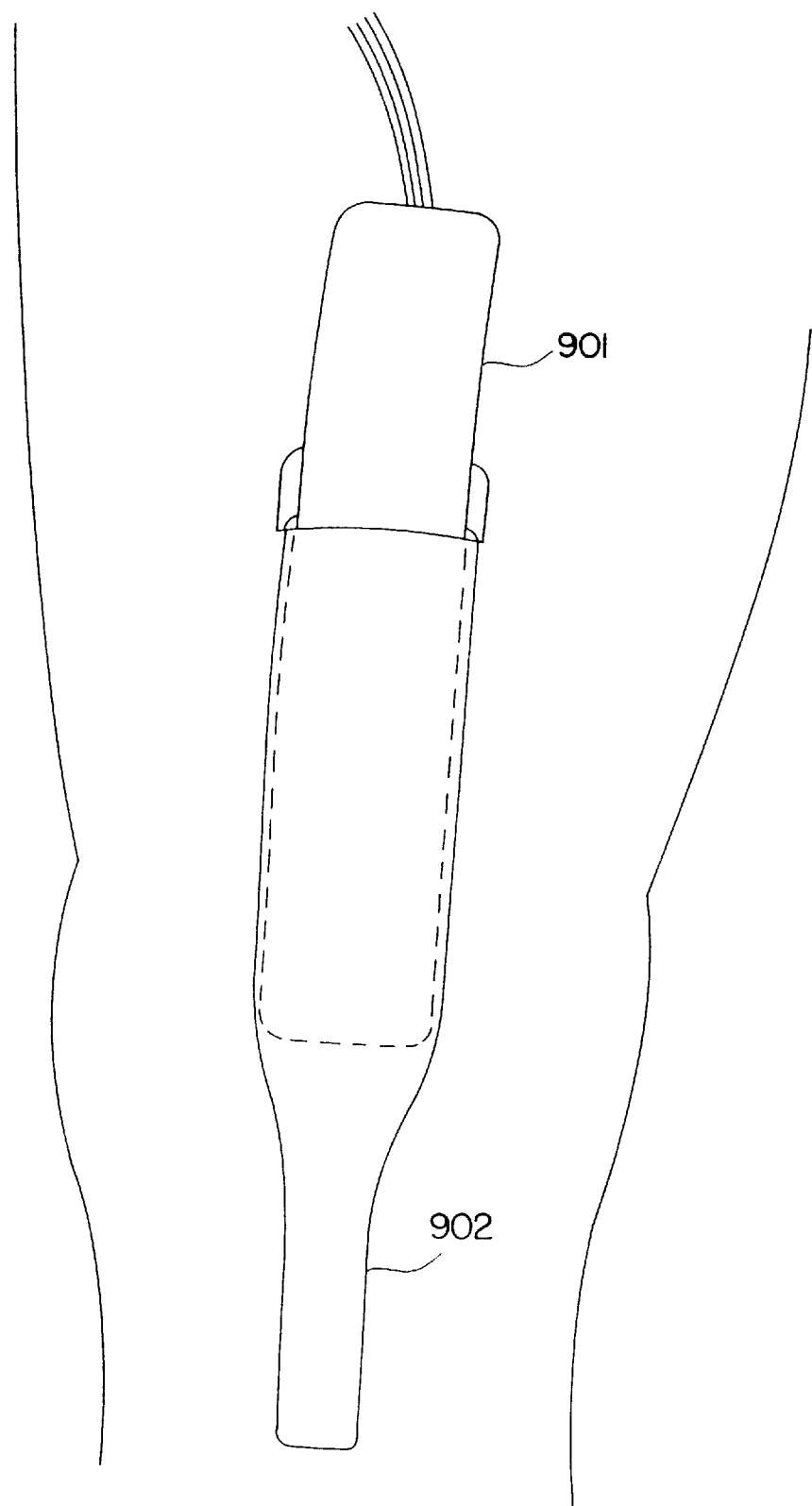
FIG. 9 is a diagrammatic illustration showing an exemplary 1-DOF assembly partially inserted into a fabric pocket on a suit.

FIG. 9 shows the partial insertion of a typical 1-DOF sensor assembly (901) into a fabric pocket (902) on the suit. Other methods of attachment of the sensor may alternatively be employed.

Figure 10:
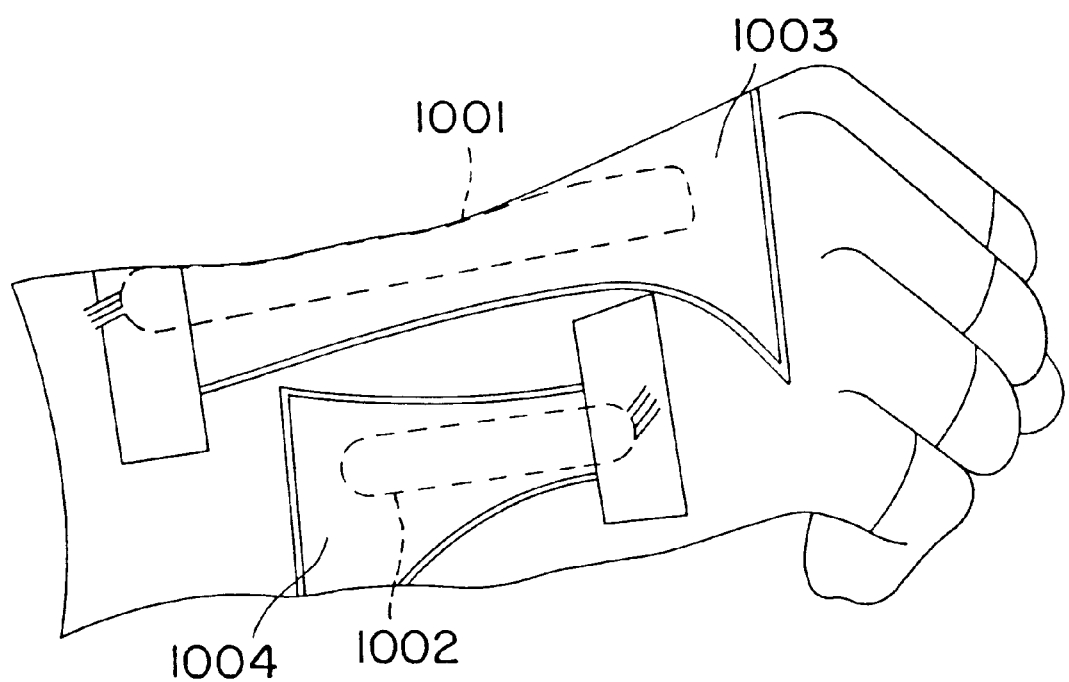
FIG. 10 is a diagrammatic illustration showing an exemplary application of a pair of 1DOF sensors configured to measure top and side wrist angles.

FIG. 10 shows an useful application of a pair of typical 1DOF sensors (1001 and 1002) configured to measure the top and side wrist angles of the hand. Each sensor is held in a fan-shaped fabric pocket (1003 and 1004), which allows the sensors to slide laterally when bending occurs around the axis of the other sensor. This effectively decouples the two motions, and allows the joint to be treated as a pair of independent single-DOF revolute joints, instead of as a compound, two-DOF joint.

Figure 11:
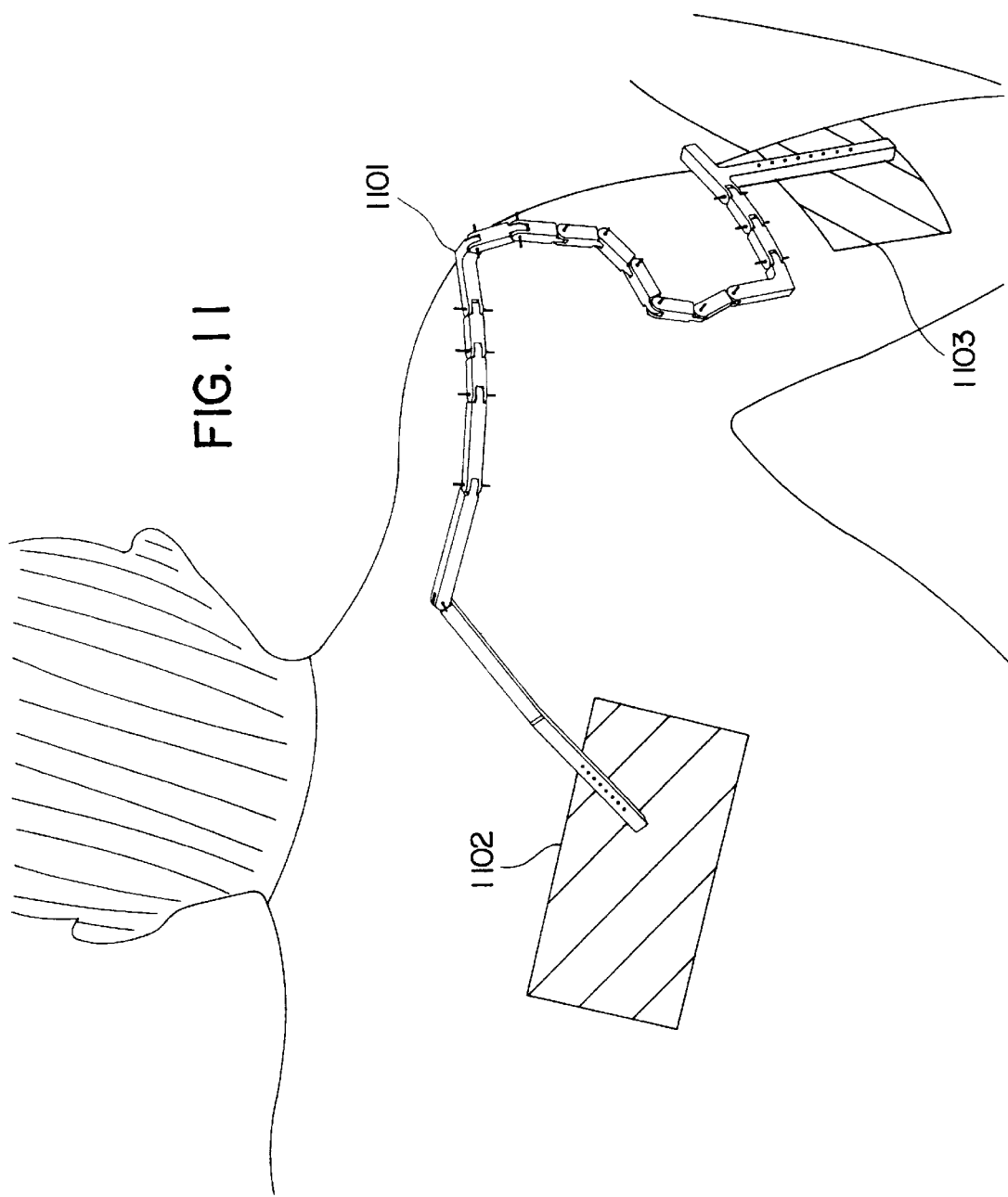
FIG. 11 is a diagrammatic illustration showing an exemplary mechanical linkage element configuration for use on the right shoulder of the human body.

FIG. 11 shows a sample configuration of mechanical linkage elements (1101), arranged in a fashion appropriate for use on the right shoulder of the human body. At both the proximal (spine) and distal (arm) ends of the mechanical structure, the linkage is held to the body with a fastening arrangement (1102 and 1103). These fastening arrangements ensure that the structure is held firmly to the body and therefore tracks closely any motion made by the wearer. In practice, a sensor such as a resistive bend sensor is associated with each joint. Alternate goniometers may conveniently be employed, such as Hall-effect sensors, optical encoders, potentiometers, resolvers and the like.

Figure 12:
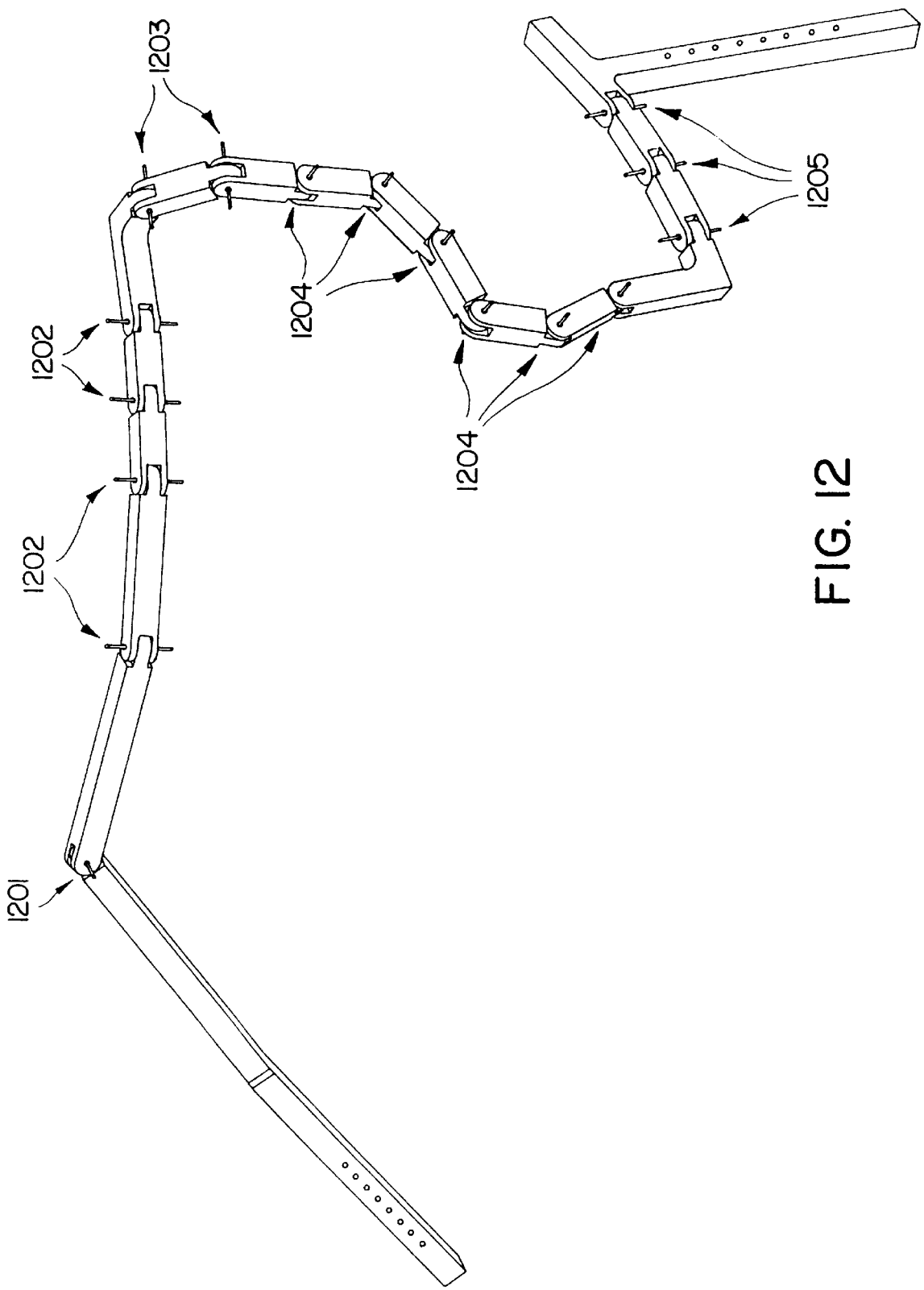
FIG. 12 is a diagrammatic illustration showing detail of the right-shoulder mechanical linkage in FIG. 11.

FIG. 12 shows a close-up of the sample right-shoulder linkage shown in FIG. 11. The line at each of the revolute joints represents the axis of rotation for that joint. As discussed, resistive bend sensors can span more than one revolute joint, so parallel joints can be gathered conceptually into "joint sets." These joint sets (1201, 1202, 1203, 1204 and 1205) may be measured with a single such bend sensor. As shown, this particular shoulder configuration includes five joint sets and therefore requires five bend sensors to instrument fully. As the number of joint sets is increased beyond the theoretical minimum required to allow full range of motion, the linkage can be made to lie flatter to the body and be correspondingly less intrusive to the wearer. The sample configuration shown is a typical one, and achieves a reasonable balance between the two goals of minimizing the instrumentation complexity and minimizing the profile of the device.

Figure 13:
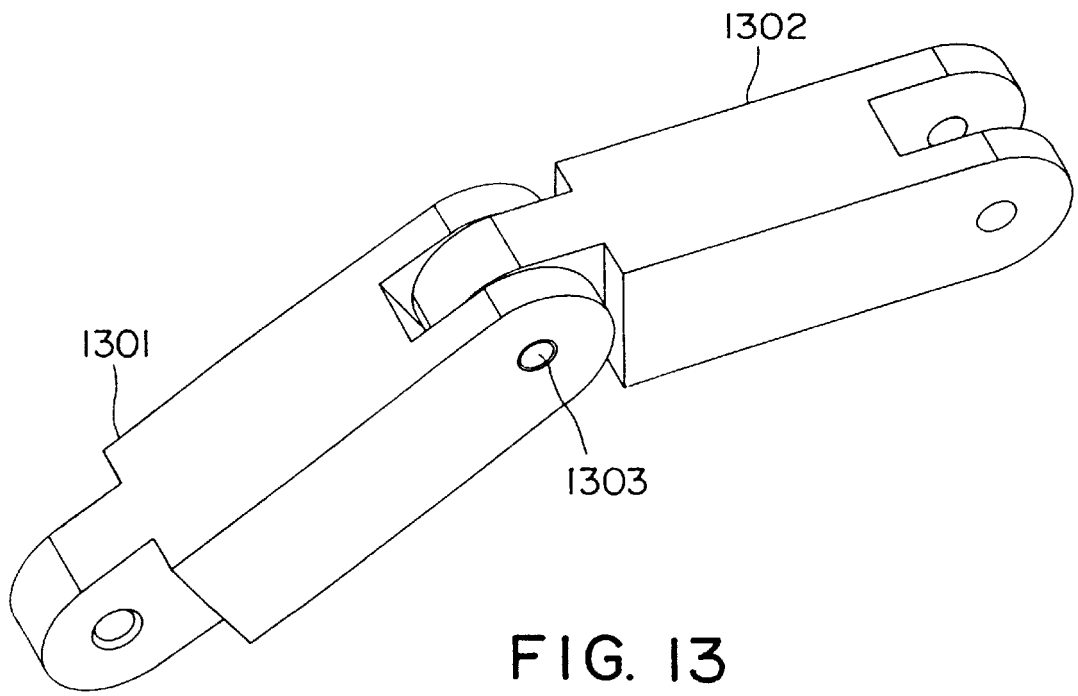
FIG. 13 is a diagrammatic illustration showing an exemplary embodiment of a typical revolute joint between adjacent links.

FIG. 13 shows a typical revolute joint between two adjacent links (1301 and 1302) in a mechanical assembly such as the one shown in FIG. 12. This joint shown here can take any number of forms, including (but not limited to) a pinned joint, a tongue-and-groove joint, a joint between molded plastic parts with integral détente features, a joint between self-lubricating materials, a joint incorporating a bushing, or a joint incorporating a bearing. In general, the particular joint implementation will involve a trade-off between performance and some other factor, such as cost, weight or complexity of assembly. A typical implementation for such a joint uses a dowel pin (1303) to join two self-lubricating plastic parts.

Figure 14:
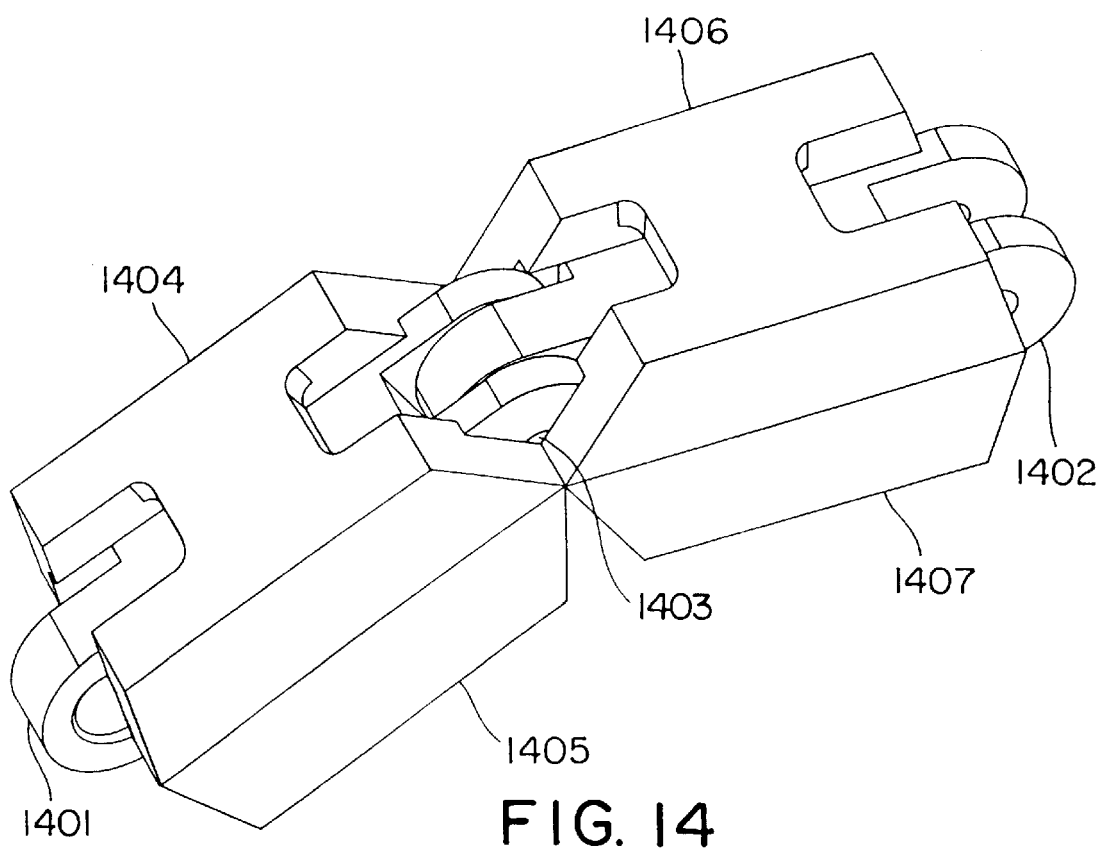
FIG. 14 is a diagrammatic illustration showing an exemplary embodiment of a typical revolute joint between adjacent links with the addition of a typical set of guide stops around the links.

FIG. 14 shows a typical link pair (1401 and 1402), but with the addition of a typical set of guide stops (1404, 1405, 1406 and 1407) around the links. These guide stops are useful for limiting the angle through which any particular joint can revolve. They are also useful for covering and protecting any bend sensor lying along the linkage assembly. In the sample configuration shown, the guide stops consist of pairs of plastic covers, enclosing the linkage in a clamshell fashion. The sample shown includes integral angle constraints, as well as a channel between the link and the guide to allow passage of a bend sensor.

Figure 15:
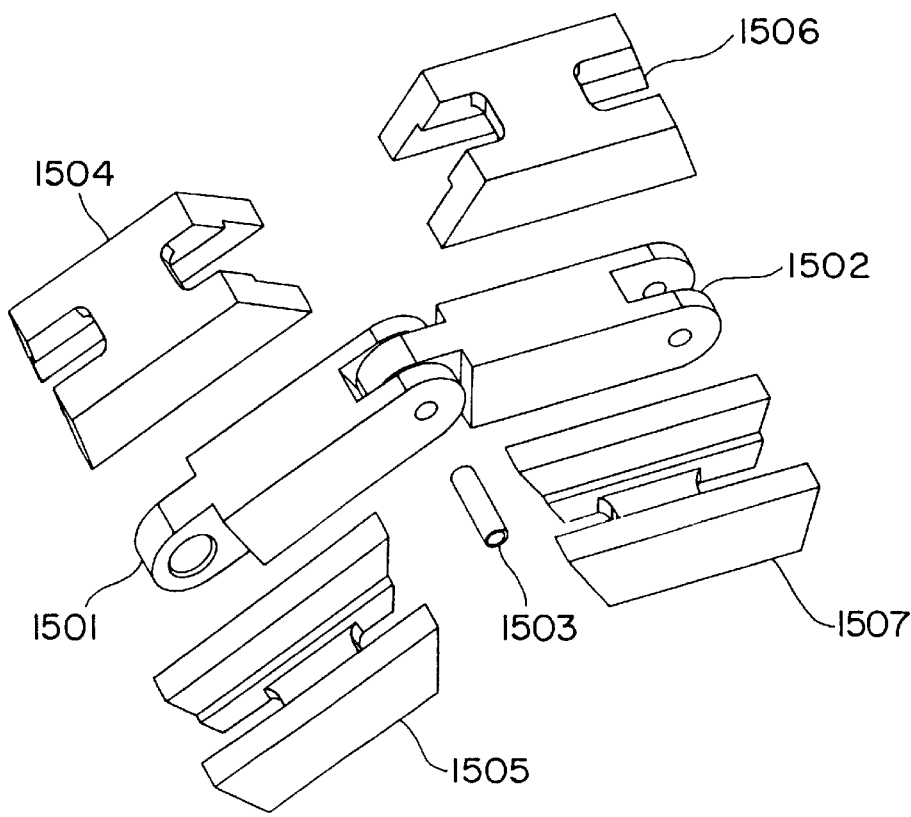
FIG. 15 is a diagrammatic illustration showing an exploded assembly of the structure in FIG. 14.

FIG. 15 shows the same sample link pair (1501 and 1502) configuration given in FIG. 14, but with the various constituent parts exploded to show assembly. In this sample configuration, a dowel pin (1503)joins the two plastic links, and the pairs of guide stops (1504, 1505, 1506 and 1507) are attached in a clamshell fashion around their corresponding links.

Figure 16:
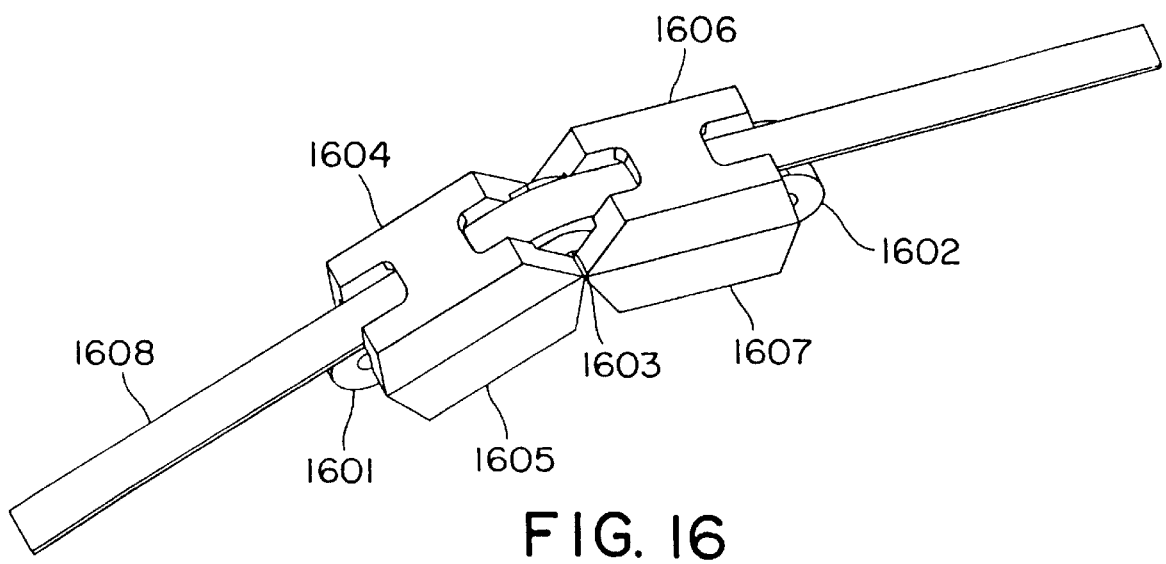
FIG. 16 is a diagrammatic illustration showing an exemplary embodiment of a typical revolute joint with guide stops and a resistive bend sensor.

FIG. 16 shows a typical link pair (1601 and 1602) with guide stops (1604, 1605, 1606 and 1607), but with the addition of a resistive bend sensor (1608) on the top surface of the link pair. As shown, the sensor is protected by the set of guide stops and is further constrained to bend about its short axis only.

Figure 17:
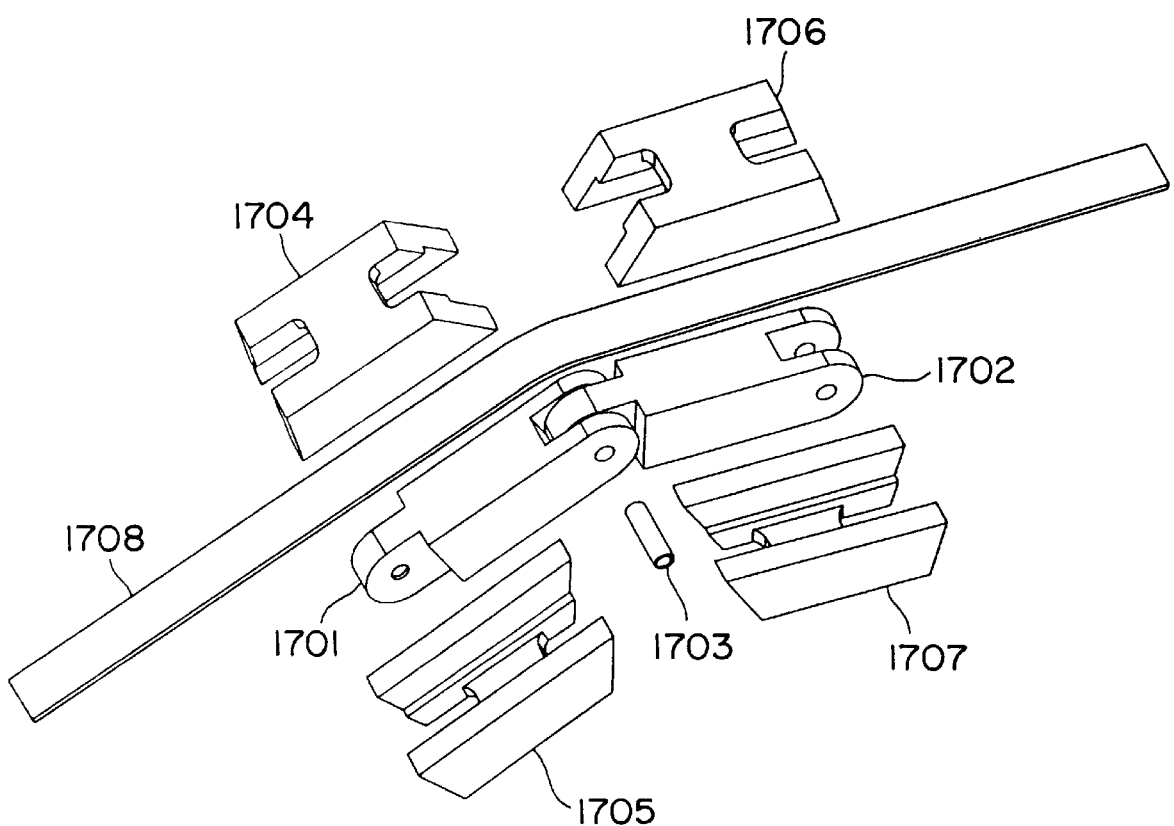
FIG. 17 is a diagrammatic illustration showing an exploded assembly of the structure in FIG. 16.

FIG. 17 shows the same sample link pair (1701 and 1702) configuration given in FIG. 16, but with the various constituent parts exploded to show assembly and the position of the bend sensor (1708).

Figure 18:
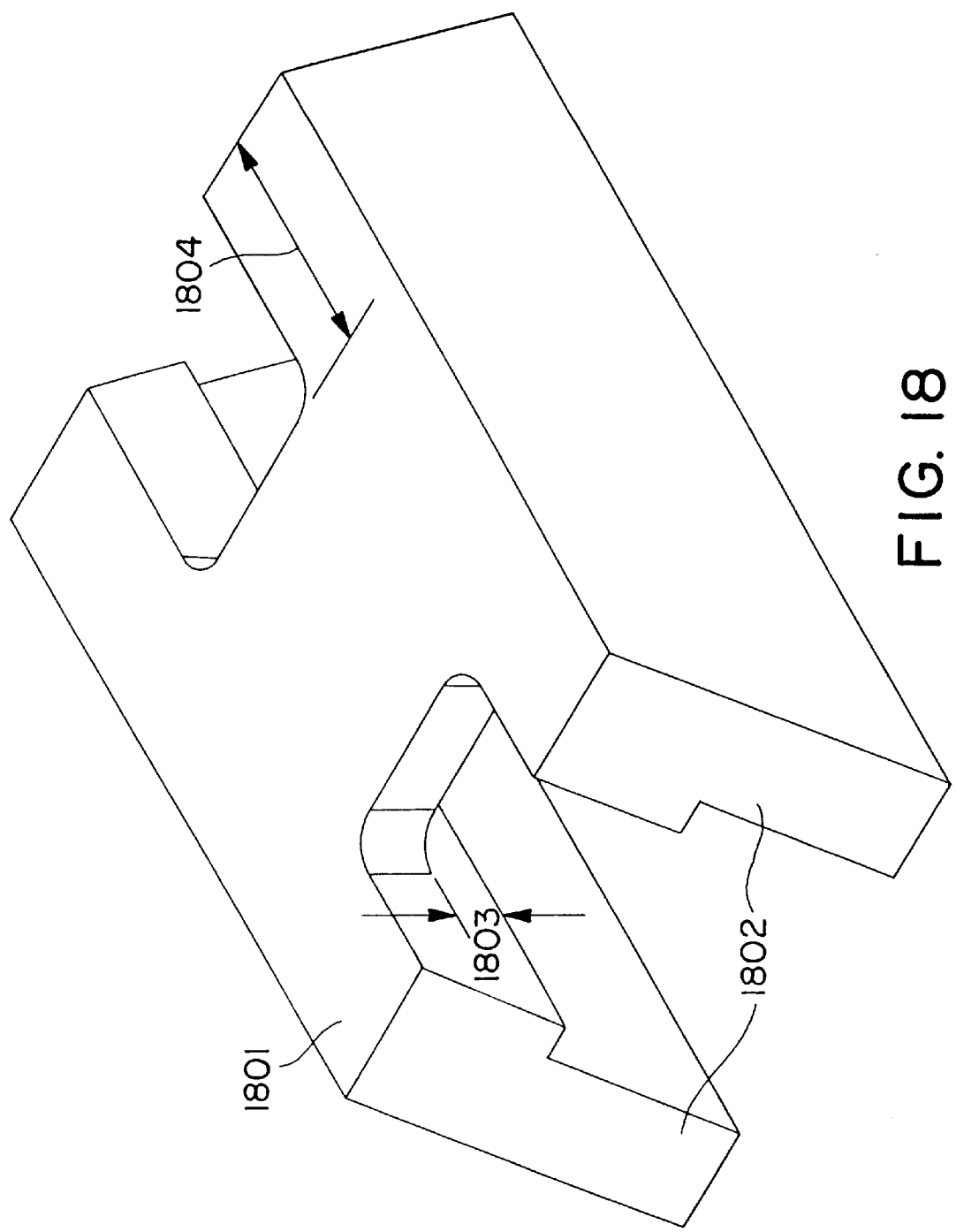
FIG. 18 is a diagrammatic illustration showing an exemplary embodiment of a Guide Stop.

FIG. 18 shows a close-up view of a typical guide stop (1801) from the configuration given in FIGS. 14 through 17. In this configuration, angle constraints are applied to the joint motion by the interference between the faces (1802) of adjacent guide stops. A gap (1803) for allowing passage of a bend sensor is included, as is a region (1804) to prevent the bend sensor from being pinched during joint motion.

Figure 19A:
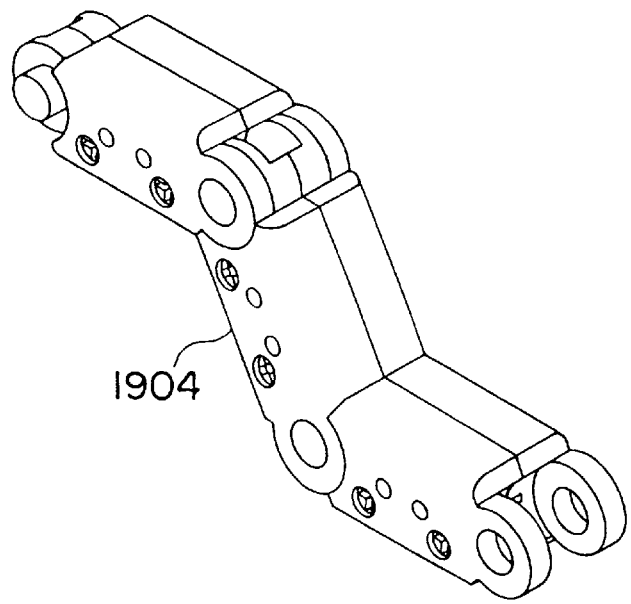
FIG. 19 is a diagrammatic illustration showing an exemplary embodiment of an alternative linkage implementation, including both (a) assembled and (b) exploded views.
Figure 19B:
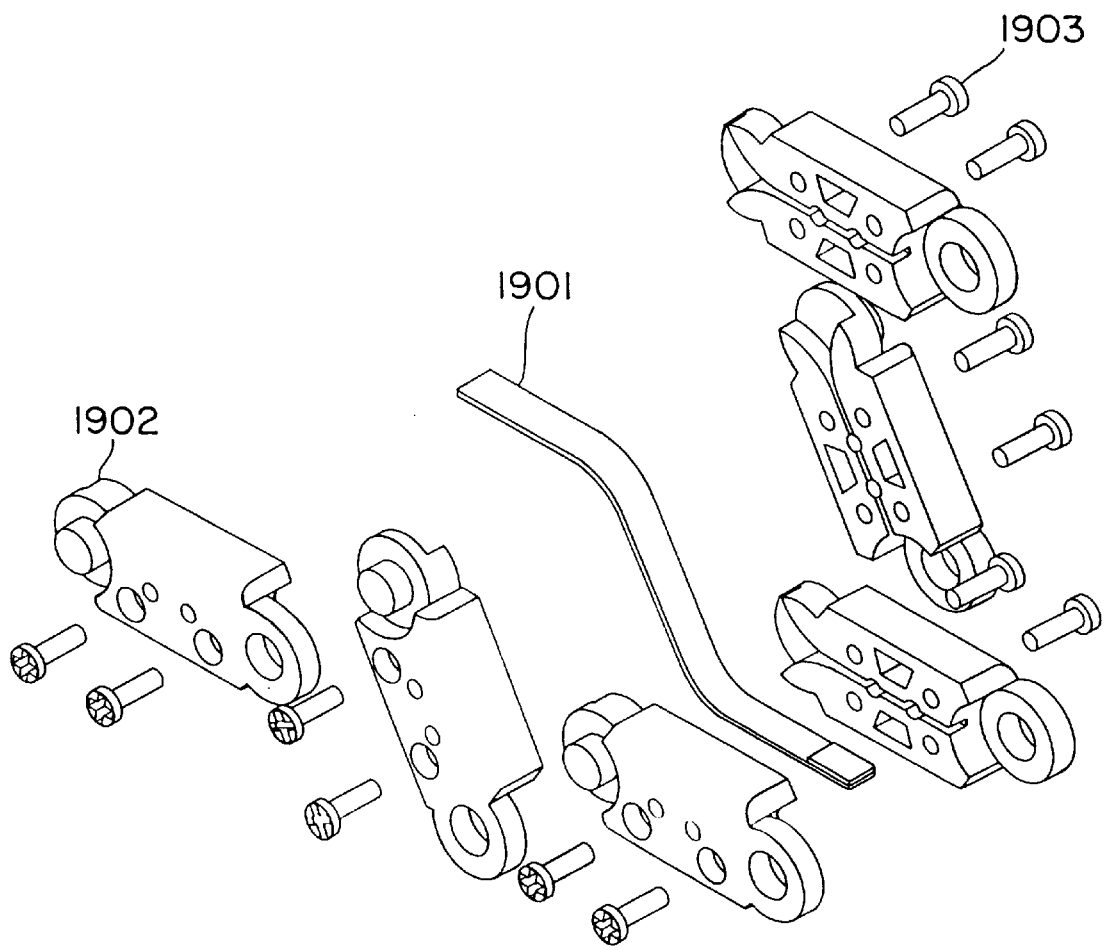

FIG. 19a shows an exploded assembly view of three links in another, alternate arrangement for an articulating mechanical sensor assembly. In this version, the bend sensor (1901) lies on the neutral axis of the linkage (1902) cross-section, instead of in an off-axis position as in the design shown in FIG. 17. (This feature has the advantage of causing little motion in the free end of a bend sensor as the mechanism articulates, which simplifies linkage selection and mechanism synthesis.) A bend sensor is shown in the middle, encased in self-lubricating plastic link halves. The link elements shown are joined using self-tapping screws (1903) to facilitate assembly and disassembly, although they may also be joined using integrally molded snap-fit elements. Holes are included in the sides of the links to provide access to sensor wiring. FIG. 19a shows this design with the links in their typical assembled state (1904).

Figure 20:
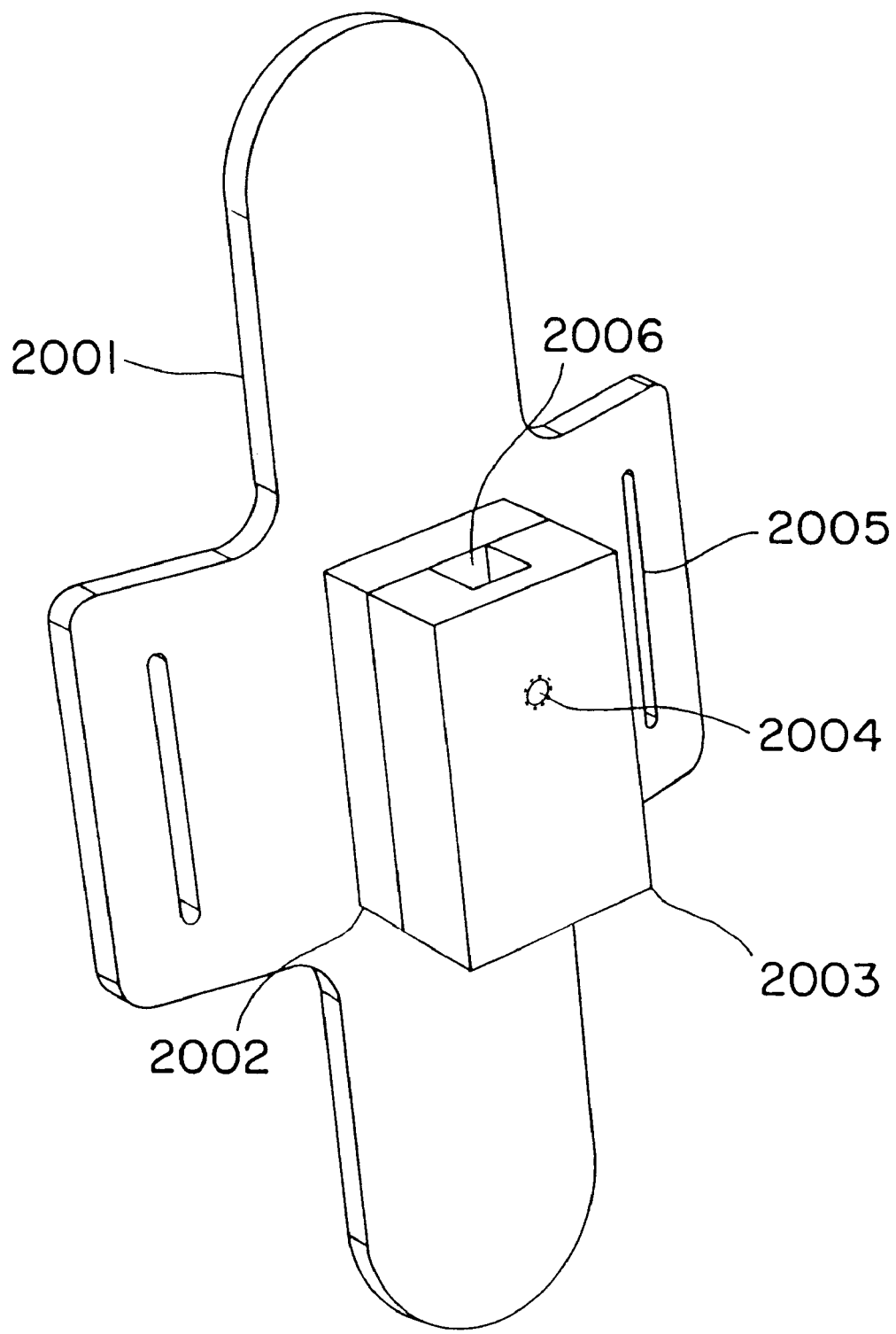
FIG. 20 is a diagrammatic illustration showing an exemplary embodiment of a Mounting Plate for holding a mechanical linkage assembly in functional relationship to the body of the wearer.

FIG. 20 shows a typical arrangement for holding a mechanical linkage assembly in functional relationship to the body of the wearer. The square cross-sectioned hole (2006) made by the endpoint holder (2003) and the spacer (2002) acts as a receptacle for the final link of the linkage structure, which is held secure by a screw threaded (2004) into the endpoint holder. The curved plate (2001) fits flush to the body, and is adjusted to be held firmly by nylon straps passed through slots (2005) in the plate. The arrangement detailed in this figure is the one typically used to hold the shoulder and hip assemblies to the arms and legs, respectively.

Figure 21:
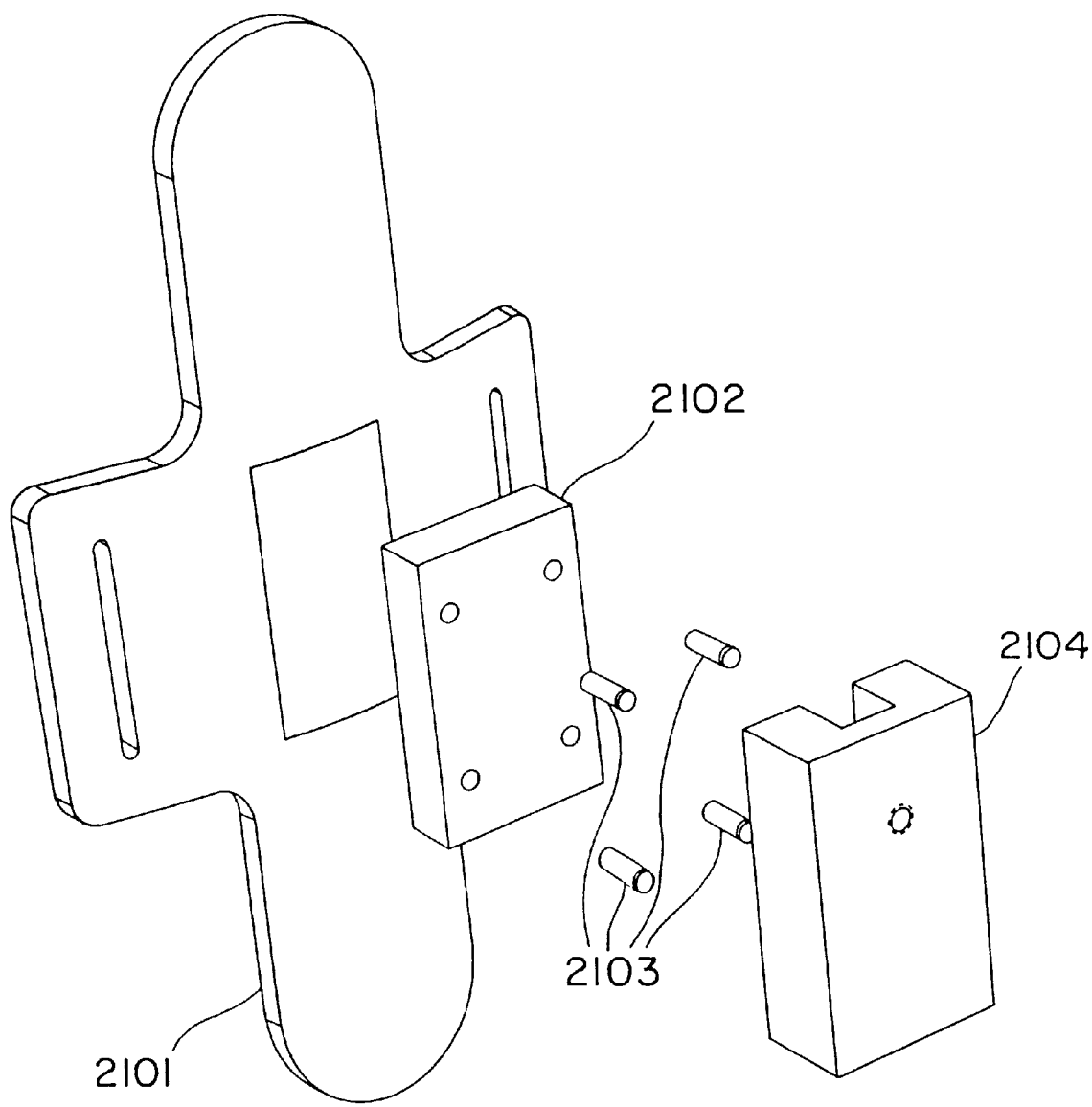
FIG. 21 is a diagrammatic illustration showing an exploded assembly of the structure in FIG. 20.

FIG. 21 shows an exploded view of FIG. 20. In this implementation, the parts are joined with adhesives and dowel pins (2103), although the necessary fixation can be achieved with a wide variety of structures and methods. For example, the linkage can be attached to the fixation plate via methods that include (but are not limited to) a threaded fastener, a detented snapfit between link and holder, a cam lock, a friction fit, or the like.

Figure 22:
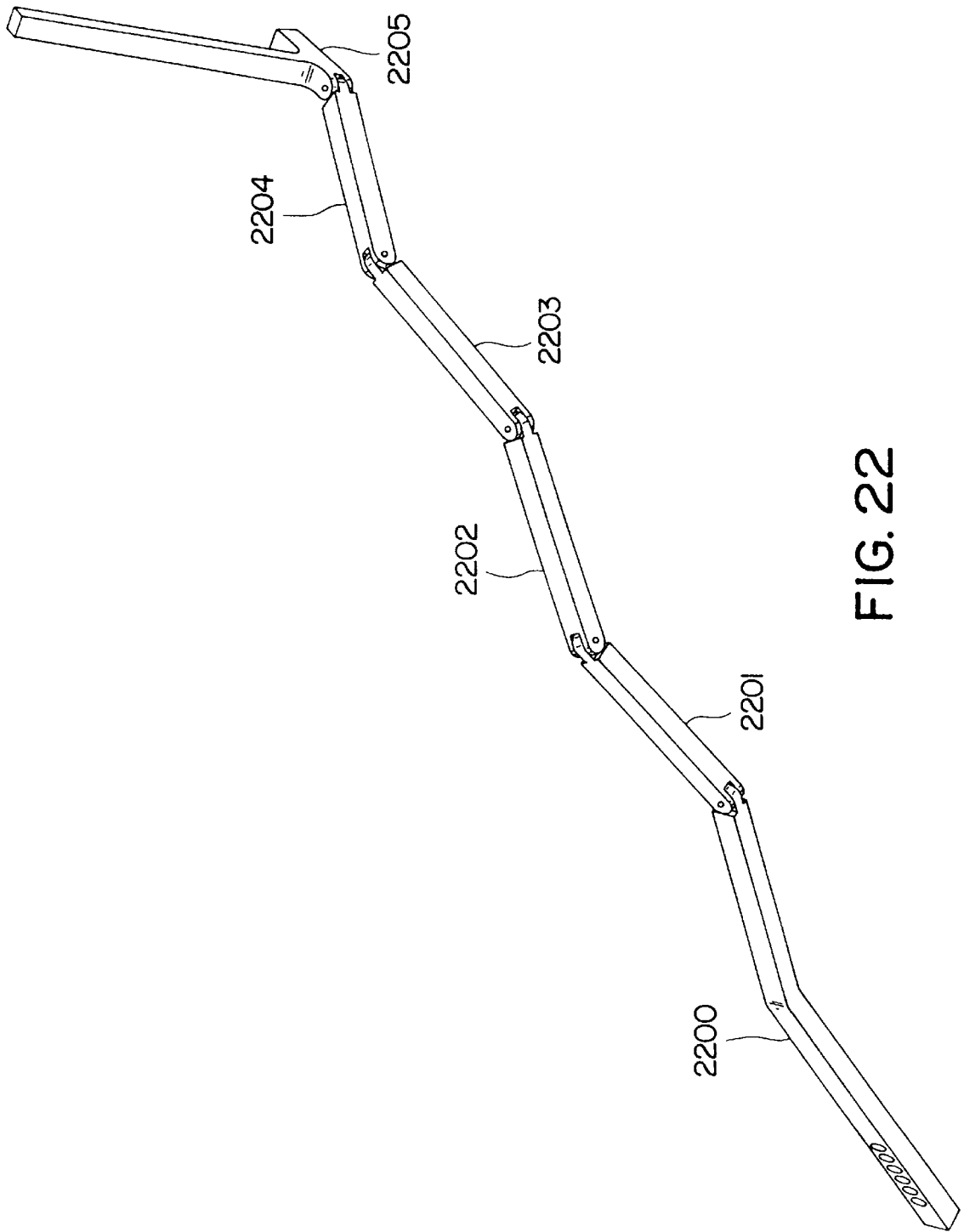
FIG. 22 is a diagrammatic illustration showing an embodiment of a simplified alternative mechanical linkage configuration for use on the right shoulder of the human body.

FIG. 22 shows a simplified version of the typical right shoulder linkage given in FIG. 12. As discussed, a resistive bend sensor can be spanned over multiple parallel-axis revolute joints in order to measure the sum of the angles across these joints. This feature allows for a reduction in the number of sensors without any corresponding loss of rotation information, since each of the "joint sets" shown in FIG. 12 can be instrumented with a single sensor. FIG. 22 replaces each of the joint sets in FIG. 12 with a single joint connecting simplified links (2200, 2201, 2202, 2203, 2204 and 2205) in order to simplify the derivation of the kinematic transformation equation across the complete right-shoulder assembly.

Note that this technique results in a loss of translational information, as it becomes no longer possible to determine the displacement vector between the proximal and distal ends of the linkage once the individual joints comprising a joint set have been lumped together in this fashion. For body-measurement applications, however, this is not a concern, as kinematic constraints provided by human-body geometry allow for the determination of the body position. For example, the joint motions that comprise a human shoulder can, to a reasonable degree of accuracy, be modeled as a ball-and-socket joint with a fixed center of rotation. This assumption, combined with a knowledge of the relative orientation between the upper torso and the humerus bone, suffices to fix both the position and orientation of the upper arm. If it ever becomes necessary to explicitly measure the actual displacement vector between the ends of the mechanical linkage in addition to the rotation information, then this can be accomplished by either (1) limiting the choice of joint sets to the trivial case where each set comprises a single revolute joint only, or (2) using a single resistive bend sensor for each revolute joint. Note that if practical, option (2) is preferred since the redundant joints are added to allow for translation between various joint set, and also to provide better conformity of the mechanical structure to the contour of the body.

FIGS. 23 to 28 show close-up views of portions of the right shoulder mechanism given in FIG. 22. They define exactly the various angles that comprise a typical right shoulder assembly. Note that in order to make the assembly best fit the body, the first angle is a fixed offset, followed by five revolute joint angles which are variable and are typically measured using resistive bend sensors. Recall, however, that any convenient goniometer as listed previously may be substituted. The frame and angle derivations for this mechanism are representative of those used in a generalized mechanical linkage assembly and are therefore given in full detail.

With any mechanical sensor assembly described here, frame A is defined as the frame attached to the first (proximal) link, and frame Z is that attached to the final (distal) link. To facilitate the derivation of the $T_{AZ}$ matrix for this mechanism, the intermediate frames a through g have been used. Frame a is identical to frame A, and frame g is identical to frame Z.

Figure 23:
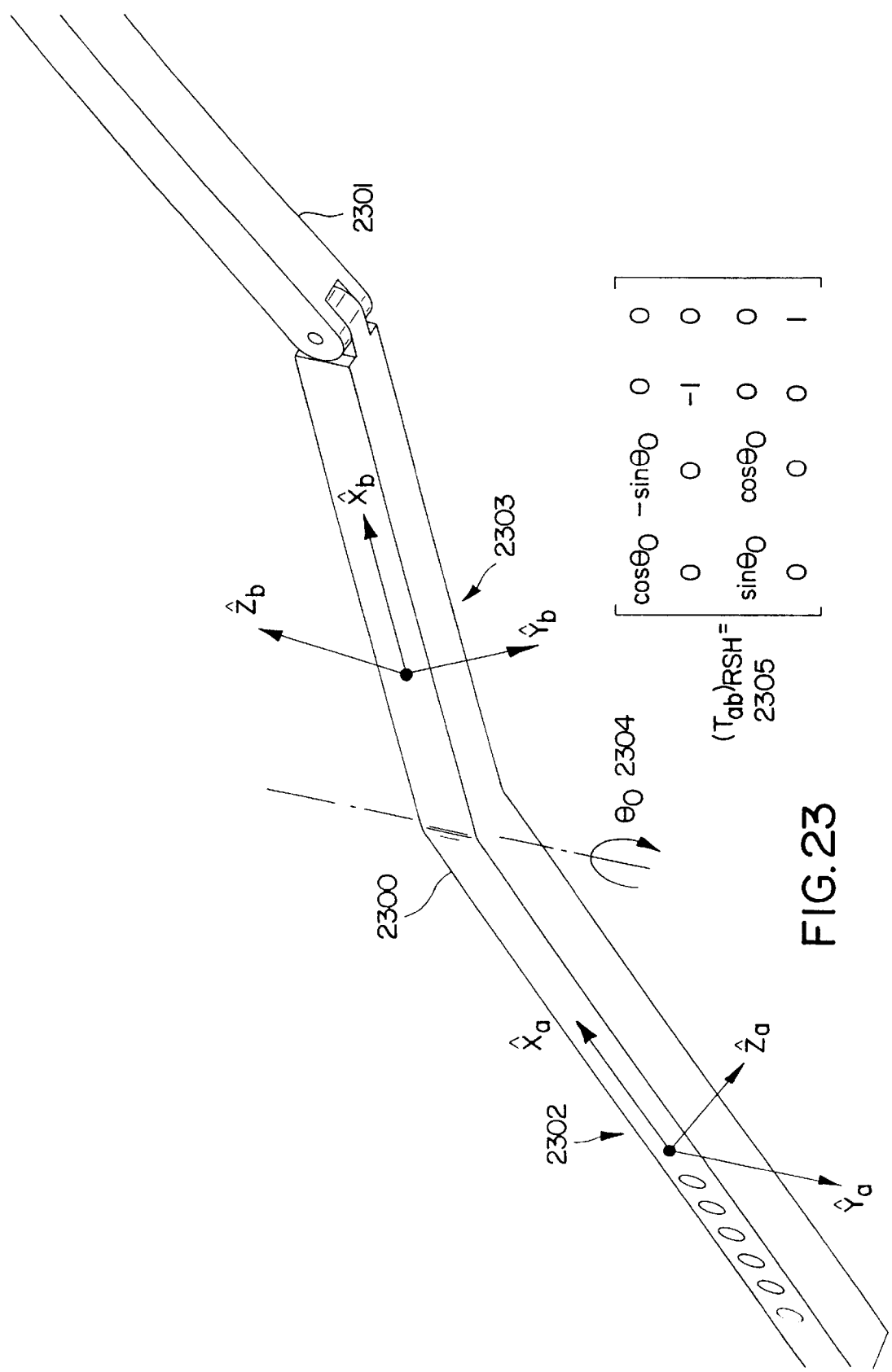
FIG. 23 is a diagrammatic illustration showing detail of a portion (link 0) of the right-shoulder mechanical linkage in FIG. 22.
Figure 24:
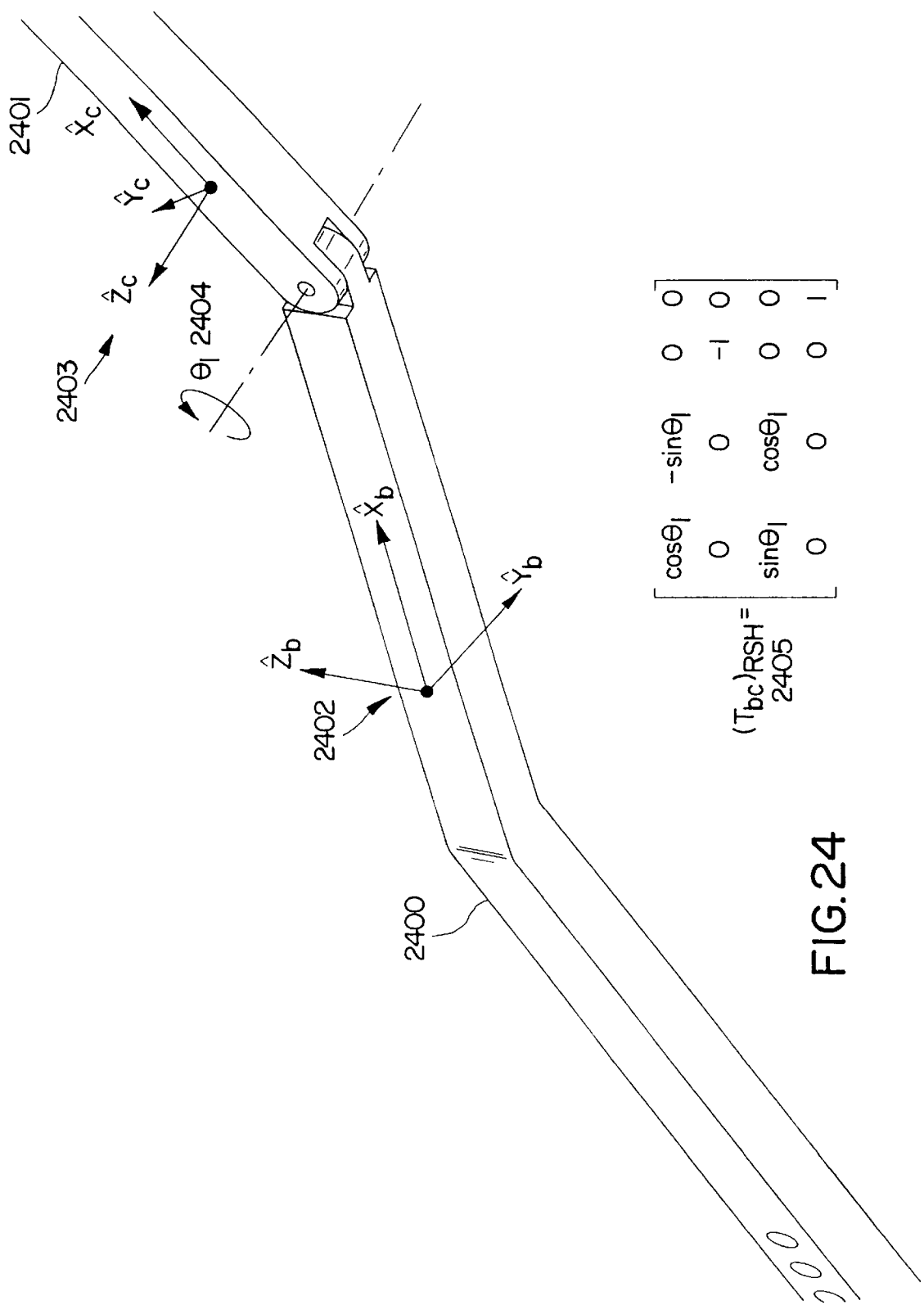
FIG. 24 is a diagrammatic illustration showing detail of a portion (links 0 and 1) of the right-shoulder mechanical linkage in FIG. 22.
Figure 25:
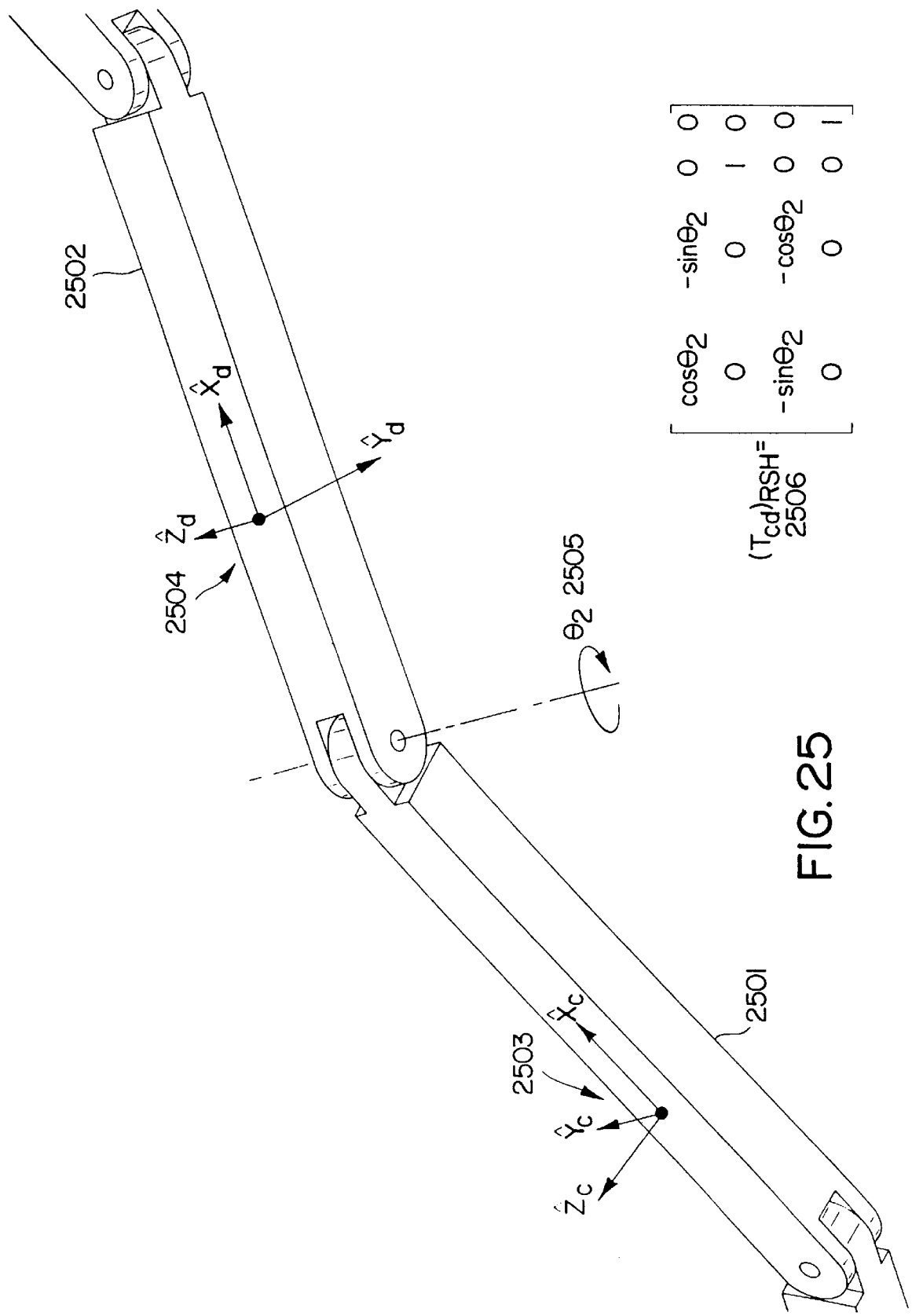
FIG. 25 is a diagrammatic illustration showing detail of a portion (links 1 and 2) of the right-shoulder mechanical linkage in FIG. 22.
Figure 26:
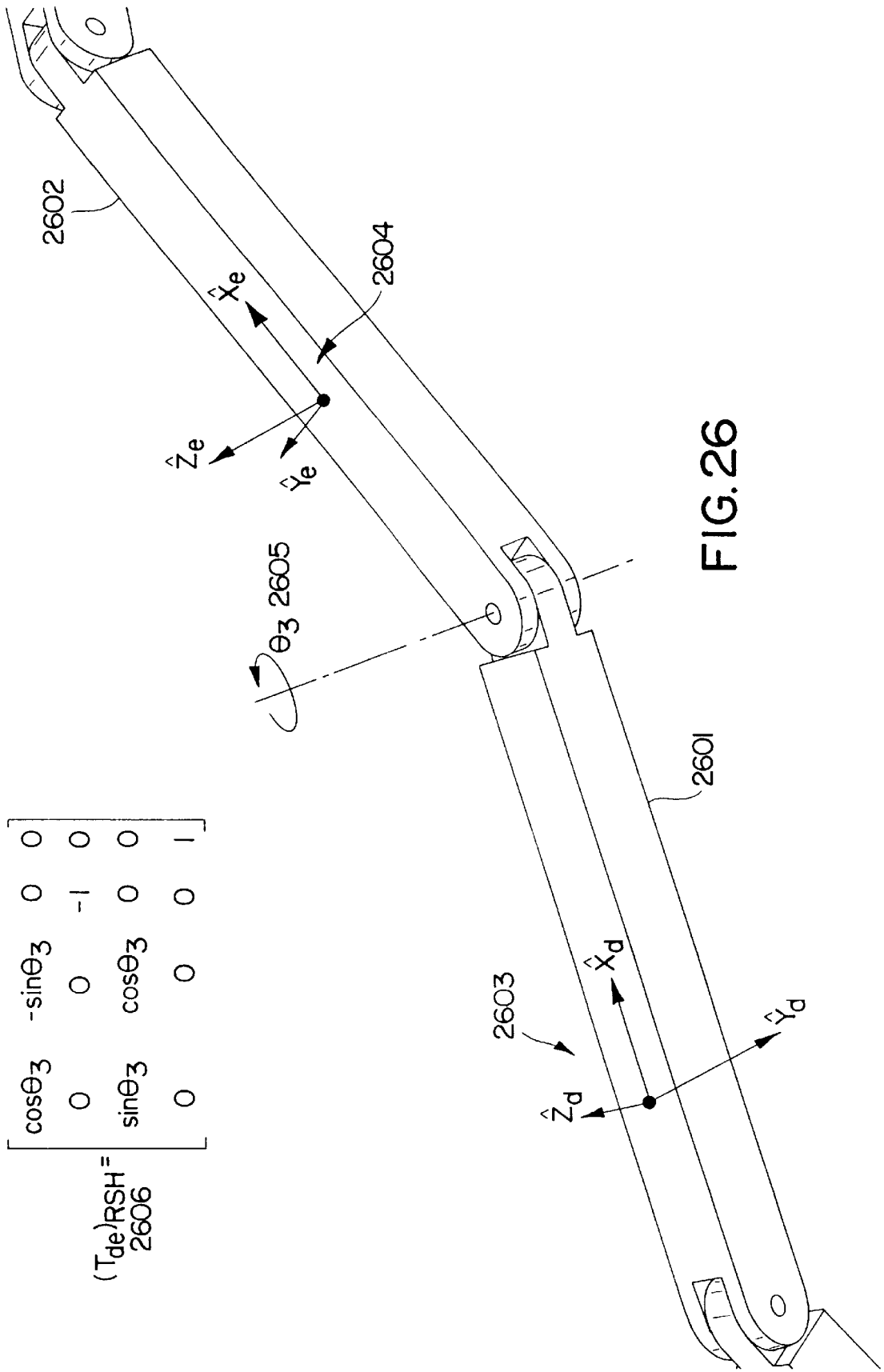
FIG. 26 is a diagrammatic illustration showing detail of a portion (links 2 and 3) of the right-shoulder mechanical linkage in FIG. 22.
Figure 27:
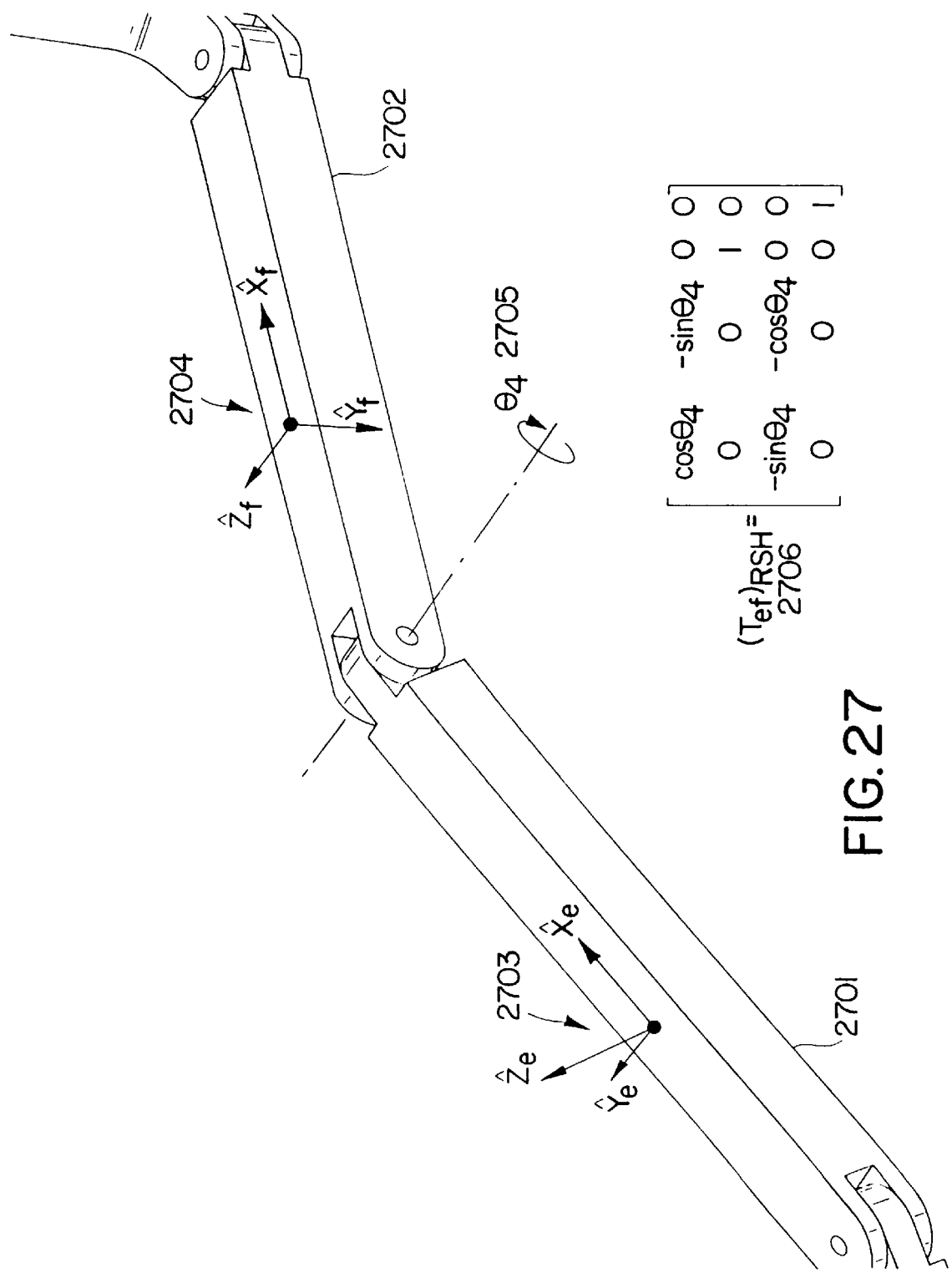
FIG. 27 is a diagrammatic illustration showing detail of a portion (links 3 and 4) of the right-shoulder mechanical linkage in FIG. 22.
Figure 28:
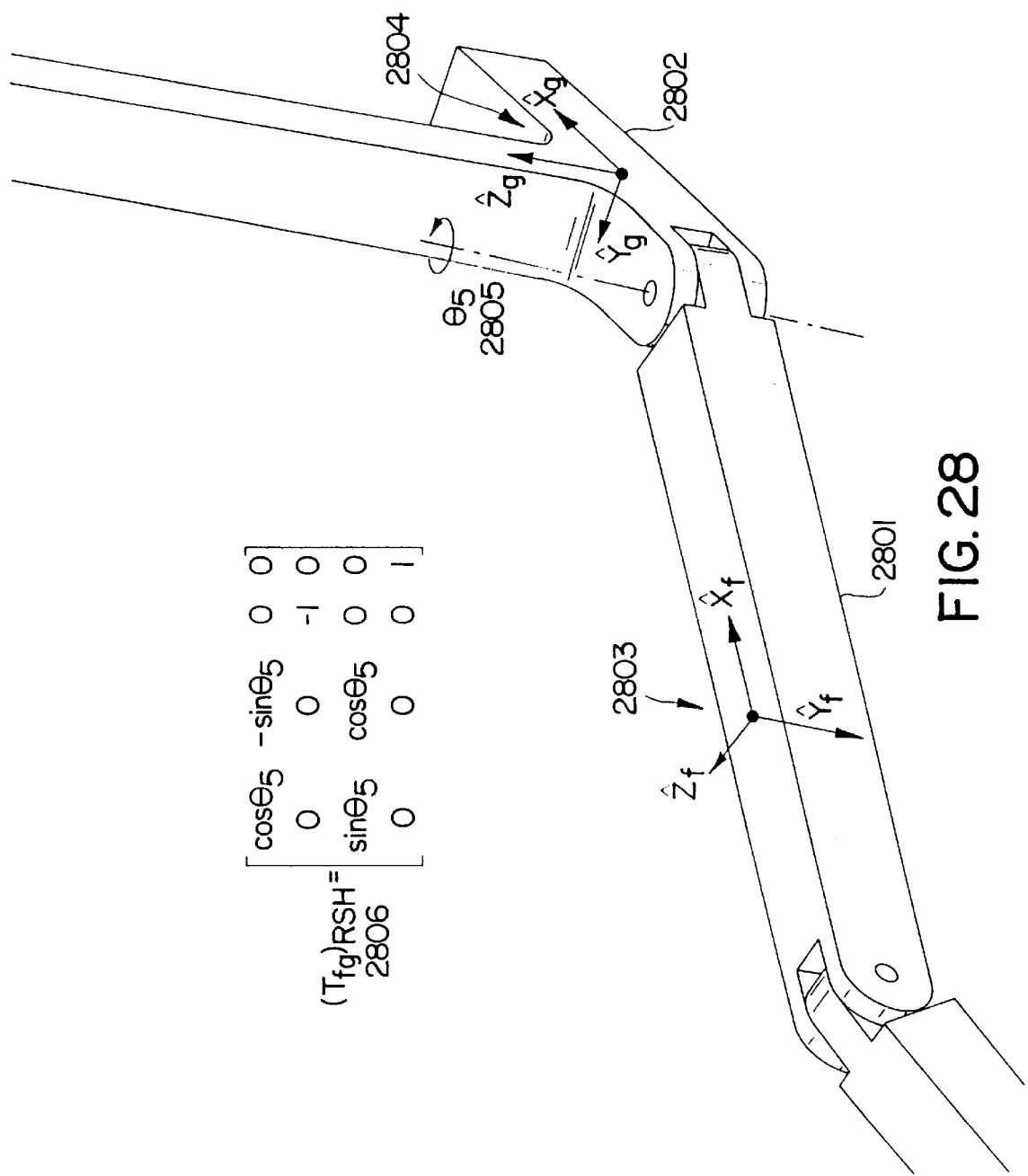
FIG. 28 is a diagrammatic illustration showing detail of a portion (links 4 and 5) of the right-shoulder mechanical linkage in FIG. 22.

We now summarize the structures illustrated in FIGS. 23 through 28. FIG. 23 shows a close-up of link 0 (2300), and is used to define $T_{ab}$ (2305) using the fixed offset angle, $q_0$ (2304). FIG. 24 shows a close-up of links 0 (2400) and 1 (2401), and is used to define $T_{bc}$ (2405) using the bend sensor angle $q_1$ (2404). FIG. 25 shows a close-up of links 1 (2501) and 2 (2502), and is used to define $T_{cd}$ (2506) using the bend sensor angle $q_2$ (2505). FIG. 27 shows a close-up of links 3 (2701) and 4 (2702), and is used to define $T_{ef}$ (2706) using the bend sensor angle $q_4$ (2705). Finally, FIG. 28 shows a close-up of links 4 (2801) and 5 (2802), and is used to define $T_{fg}$ (2806) using the bend sensor angle $q_5$ (2805).

The corresponding coordinate transformations are as follows:

$$(T_{ab})_{RSH} = \begin{bmatrix} \cos\theta_0 & -\sin\theta_0 & 0 & 0 \\ 0 & 0 & -1 & 0 \\ \sin\theta_0 & \cos\theta_0 & 0 & 0 \\ 0 & 0 & 0 & 1 \end{bmatrix}$$

$$(T_{bc})_{RSH} = \begin{bmatrix} \cos\theta_1 & -\sin\theta_1 & 0 & 0 \\ 0 & 0 & -1 & 0 \\ \sin\theta_1 & \cos\theta_1 & 0 & 0 \\ 0 & 0 & 0 & 1 \end{bmatrix}$$

$$(T_{cd})_{RSH} = \begin{bmatrix} \cos\theta_2 & -\sin\theta_2 & 0 & 0 \\ 0 & 0 & 1 & 0 \\ -\sin\theta_2 & -\cos\theta_2 & 0 & 0 \\ 0 & 0 & 0 & 1 \end{bmatrix}$$

$$(T_{de})_{RSH} = \begin{bmatrix} \cos\theta_3 & -\sin\theta_3 & 0 & 0 \\ 0 & 0 & -1 & 0 \\ \sin\theta_3 & \cos\theta_3 & 0 & 0 \\ 0 & 0 & 0 & 1 \end{bmatrix}$$

$$(T_{ef})_{RSH} = \begin{bmatrix} \cos\theta_4 & -\sin\theta_4 & 0 & 0 \\ 0 & 0 & 1 & 0 \\ -\sin\theta_4 & -\cos\theta_4 & 0 & 0 \\ 0 & 0 & 0 & 1 \end{bmatrix}$$

$$(T_{fg})_{RSH} = \begin{bmatrix} \cos\theta_5 & -\sin\theta_5 & 0 & 0 \\ 0 & 0 & -1 & 0 \\ \sin\theta_5 & \cos\theta_5 & 0 & 0 \\ 0 & 0 & 0 & 1 \end{bmatrix}$$

Once the various constituent transformation matrices have been defined and calculated, the resultant transformation across the right shoulder sensor assembly can be determined according to the equation:

$$(T_{AZ})_{RSH} = (T_{ab})_{RSH}(T_{bc})_{RSH}(T_{cd})_{RSH}(T_{de})_{RSH}(T_{ef})_{RSH}(T_{fg})_{RSH}$$

In FIG. 29, there is shown a close-up view of a typical spine plate (2901) that includes holders (2902) used to fix the first (proximal) ends of the typical right (2904) and left (2903) shoulder linkages to the body. It fits in a fabric pocket on the suit and can be held securely in place with appropriate fasteners.

Figure 30A:
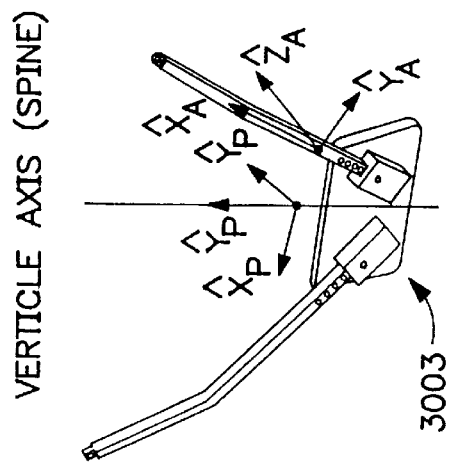
FIG. 30 is a diagrammatic illustration showing (a) right side view, (b) view perpendicular to plate, and (c) perspective view of an exemplary Spine Frames.
Figure 30C:
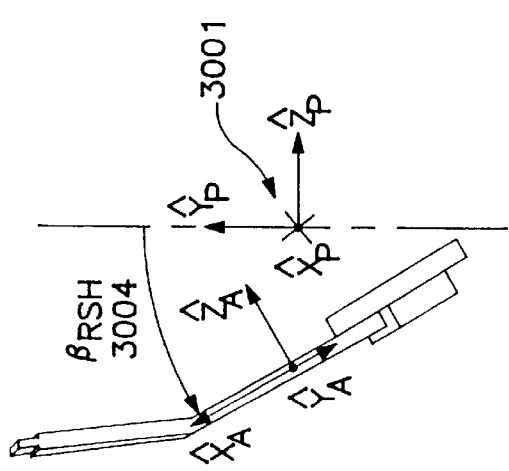
Figure 30B:
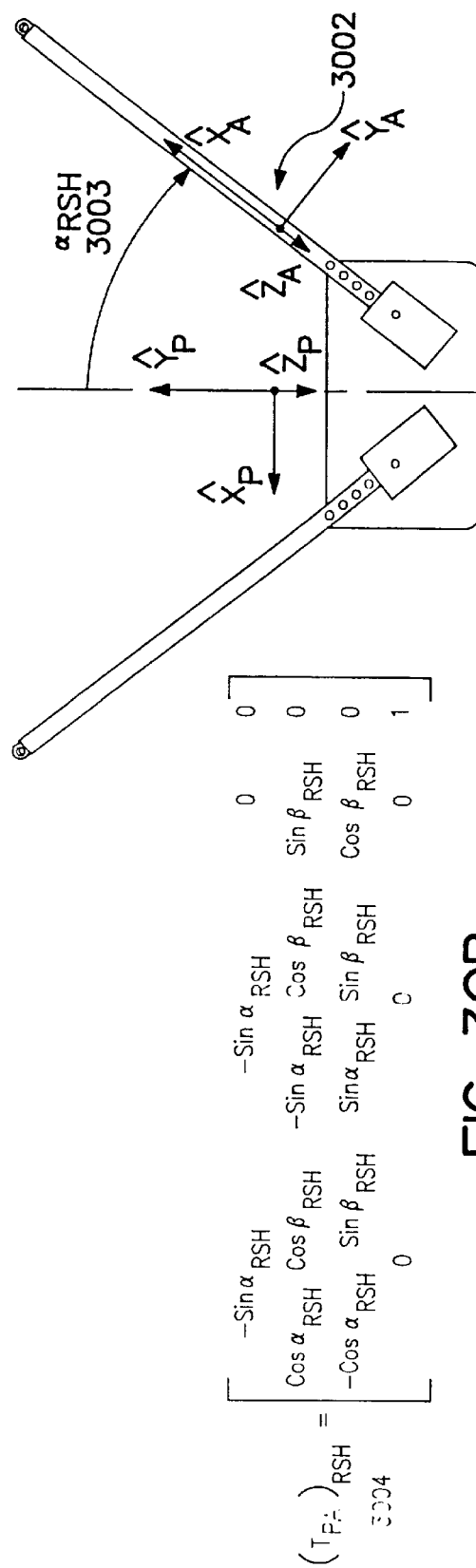

In FIG. 30, there are shown three views of the spine plate (3003) illustrated in FIG. 29. These views are used to define the $T_{PA}$ matrix (3004) that expresses the relative orientation of frame A (3002), the frame attached to the first (proximal) right shoulder link with respect to frame P (3001), the frame attached to the spine, which is in this example taken to be the proximal body part for a shoulder-angle measurement. The relative orientation of the two frames is described by two angles, $\alpha_{RSH}$ (3003) and $\beta_{RSH}$ (3004). As shown in the figure, $\beta_{RSH}$ is the angle in a right side view between the spine and the plate, and $\alpha_{RSH}$ is the angle of the first shoulder link with respect to the spine plate's vertical centerline.

Figure 31:
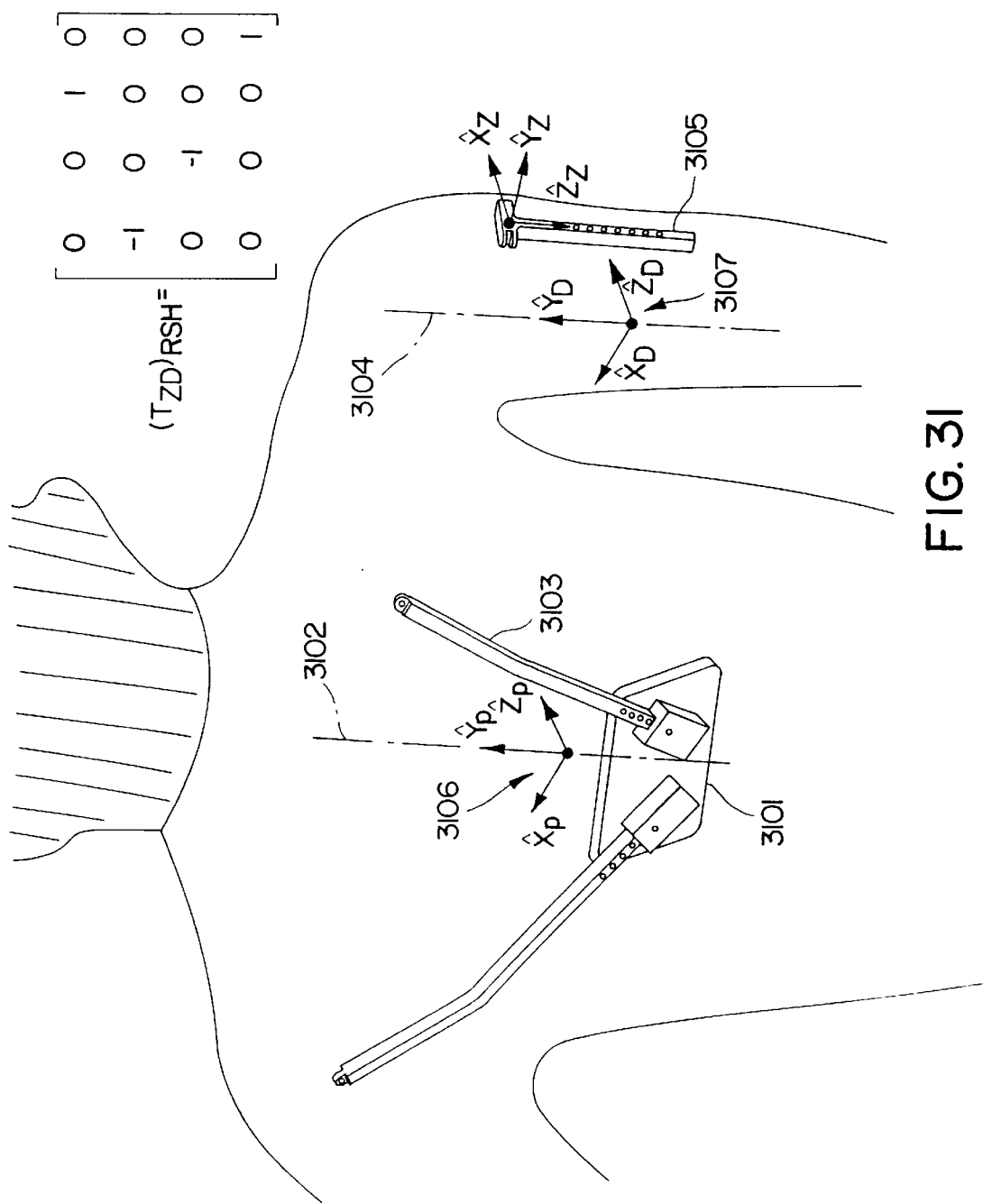
FIG. 31 is a diagrammatic illustration showing spine and arm frames relative to a human body.

FIG. 31 shows the spine plate (3101) and final (distal) right shoulder linkage (3105) on the body. For any particular body part and mechanical assembly, a "zero position" must be defined. For the typical right shoulder assembly, this has been defined as the configuration with the arm at the side and the palm facing inward. (Note that this configuration is not the same as the so called "anatomical position", which has the palm facing forward.)

In the zero position, the frame P attached to the proximal body part (3106) and the frame D attached to the distal body part (3107) are, by definition, exactly aligned. When the frames are aligned, a (0,0,0) Euler angle triad is used to describe the orientation between the two body part frames, so the term "zero position" is a natural one.

Once frames P and D have been aligned in this way, the definition of $T_{ZD}$ follows. To simplify system calibration, it is assumed that the distal link and distal body part are aligned with each other. The matrix $T_{ZD}$ is therefore a simple one. For example, for the typical right shoulder assembly the matrix $T_{ZD}$ given by the expression:

$$(T_{ZD})_{RSH} = \begin{bmatrix} 0 & 0 & 1 & 0 \\ -1 & 0 & 0 & 0 \\ 0 & -1 & 0 & 0 \\ 0 & 0 & 0 & 1 \end{bmatrix}$$

Figure 32:
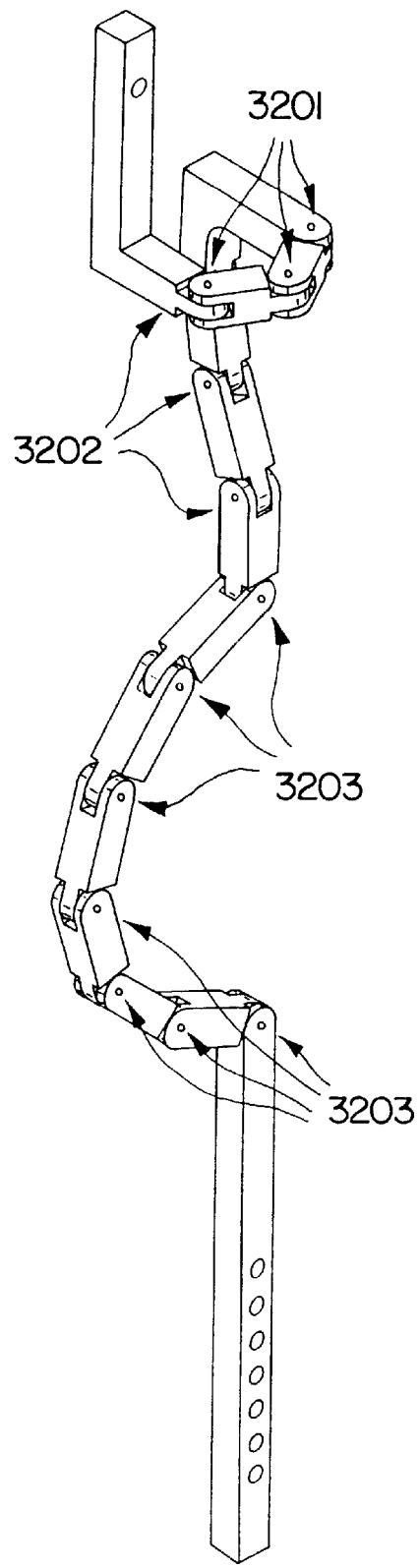
FIG. 32 is a diagrammatic illustration showing an exemplary arrangement of linkages or joints for a right hip linkage assembly.

FIG. 32 shows the arrangement of the linkages for a typical right hip linkage assembly. As in FIG. 12, which shows the five "joint sets" for the right shoulder assembly, the joints for this typical hip linkage can be collected into three joint sets (3201, 3202 and 3203). All discussions of joint sets for the right shoulder mechanism apply equally to that for the right hip.

(3406) body parts are defined to be exactly aligned. For the typical right hip, this was chosen as the natural standing position with the foot facing forward. As with the right shoulder, the distal hip link and the second body part (the femur) are assumed to be aligned. From this choice of zero position aligning frames P and D, transformation $T_{ZD}$ (3407) must be:

$$(T_{ZD})_{RHIP} = \begin{bmatrix} 0 & -1 & 0 & 0 \\ 0 & 0 & 1 & 0 \\ -1 & 0 & 0 & 0 \\ 0 & 0 & 0 & 1 \end{bmatrix}$$

Figure 35:
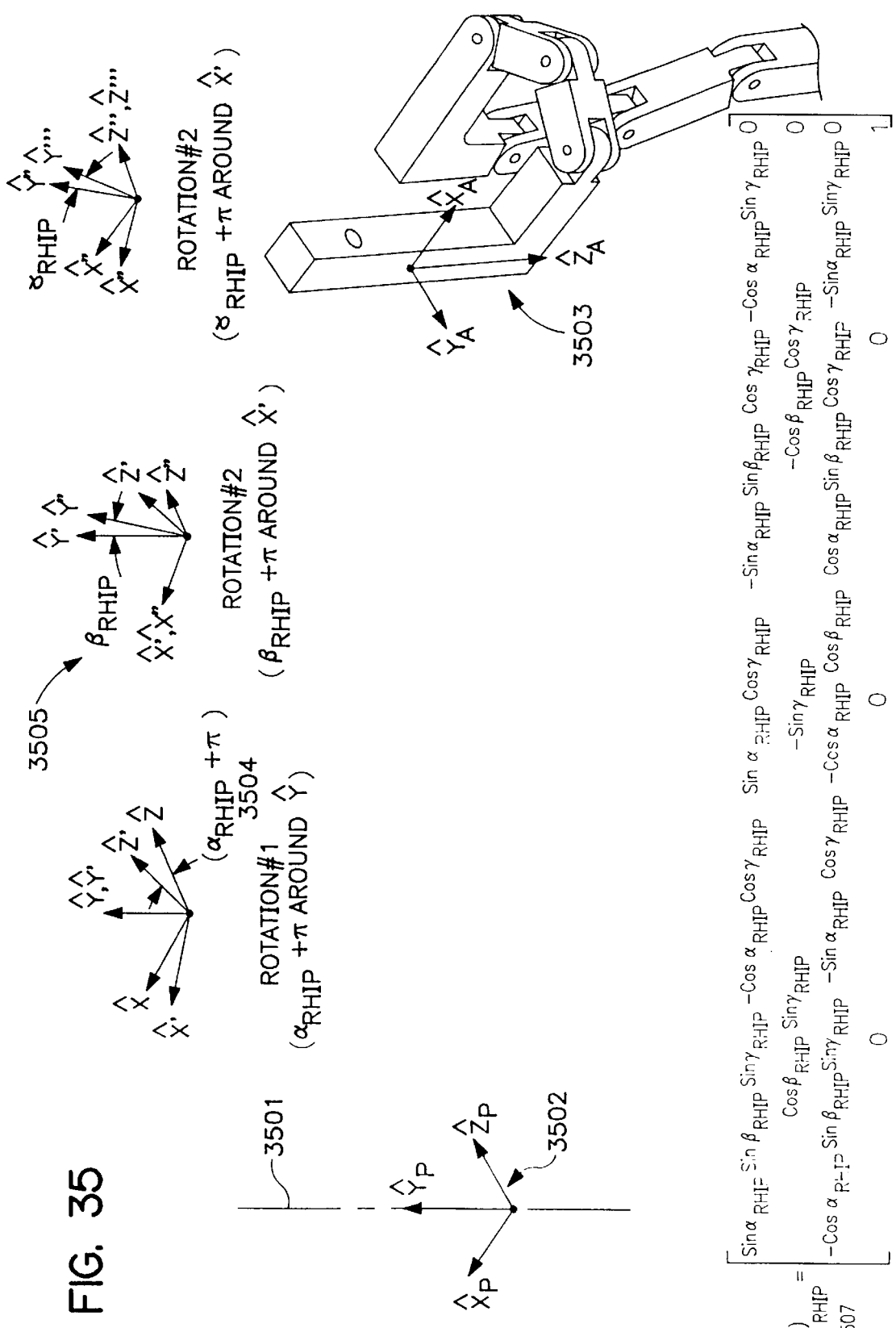
FIG. 35 is a diagrammatic illustration showing an exemplary hip plate frame mechanical assembly on a human body.

FIG. 35 shows hip plate frames including a close-up of the top of the typical right hip assembly, and includes the frames and angles needed to define $T_{PA}$ (3507) for this mechanism. Unlike $T_{PA}$ for the typical right shoulder, which is described by two Euler-angle parameters, the matrix for the right hip assembly requires three: $\alpha_{RHIP}$, $\beta_{RHIP}$, and $\gamma_{RHIP}$ (3504, 3505 and 3506). Recall that frame P (3502) is defined as the frame attached to the proximal body part, and frame A (3503) is defined as the frame attached to the first (proximal) link in the hip assembly. Before these three angles are applied to frame A, it is initially aligned with frame P. From this starting orientation, Frame A is first rotated about the spine axis by the angle $\pi+\alpha_{RHIP}$, then about its outward normal by the angle $\beta_{RHIP}$, then about its upper outside edge by the angle $\gamma_{RHIP}$. FIG. 35 shows the final orientation of frame A, along with the exact definitions of the three rotations described above. Based on these rotations, the resulting $T_{PA}$ is:

$$(T_{PA})_{RHIP} = \begin{bmatrix} \sin\alpha_{RHIP}\sin\beta_{RHIP}\sin\gamma_{RHIP} - \cos\alpha_{RHIP}\cos\gamma_{RHIP} & \sin\alpha_{RHIP}\cos\beta_{RHIP} & -\sin\alpha_{RHIP}\sin\beta_{RHIP}\cos\gamma_{RHIP} - \cos\alpha_{RHIP}\sin\gamma_{RHIP} & 0 \\ \cos\beta_{RHIP}\sin\gamma_{RHIP} & -\sin\beta_{RHIP} & -\cos\beta_{RHIP}\cos\gamma_{RHIP} & 0 \\ -\cos\alpha_{RHIP}\sin\beta_{RHIP}\sin\gamma_{RHIP} - \sin\alpha_{RHIP}\cos\gamma_{RHIP} & -\cos\alpha_{RHIP}\cos\beta_{RHIP} & \cos\alpha_{RHIP}\sin\beta_{RHIP}\cos\gamma_{RHIP} - \sin\alpha_{RHIP}\sin\gamma_{RHIP} & 0 \\ 0 & 0 & 0 & 1 \end{bmatrix}$$

Figure 33:
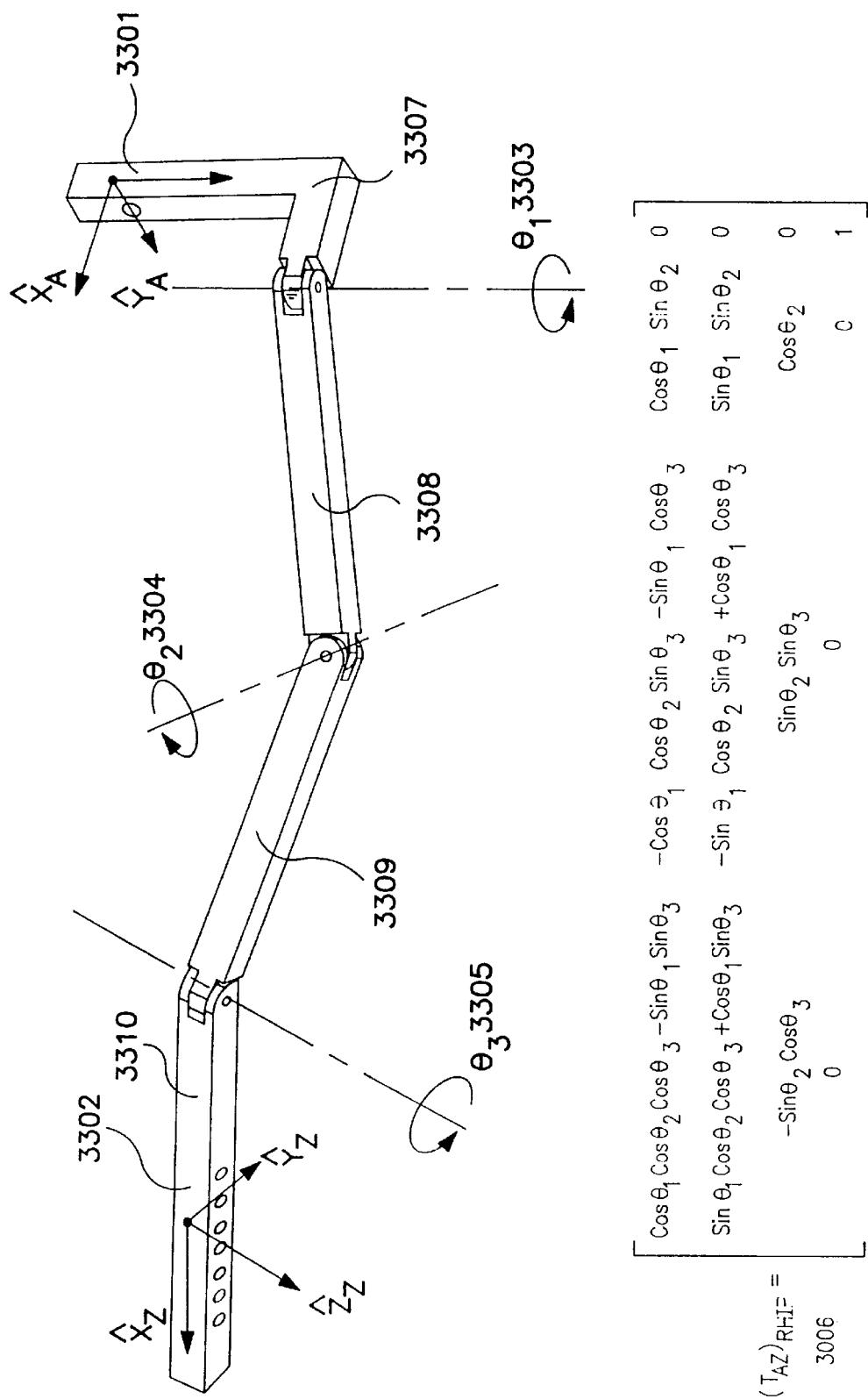
FIG. 33 is a diagrammatic illustration showing an exemplary simplified alternative right hip linkage assembly.

FIG. 33 shows the four-link (3307, 3308, 3309 and 3310) kinematic equivalent of the right hip assembly, which is obtained by replacing each hip joint set by a single revolute joint. The frame attached to the first link, frame A (3301), is shown, as is the frame attached to the last link, frame Z (3302). The axes and directions of the three hip bend sensor angles (3303, 3304 and 3305) are also shown; these angles are all zero when the hip assembly is fully straight. The resulting matrix (3306) expressing the relative orientation of the last hip link with respect to the first hip link is:

$$(T_{AZ})_{RHIP} = \begin{bmatrix} \cos\theta_1\cos\theta_2\cos\theta_3 - \sin\theta_1\sin\theta_3 & -\cos\theta_1\cos\theta_2\sin\theta_3 - \sin\theta_1\cos\theta_3 & \cos\theta_1\sin\theta_2 & 0 \\ \sin\theta_1\cos\theta_2\cos\theta_3 + \cos\theta_1\sin\theta_3 & -\sin\theta_1\cos\theta_2\sin\theta_3 + \cos\theta_1\cos\theta_3 & \sin\theta_1\sin\theta_2 & 0 \\ -\sin\theta_2\cos\theta_3 & \sin\theta_2\sin\theta_3 & \cos\theta_2 & 0 \\ 0 & 0 & 0 & 1 \end{bmatrix}$$

Figure 34:
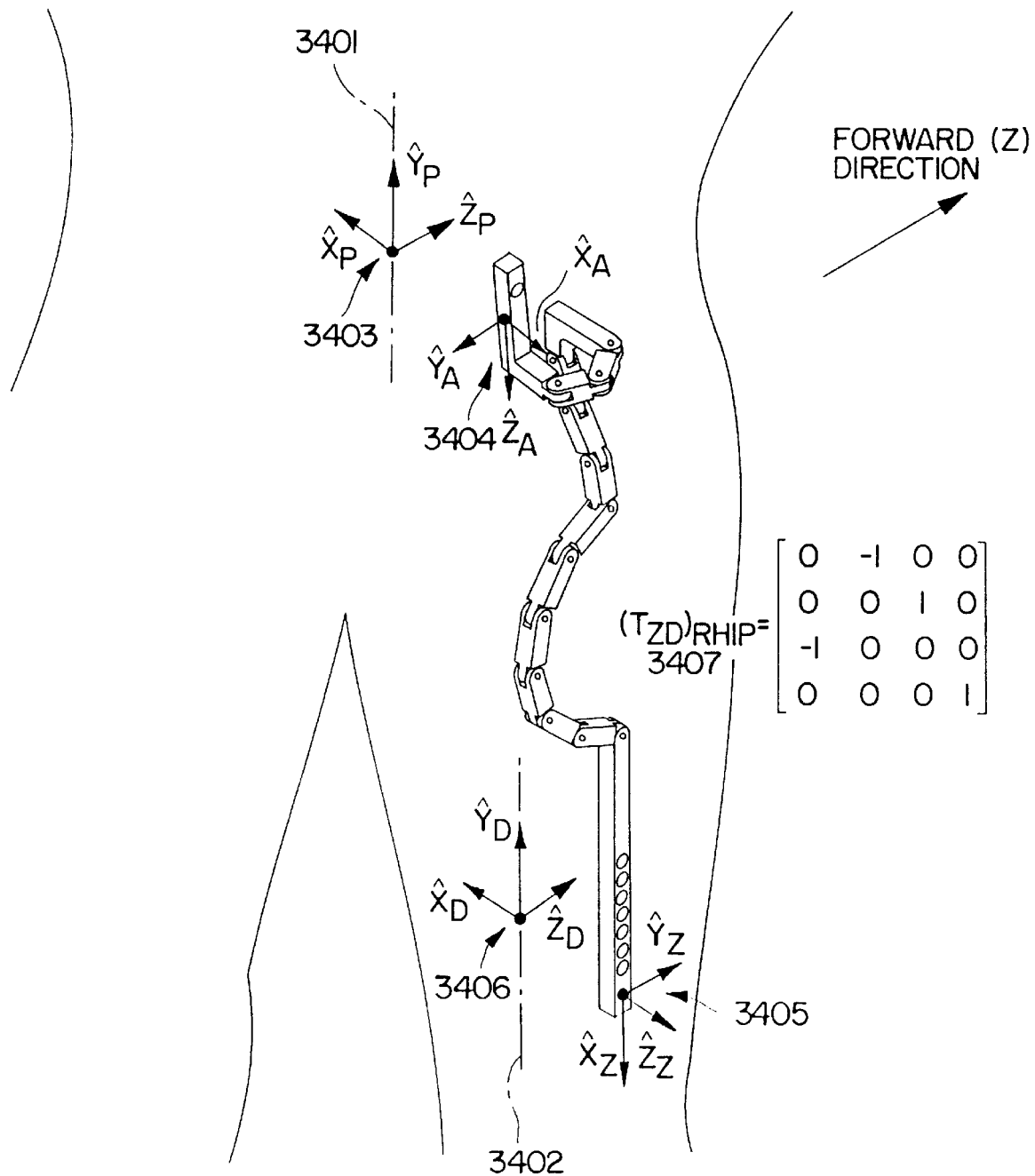
FIG. 34 is a diagrammatic illustration showing an exemplary spine and leg frame mechanical assembly on a human body.
Figure 36:
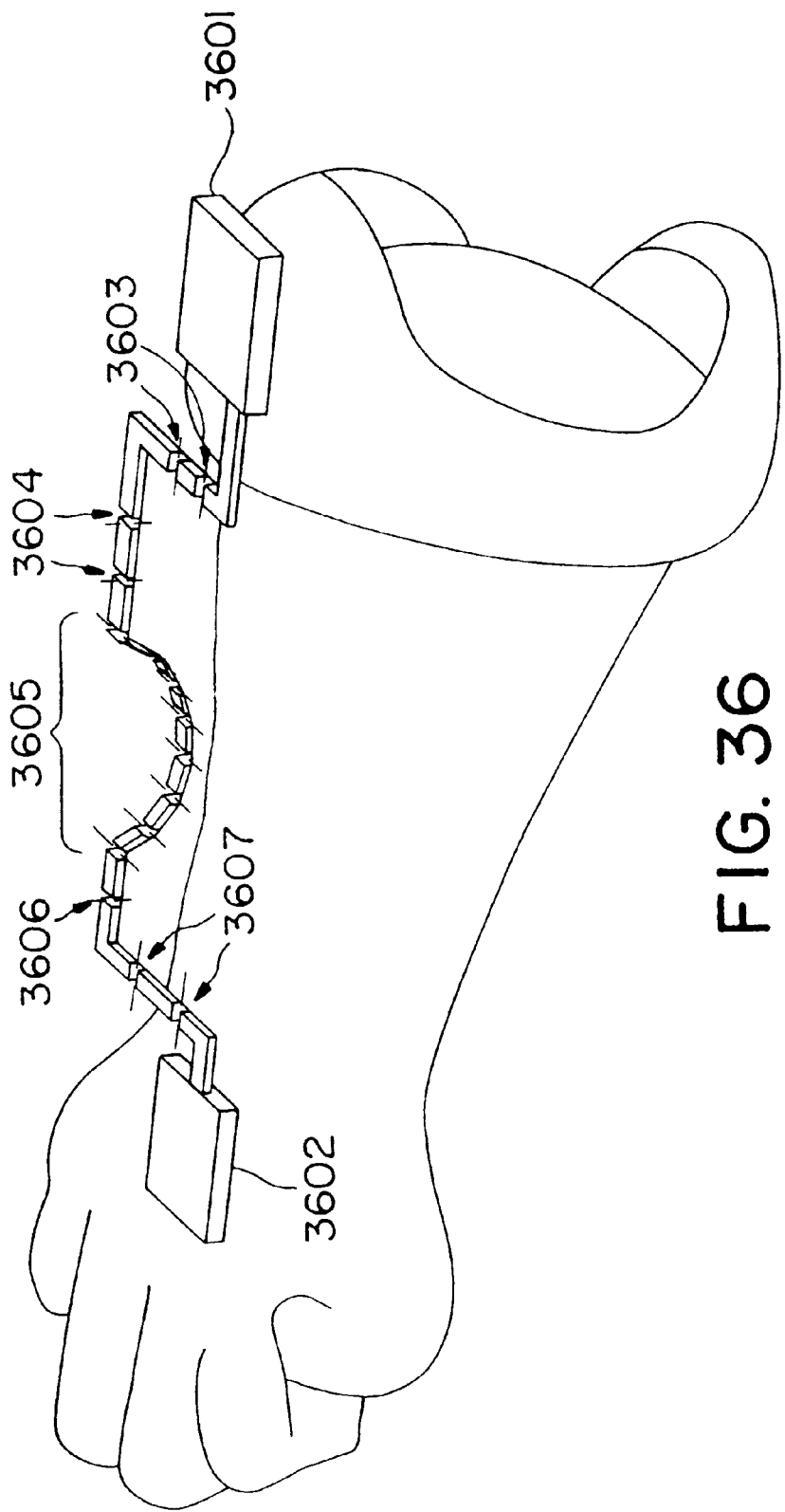
FIG. 36 is a diagrammatic illustration showing an exemplary wrist and forearm assembly in a configuration appropriate for measuring the bending and rotation of the wrist and forearm.

FIG. 34 shows the typical right hip mechanical assembly on the body. The linkage endpoint fixation method is not shown, but is functionally equivalent to that used for the typical right shoulder, as shown in FIGS. 20 and 21. As with the right shoulder, a "zero position" must be selected at which the frames attached to the proximal (3403) and distal FIG. 36 shows a typical arrangement of linkage elements into a mechanical sensing assembly, in a configuration appropriate for measuring the bending and rotation of the wrist and forearm. Based on the "joint set" notation introduced in the right shoulder and right hip assemblies, this configuration is characterized as having five joints sets (3603, 3604, 3605, 3606 and 3607) and would require five resistive bend sensors. The proximal end of the assembly is fixed to a fastening device (3601) located just below the elbow, and the distal end of the assembly is fixed to a fastening device (3602) located on the hand.

In FIGS. 37 to 40 are depicted a number of different embodiments of hinge sensors, which find applicability for use in the revolute joints of the linkage-based sensing devices. The hinge sensors of FIGS. 37 to 40 may be substituted at the various joints, as appropriate for a specific design.

In FIG. 37 a number of related, but different embodiments of hinge sensors are depicted. In the different embodiments, the sensor is capable of passing through the axis of the joint or generally bows away from the axis of the joint. In FIG. 37A, the sensor is shown passing through the axis of the joint. The hinge 3700 has an external yoke 3701 and an internal yoke 3702 in mating relationship to form an "open" hinge. Pins 3703 and 3704 connect yokes 3701 and 3702 and define the rotational axis of the hinge 3700. The sensor 3705 is rigidly affixed at its ends to the inner surfaces 3706 and 3707 of yokes 3701 and 3702, respectively. Links 3708 and 3709, shown fragmented, extend from yokes 3701 and 3702, respectively. While the embodiment is depicted with the sensor rigidly affixed to the internal surfaces of the yokes, one or both of the sensor ends can be guided to move relative to the yoke.

Figure 37A:
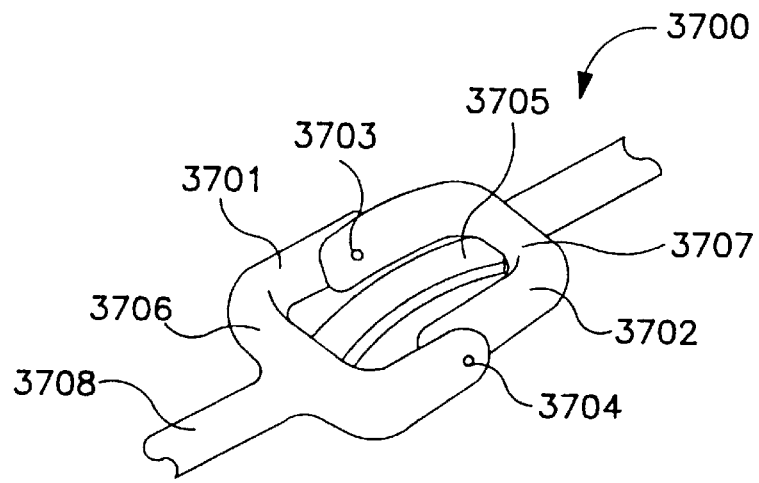
FIGS. 37A–37I are diagrammatic illustrations showing a number of different embodiments of revolute joint sensors.
Figure 37B:
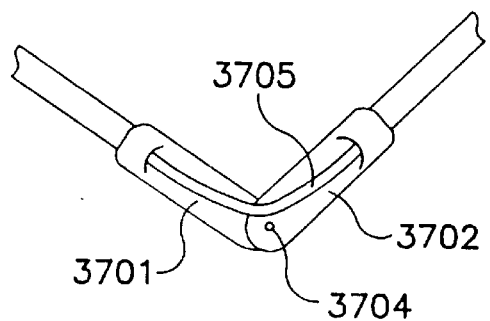
Figure 37C:
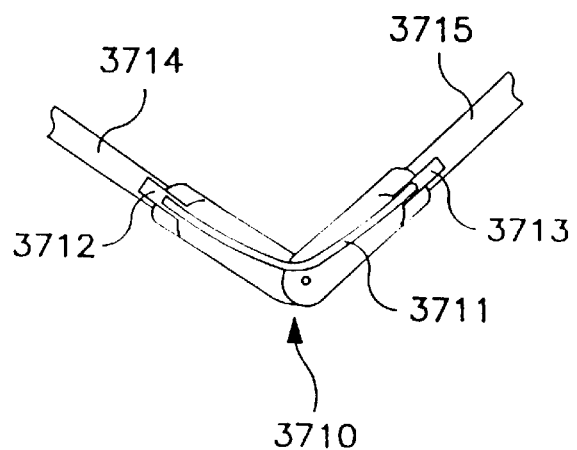

In FIG. 37B is shown a side cross-sectional view of FIG. 37A, showing the hinge 3700 with the sensor 3705 passing through the hinge axis and having its ends affixed to the yokes. In FIG. 37C is shown a side cross-sectional view, where a hinge 3710 comparable to the hinge of FIG. 37A is shown, with sensor 3711 having each of its ends in channels 3712 and 3713, respectively. Channels 3712 and 3713 extend into links 3714 and 3715, respectively. With movable ends, the sensor is able to position itself to assume a curve of low resistive force.

Figure 37D:
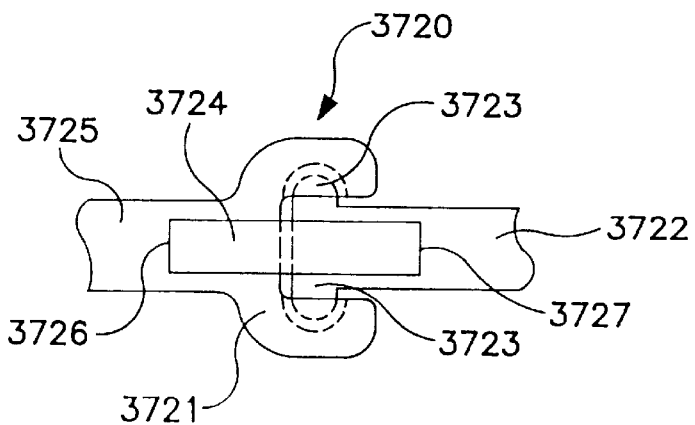
Figure 37E:
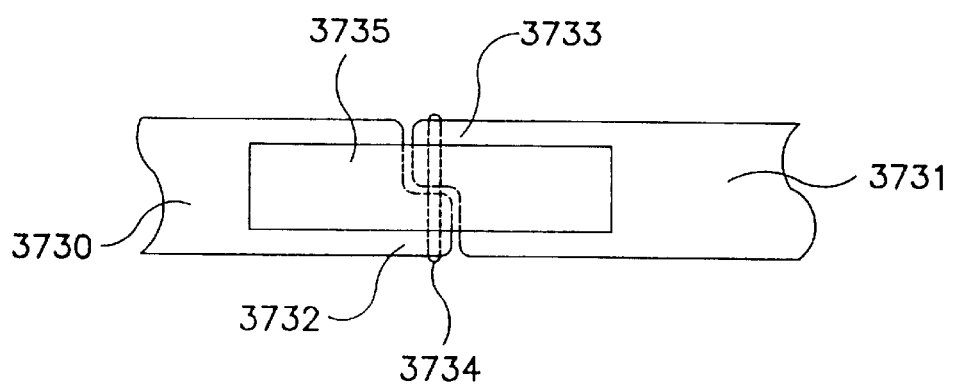

In FIG. 37D is depicted a "closed" hinge 3720, formed by external yoke 3721, attached to link 3725, in conjunction with link 3722. Link 3722 has protuberances 3723 on opposite sides of the link 3722, which protuberances extend into concavities in yoke 3721, thereby forming a hinge. The sensor 3724 is affixed at end 3726 to yoke 3721 and at end 3727 to link 3722. An alternate hinge structure is shown in FIG. 37E, where the ends of the links 3730 and 3731 have mating L-shaped ends 3732 and 3733, respectively. Pin 3734 extends through the L-shaped ends 3732 and 3733 to define the hinge. The sensor 3735 is placed over the links 3730 and 3731 extending over the pin 3734, with the sensor ends affixed to the links 3730 and 3731, by means such as clips, glue or other convenient fastening means. While the embodiments in FIGS. 37D and 37E are depicted with the sensor rigidly affixed to the internal surfaces of the yokes, one or both of the sensor ends can be guided to move relative to the yoke.

Figure 37F:
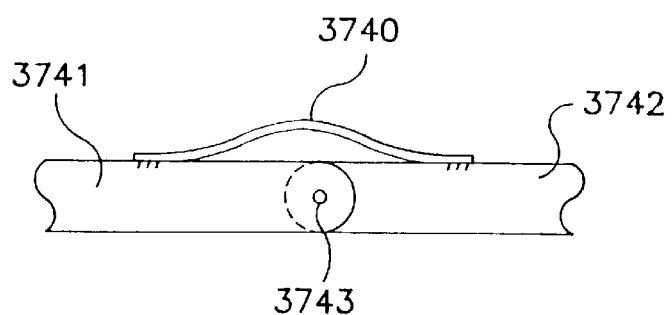
Figure 37G:
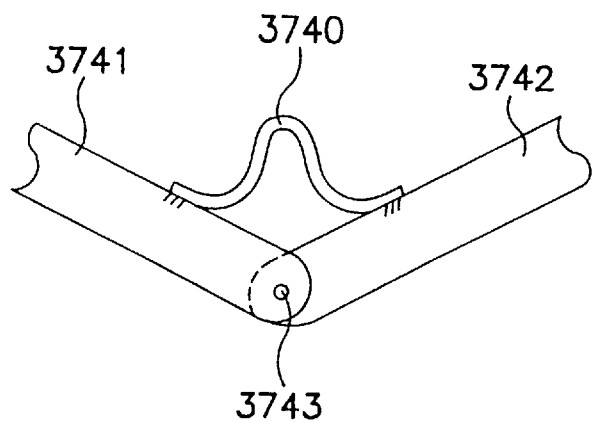
Figure 37H:
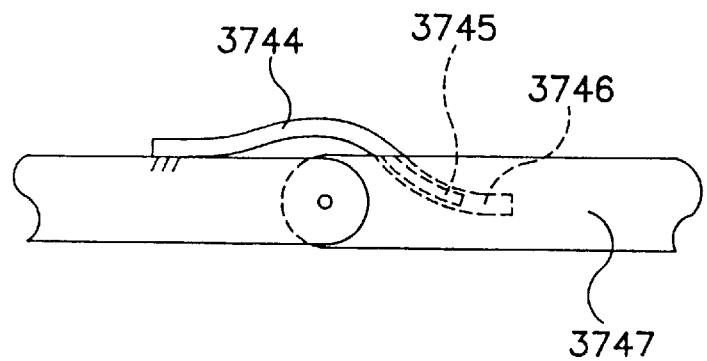
Figure 37I:
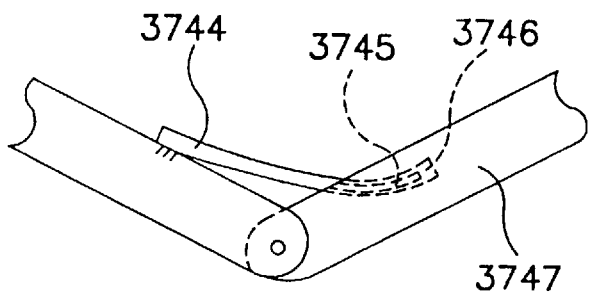

In FIG. 37F an exemplary cross-section of both FIGS. 37D and 37E is shown, wherein the sensor 3740 is shown affixed at its ends to links 3741 and 3742, to bow around the axis 3743. Links 3741 and 3742 are shown aligned. In FIG. 37G, the links 3741 and 3742 are shown unaligned, with sensor 3740 bowing a greater distance away from axis 3743. FIGS. 37H and 37I provide exemplary cross-sections of both FIGS. 37D and 37E, wherein the sensor 3744 has at least one of its ends 3745 able to slide in a channel 3746. Channel 3756 extend into link 3747. With at least one movable end, the sensor is able to position itself to assume a curve of low resistive force.

Figure 38A:
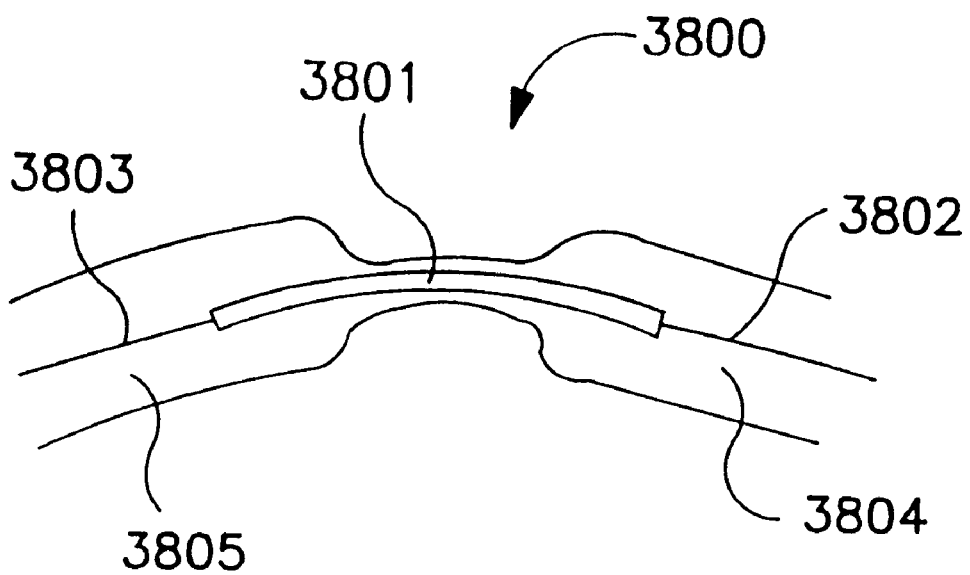
FIG. 38 is a diagrammatic illustration showing a flex sensor in a "living hinge" joint structure.
Figure 38B:
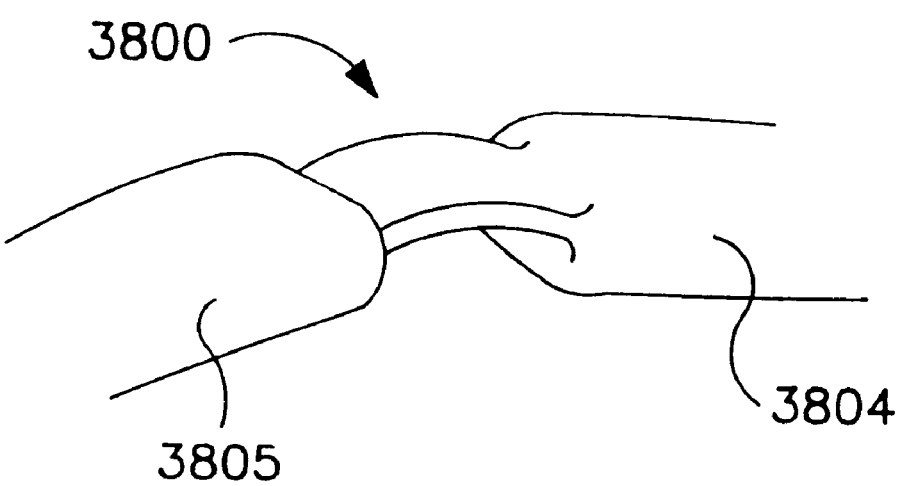

FIG. 38 provides a flex-sensing goniometer 3801 (such as the variable strain-sensing goniometers disclosed in U.S. Pat. Nos. 5,047,952 and 5,280,265 by Kramer, et al.) housed in a flexible "living" hinge structure 3800. Other flex-sensing goniometer technologies and designs, such as a fiber-optic flex sensor, may also be housed in the living hinge structure. FIG. 38A provides a cross-sectional view while FIG. 38B provides a perspective view. The electrical connections 3802 and 3803 for the goniometer are incorporated in links 3804 and 3805. In this embodiment, 3802 is the electrical connection to goniometer 3801, while 3803 is an electrical connection which passes electrically unaltered through goniometer 3801 and provides the connection for a second goniometer (not shown) at another portion of link 3805. Such electrical connections may take the form of wires, metal traces, conductive polymers, conductive inks, or other such electrically conductive paths. Constructed as such, all goniometers and electrical connections can be housed inside the link-joint structure. The goniometer with its electrical connections can be placed inside the link-joint structure in a variety of ways, including being molded into the structure. Printed circuit techniques, including etching, deposition, and other techniques, which are well known in the electronics industry, may be employed to fabricate such goniometers and their associated electrical connections.

The flex-sensing goniometer may be positioned inside the flexible hinge. Typical hinge materials are plastics and metals which can endure a large number of bend cycles without becoming mechanically damaged. As shown in the cross-section view of FIG. 38A, preferably the goniometer is positioned such that its neutral bend axis is aligned with the neutral bend axis of the flex hinge. The goniometer can lie totally within the hinge material or be only partially covered. The goniometer itself can also be the flex hinge, providing both the angle measurement as well as the material structure of the hinge.

Figure 39A:
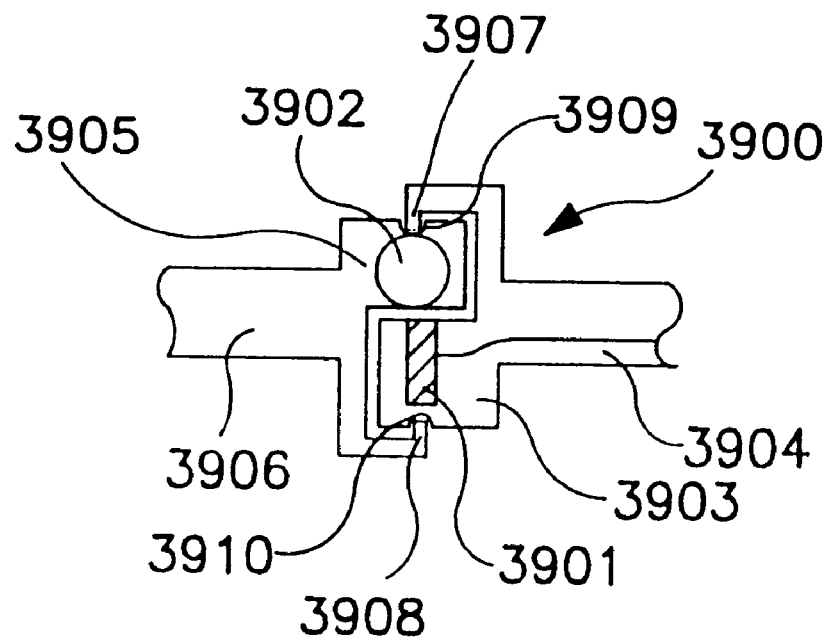
FIGS. 39A and 39B are diagrammatic illustrations showing a joint housing a Hall-effect sensor.
Figure 39B:
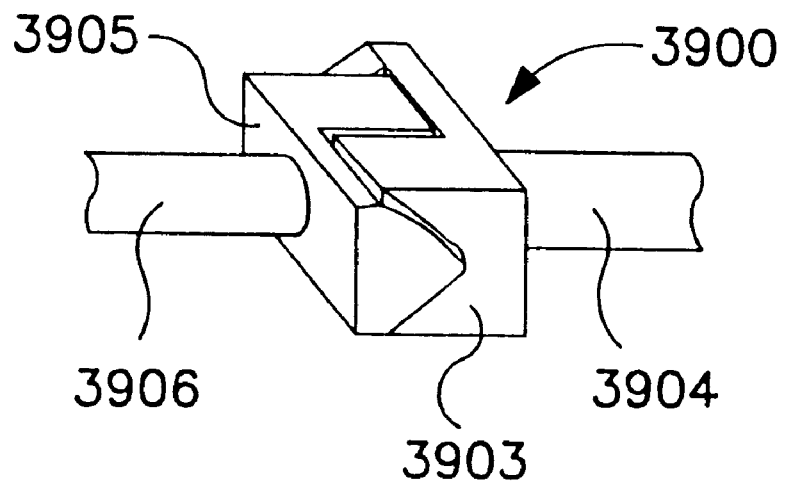

In one embodiment, as shown in FIGS. 39A and 39B, a joint 3900 houses a Hall effect goniometer comprising a Hall effect sensor 3901 and magnet 3902, which goniometer is employed at the joint to measure the angle between links 3904 and 3906. Other orientations of the sensor and magnet may be employed to improve the structural profile of the sensor, although the depicted embodiment maximizes the range of the sensor. The two mating parts 3903 and 3905 of the joint are substanitally mirror images, each one having a pin, 3907 and 3908, which sits in a groove, 3909 and 510, respectively, defining an axis of joint rotation. The Hall effect sensor 3901 is located in the part of the joint 3903 at the end of link 3904, while the magnet 3902 is located in the part 3905 at the end of link 3906. Such Hall effect goniometers may be employed for measuring the angles at any joint between associated links.

Figure 40A:
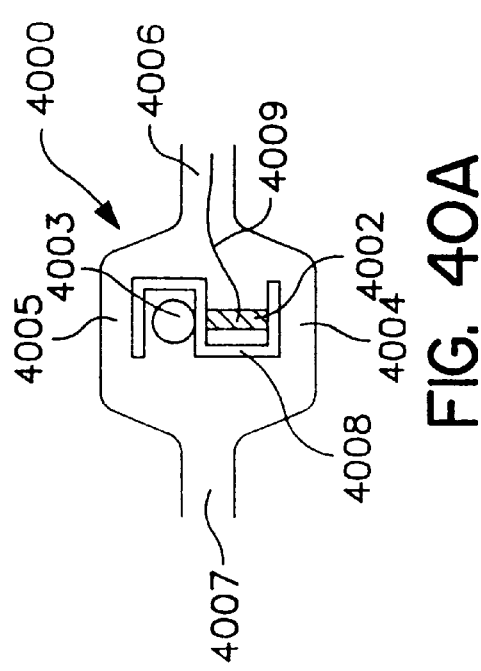
FIGS. 40A and 40B are diagrammatic illustrations showing a Hall-effect sensor in a "living hinge."
Figure 40B:
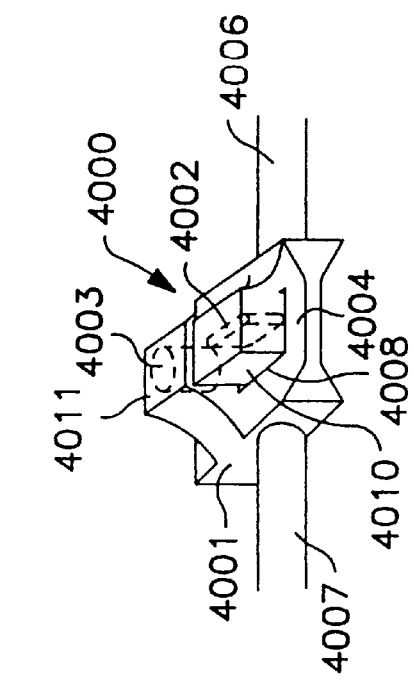

Alternatively, as shown in FIGS. 40A and 40B, a joint 4000 with a flexible hinge 4001 is used, which can be molded to the appropriate geometry. A Hall effect goniometer comprising sensor 4002 and magnet 4003 is employed to measure the angle of the joint 4000. The Hall effect goniometer components 4002 and 4003 are positioned to move relative to each other due to the flexibility of regions 4004 and 4005. Sensor 4002 follows the movement of link 4006 in fixed alignment. Similarly, magnet 4003 follows the movement of link 4007 in fixed alignment. Channel 4008 separates sensor 4002 from magnet 4003 and defines the hinge region. The flexible hinge regions 4004 and 4005 are "living hinges," which define a bend axis as the regions flex. The bend axis is the axis about which the two links articulate. In FIG. 40B is shown a perspective view of joint 4000. The appearance of the joint 4000 is exemplary of one form and large variations may be made while retaining the function of the joint. Inside the box housing 4010 is sensor 4002 (shown with broken lines) shown as a rectangularly shaped sensor, while in housing 4011 is the magnet (shown with broken lines) shown as a cylindrically shaped magnet.

Figure 41A:
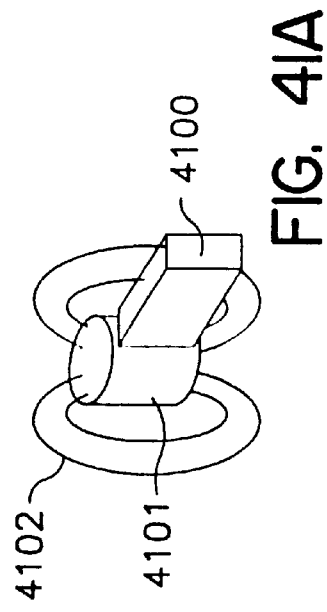
FIG. 41 is a diagrammatic illustration showing the general operation of a Hall-effect sensor with associated magnet.
Figure 41B:
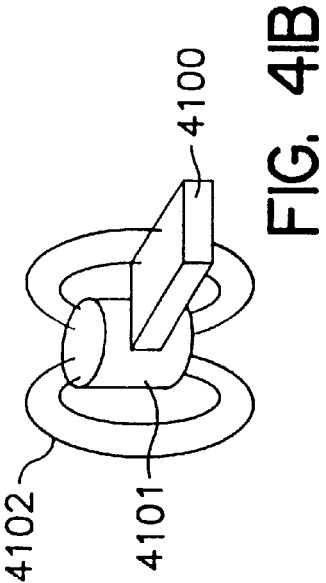

FIG. 41 presents the general operation of a Hall goniometer. In FIGS. 41A and 7B are depicted the extreme positions of the Hall sensor 4100. In FIG. 41A, sensor 4100 in an aligned configuration with the magnetic field 4102 of magnet 4101, producing minimum signal. In FIG. 41B, sensor 4100 is orthogonal to the magnetic field 4102, which provides the maximum signal. The different positions between the extreme positions measure the various angles defined by the links attached to the joint comprising the Hall sensor and magnet.

Figure 42A:
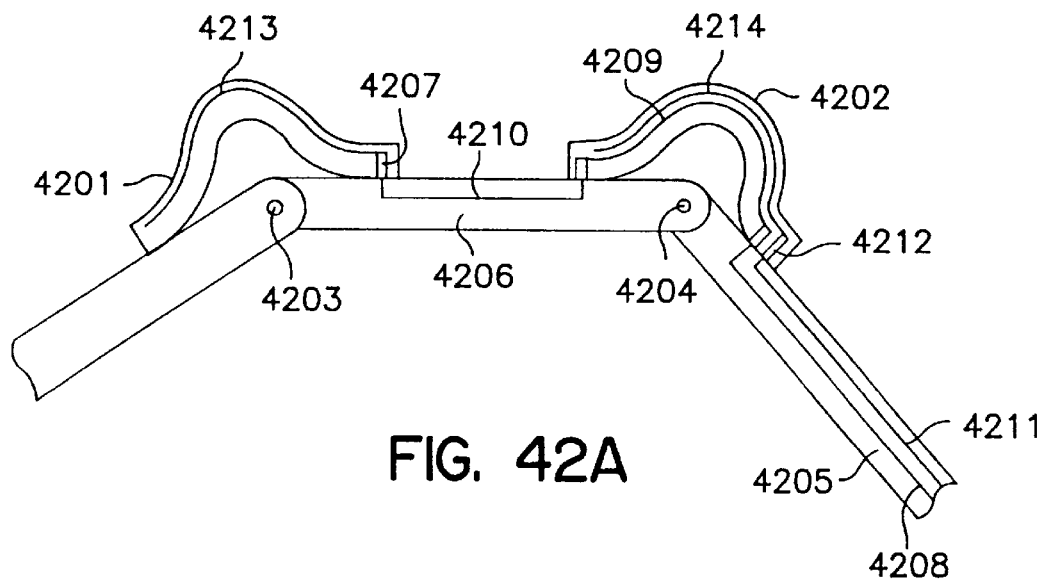
FIGS. 42A and 42B are diagrammatic illustrations showing the electrical connections for a resistive bend sensor passing through a neighboring sensor of a joint.
Figure 42B:
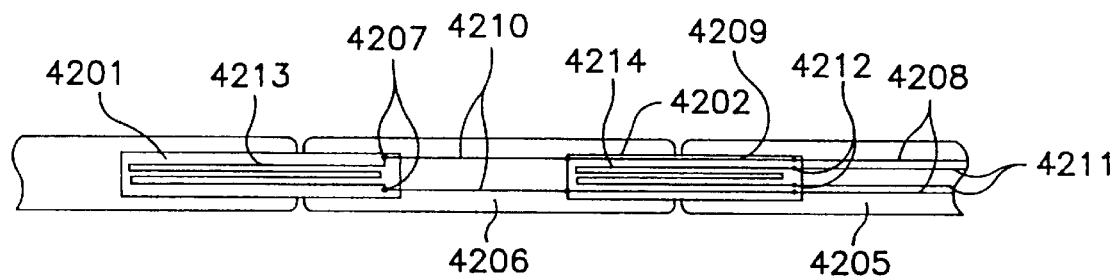

The various hinges depicted in FIGS. 37 and 39 provide that when both ends of the sensors are fixed to the links, it is possible to have the electrodes for the sensors take the form of electrical traces passing through the links. The traces for a distal joint sensor can also pass through the sensor of a joint proximal to one end of the device. This is depicted in FIGS. 42A and 42B. FIG. 42A has flex sensors 4201 and 4202 straddling joints 4203 and 4204, respectively. The electrical connections for sensor 4201 with sensing grid 4213 are incorporated into link 4205 as traces 4208, the associated non-sensing flex circuit traces 4209 pass through the neutral axis of sensor 4202, continue into link 4206 as traces 4210 and terminate at electrodes 4207 on sensor 4201. Trace 4211 is shown to terminate at electrodes 4212 on sensor 4202 which has sensing grid 4214. Although not shown, traces 4208 and 4211 lead to instrumentation circuitry. FIG. 42B shows a plan view of the device depicted in FIG. 42A with the elements corresponding thereto.

Figure 43A:
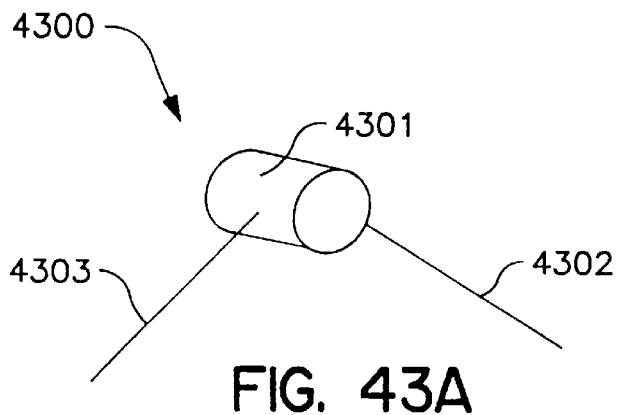
FIGS. 43A–43D are diagrammatic illustrations showing common functionality of four representations of two links adjoined by a revolute joint.
Figure 43B:
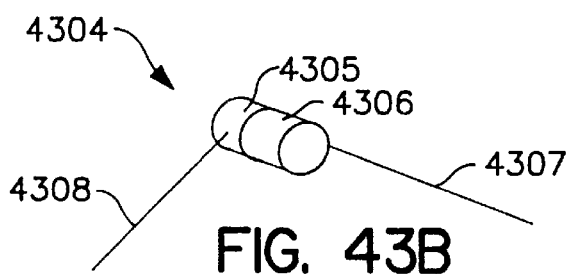
Figure 43C:
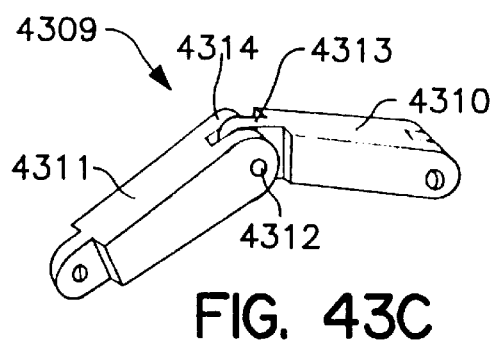
Figure 43D:
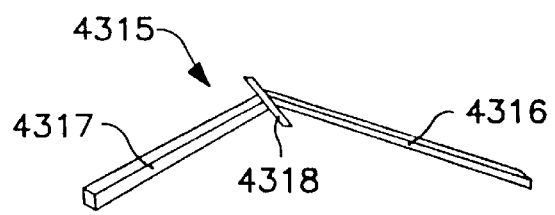

FIGS. 43A–43D provide the common functionality of four representations of two links adjoined by a revolute joint. In FIG. 43A, link-joint-link device 4300 comprises two links 4302 and 4303, represented by single line segments, connected by revolute joint 4301, represented by a cylinder. The axis of rotation of such a diagrammatical joint is parallel to the long axis of the cylinder. In FIG. 43B, link-joint-link device 4304, the joint is represented by two cylinders 4305 and 4306 which rotate relative to each other along an axis of rotation which is again parallel to the long axis of each cylinder. Joint 4308, represented by a line segment, is connected to joint portion 4305, while link 4307 is attached to joint portion 4306. In FIG. 43C, a link-joint-link device 4309 is shown, which 20. is similar to the joint structure provided in FIG. 13. Here links 4311 and 4310 rotate relative to each other about the joint axis defined by pin 4312. The implementational details of the hinge are provided by the tongue 4313 and groove 4314 structure. In FIG. 43D, link-joint-link device 4315 comprises links 4316 and 4317 which rotate relative to each other about joint axis 4318. In FIG. 43D, the axis is diagrammatically depicted only as a solid line, where the axis of rotation is coincident with the line. Any of the various joint representations may be used to explain the kinematic articulations of a structure, when the specific details of the joint construction is not critical for the explanation.

Figure 44A:
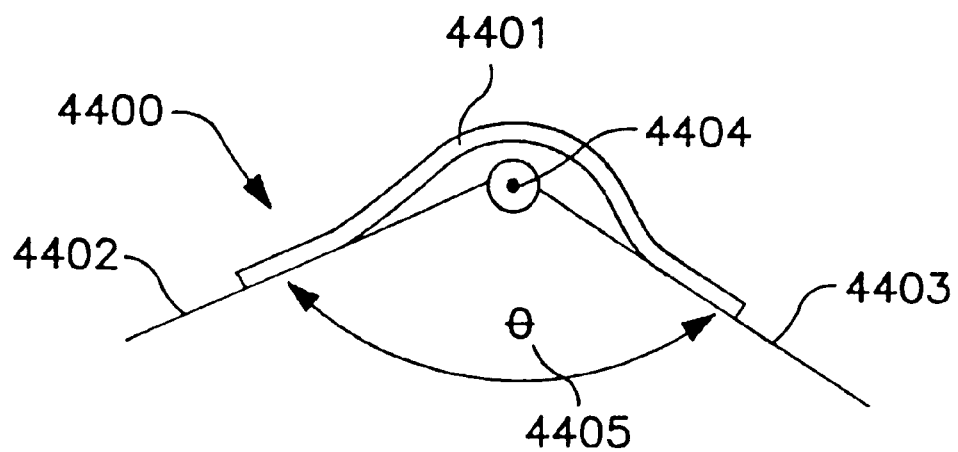
FIGS. 44 are diagrammatic illustrations showing the side views of two different joint-link structures and associated bend sensors.
Figure 44B:
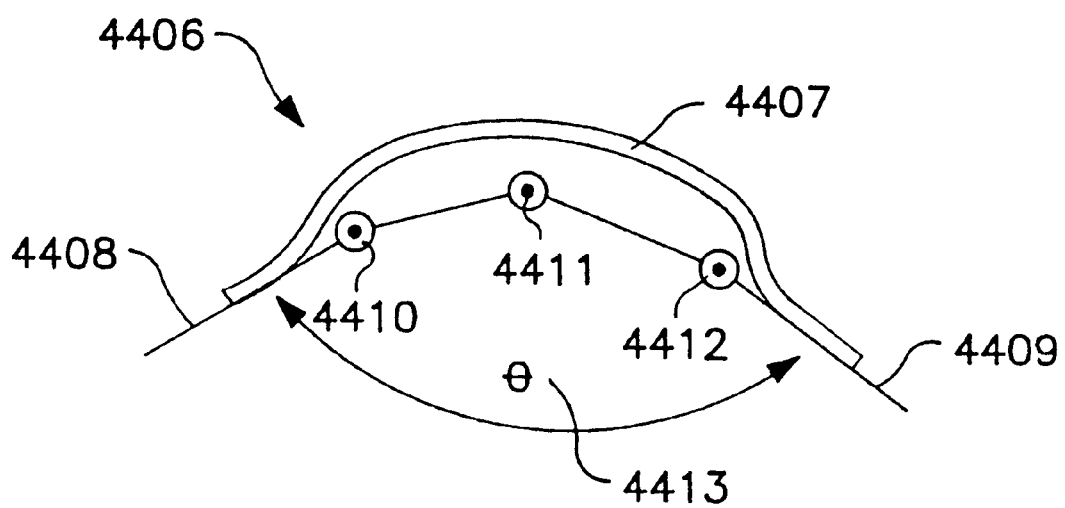

FIGS. 44A and 44B provides the side view of two different link-joint-link structures where a single sensor may be used to provide the overall joint angle. The structure 4400 in FIG. 44A employs only one joint 4404 connecting two links, 4402 and 4403, where a single resistive bend sensor 4401 is used to measure the angle 4405 between the links. The ends of the sensor are guided to lie tangent to the links, typically by directly affixing, enclosing a portion in a guiding channel or pocket, or some combination thereof. FIG. 44B presents a three-joint structure 4406, comprising joints 4410, 4411 and 4412, where the ends of resistive bend sensor 4407 are guided to lie tangent to terminal links 4408 and 4409. Due to the properties of the sensor 4407, the individual angles of joints 4410, 4411 and 4412 are unimportant, whereas the sum of the angles 4413 is what is measured by the sensor.

Figure 45A:
FIGS. 45A–45D are diagrammatic illustrations showing the comparison of a long bend sensor and a cascade of shorter sensors.
Figure 45B:
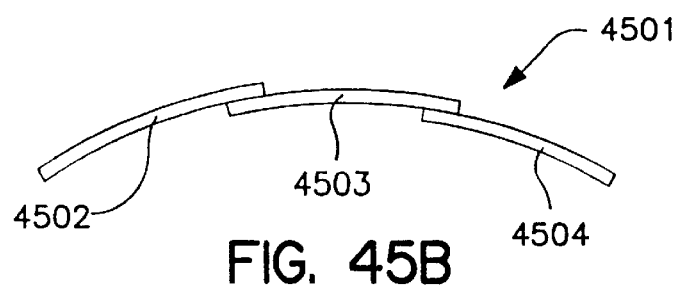

FIGS. 45A–45D disclose a "cascade sensor" and its electrical construction. FIG. 45A is the side view of a single resistive bend sensor 4500 and 4518, comprising two variable-resistance strain-sensing elements 4505 and 4506 combined back to back. In the drawing, the separation between the two elements is shown exaggerated to demonstrate the back-to-back construction. One example of a variable-resistance strain-sensing element is a strain gage, which is what is shown here, with resistive metal grid 4517 attached to plastic backing 4507. Details of a sensor such as sensor 4518 and its electrical circuitry is provided by U.S. Pat. Nos. 5,047,952 and 5,280,265, the contents of which is incorporated herein by reference. The electrical leads to sensor 4518 are wires 4508. An equivalent bend sensor to sensor 4500 is cascade sensor 4501.

Figure 45C:
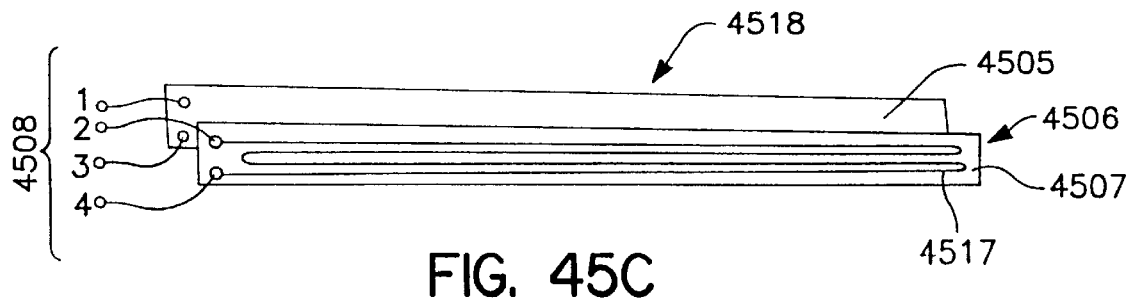
Figure 45D:
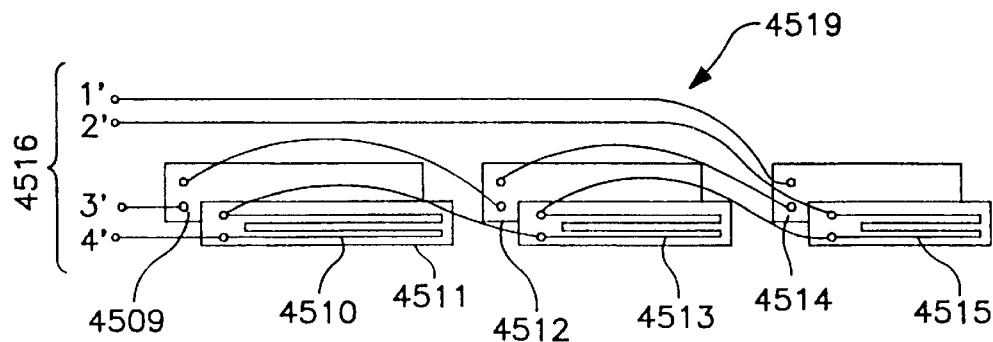

Cascade sensor 4501 comprises individual resistive bend sensors 4502, 4503 and 4504 placed such that there is minimal overlap of the sensor ends, but that the ends of the neighboring sensors have parallel tangents. In the figure, three sensors are shown, however, any convenient number of sensors may be used. Since each resistive bend sensor measures the angle between the tangents at its ends, the sum of the signals of the individual sensors of such a cascade provides the sum of the angles. The signals from each sensor may be sensed individually and then summed, or alternatively, the signals may be summed electrically by wiring the sensors as shown in FIG. 45D. When wired as shown in FIG. 45D, a cascade sensor results with the same performance and characteristics as the single long monolithic sensor 4500 and 4518 as shown in FIG. 45C. The leads 4516 of the cascaded sensor 4519 correspond to the leads 4508 of the single long sensor 4518, and may be used equivalently in an electrical circuit.

Figures 46A, 46B:
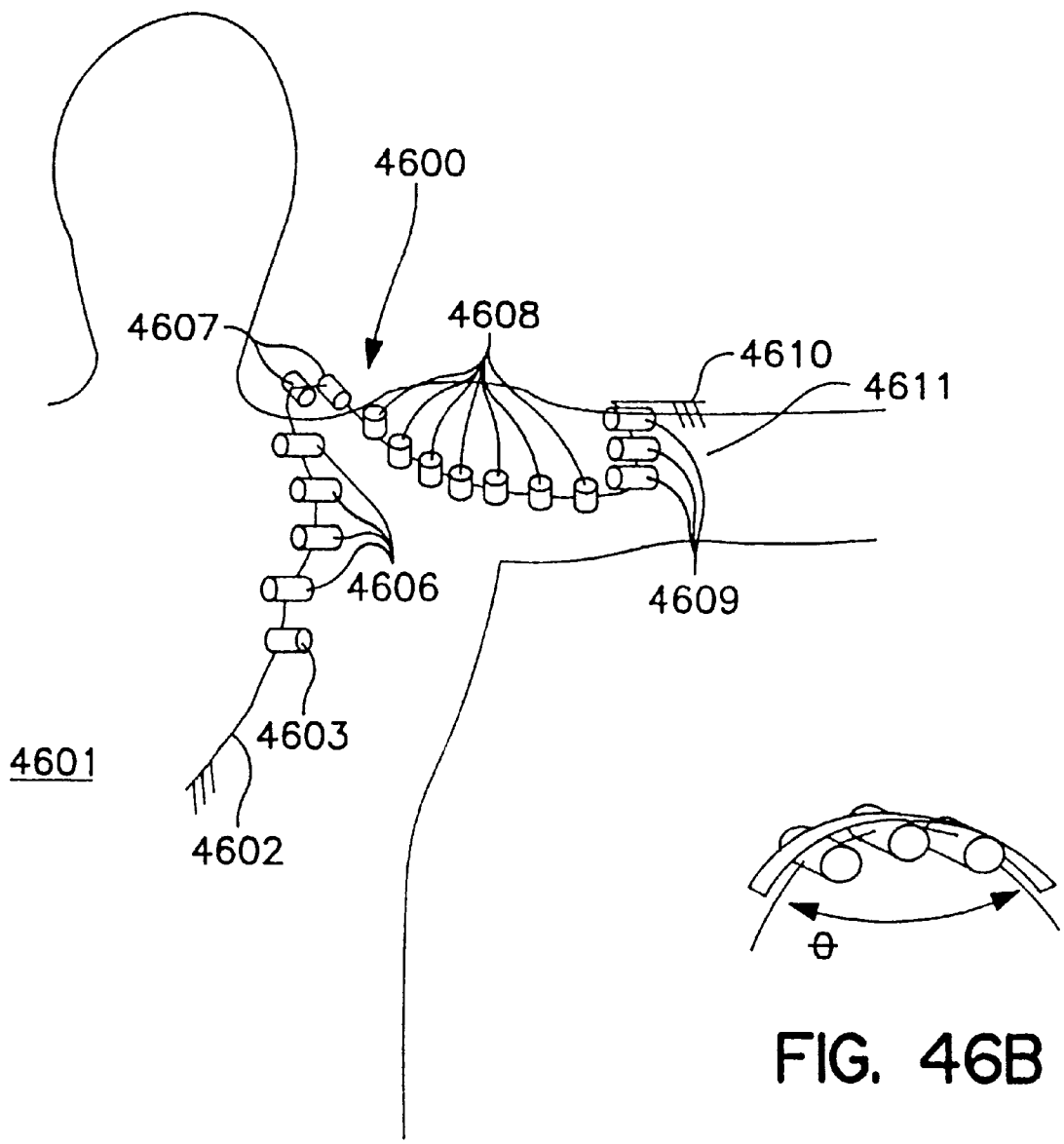
FIG. 46 is a diagrammatic illustration showing a shoulder sensor comprising many revolute joints.

FIG. 46 shows a shoulder sensor employing a long link-joint assembly 4600 comprising many joints, 4603, 4606, 4607, 4608 and 4609, with associated joint sensors. The particular kinematic arrangement of the links and joints may vary without deviating from the intended scope of this invention. A particular useful kinematic arrangement is provided here. The ends of the link-joint assembly 4602 and 4610 are secured on opposite sides of the human shoulder joint. Typically, one end of the assembly 4610 is secured to the humerus (biceps) 4611 and the other end 4602 is secured to the upper back region, near the thoracic region 4601. The method of securing is typically done by strapping the assembly end to the body, or attaching the assembly end to a portion of an elastic body covering, such as a Lycra suit. The joint angles may be sensed with resistive bend sensors, and may also be sensed using another convenient goniometer, such as a Hall-effect sensor, an optical encoder, a potentiometer, a resolver, and the like. When a set comprising multiple neighboring joints have parallel axes, and when only the angle at the ends of the set of joints is necessary, the angle may be determined using a single long sensor or a cascade sensor, such as shown in FIGS. 45A–45D. In FIG. 46, joints 4606 form such a candidate set, joints 4607 form a candidate set, joints 4608 form a candidate set and joints 4609 form a candidate set of joints, whereby a long sensor may be used.

Figure 47:
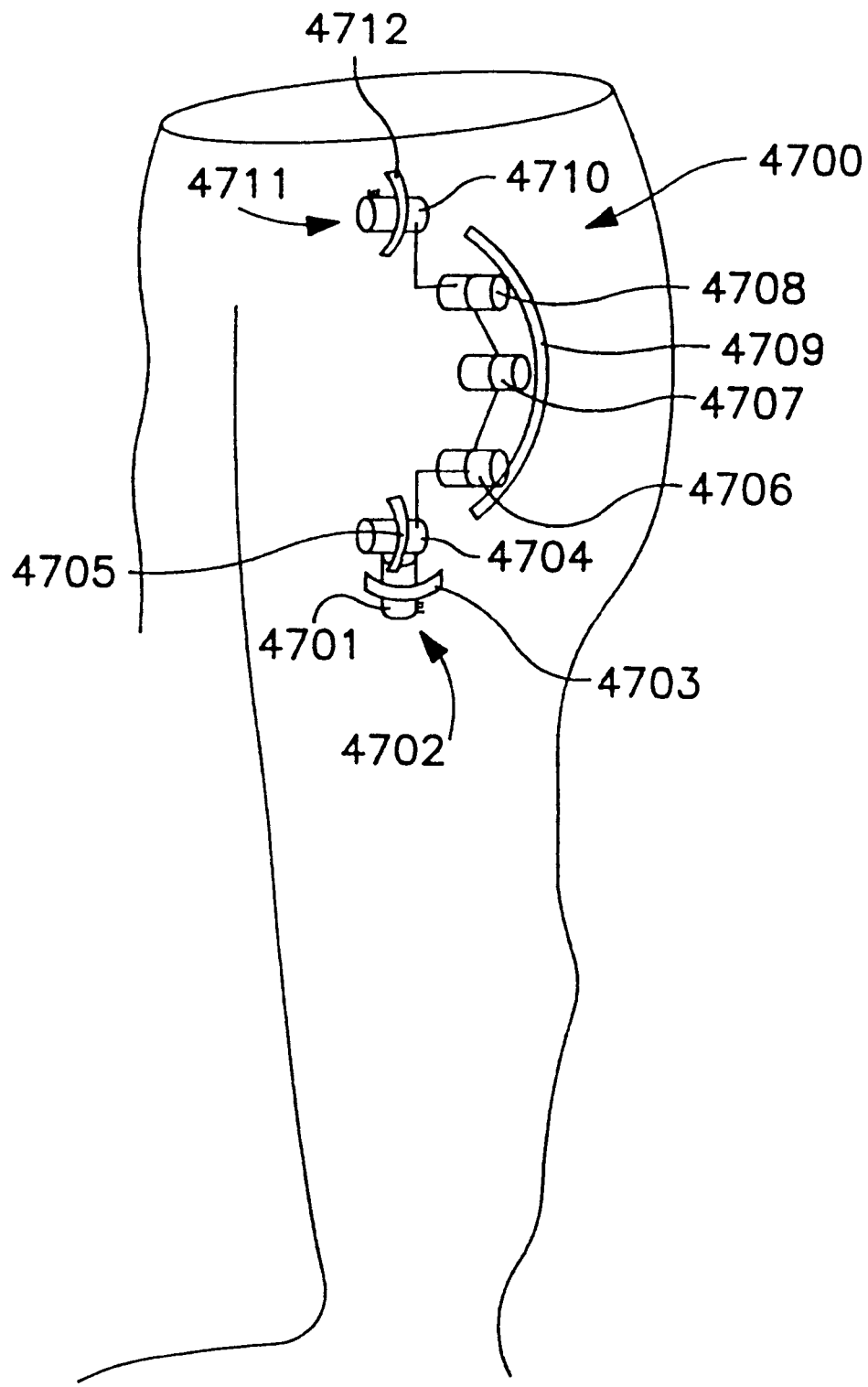
FIG. 47 is a diagrammatic illustration showing a canonical arrangement of six revolute joints, shown here measuring the hip joint.

FIG. 47 provides another useful arrangement 4700 of links and joints, to produce a canonical building block which is capable of measuring any of the three possible spatial orientations of one end of the arrangement with respect to the other end, while allowing the three spatial translations of one end relative to the other. If a single long sensor 4709 is used, the translations cannot be measured. If there is a separate goniometer, e.g., a resistive bend sensor, Hall-effect sensor, encoder, potentiometer, and the like, associated with each of the six joints, the three translations can be determined. In particular, this structure 4700 is useful since it allows relative translation of its ends using only revolute joints, since prismatic joints often have friction and can bind. There are also conveniences when only goniometers need to be used to make all measurements of a sensing device, and it can be difficult and expensive to accurately measure prismatic elongations. The canonical structure 4700 shown in FIG. 47 may use resistive bend sensors to measure the joint angles. The structure comprises one axial joint 4701, with associated sensor 4703, connected to one vertical joint 4704, with associated sensor 4705, connected to a series of three joints 4706, 4707 and 4708, with single associated sensor (or cascade sensor) 4709, further connected to joint 4710, with associated sensor 4712. The ends of this arrangement 4700 are shown attached at one end to the femur (thigh) 4702 and at the other end to the pelvis 4711.

Figure 48:
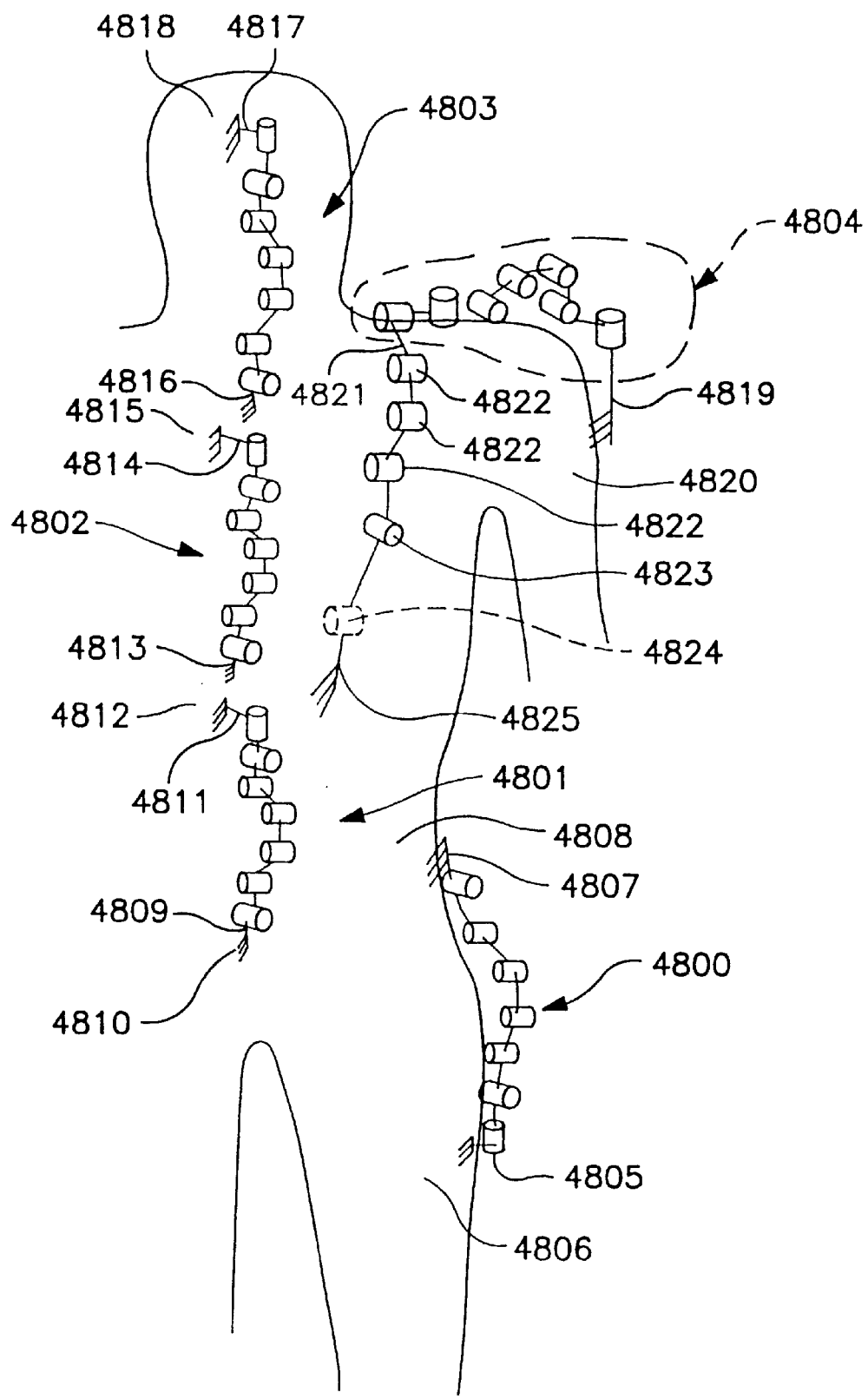
FIG. 48 is a diagrammatic illustration showing repeated application of the canonical sensing assembly of FIG. 47.

FIG. 48 shows repeated use of the canonical sensing arrangement 4700 of six joints. In FIG. 48, canonical sensor 4700 is used as sensing device 4800 to measure the hip angle, used as sensing device 4801 to measure the lumbar region of the back, used as sensing device 4802 to measure the thoracic region of the back, used as sensing device 4803 to measure the neck, and used as sensing device 4804 to measure a portion of the shoulder. Obviously, the canonical sensing assembly 4700 may be used as convenient, where only some typical regions of use are shown here. When used to measure the hip, ends 4805 and 4807 of the sensing device 4800 are secured to body portions 4806 and 4808, respectively; when used to measure the lumbar region, ends 4809 and 4811 are secured to body portions 4810 and 4812; when used to measure the thoracic region, ends 4813 and 4814 are secured to body portions 4812 and 4815; when used to measure the neck, ends 4816 and 4817 are secured to body portions 4815 and 4818.

Figure 49:
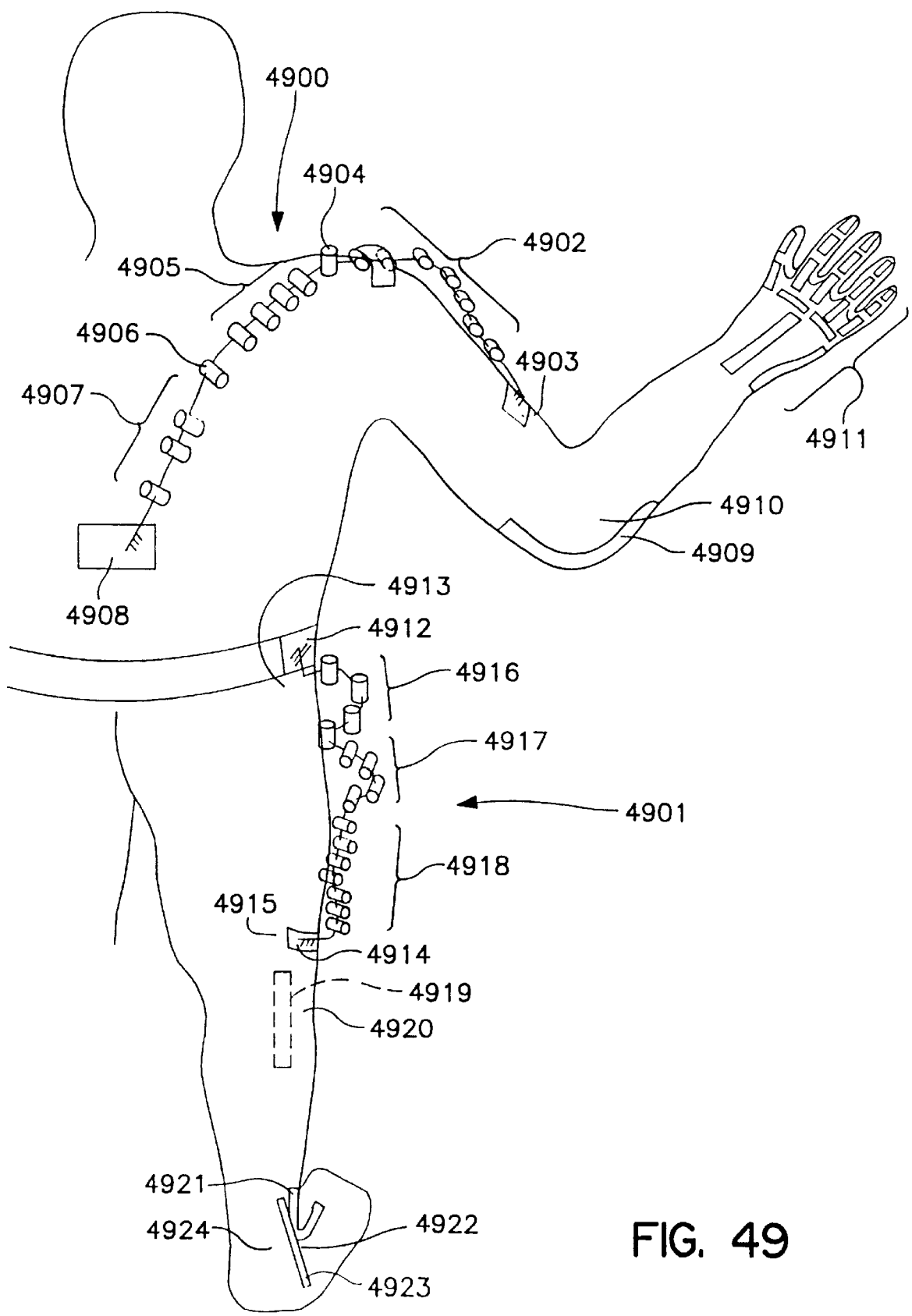
FIG. 49 is a diagrammatic illustration showing a backside view of an embodiment of a body-sensing system.

FIG. 49 provides a backside joint-link schematic view of a useful embodiment of a body sensing system. A link-joint shoulder-sensing structure 4900 is secured at its ends to support mounts 4908 and 4903 located on or near the upper back, e.g., thoracic region, and the humerus of the arm, respectively. As shown, the joints of the shoulder-sensing structure are grouped into neighboring joint sets so single long monolithic or cascaded sensors may be employed if desired. Three joints 4907 form a long-sensor-candidate joint set, which is connected to single joint 4906, which is connected to a four-joint set 4905, which is connected to a single joint 4904, which is connected to a seven-joint set 4902. The common axis orientation of joints 4907 is nominally in the plane of the back, the axis of joint 4906 is nominally perpendicular to the back; the common axis orientation of joints 4905 is nominally in the plane of the back, the axis of rotation for joint 4904 is along the long axis of the body; and the common axis orientation for joint 4902 is in the plane of the humerus and forearm when the elbow is flexed.

The link-joint device 4901 for measuring the hip is attached to mount 4914 and mount 4912 which are secured to the thigh and pelvis regions of the body, respectively. The device 4901 comprises joint set 4918, with common axis normal to the plane of the thigh and calve when the knee is bent; joint set 4917, with common axis lying nominally in the plane of the thigh and calve; and joint set 4916, with common axis nominally parallel to the long axis of the femur.

Devices 4900 and 4901 allow unrestricted range of motion of the associated body joint. When long or cascaded sensors are used to measure the angle of a joint set, only orientation of the associated limb can be determined. Using knowledge of the kinematics of the human body, and using inverse kinematic mathematical techniques, the joint angles of the body joints can be resolved.

FIG. 49 shows the use of single degree-of-freedom resistive bend sensors to measure single degree-of-freedom joints, such as the elbow 4910 with sensor 4909, knee 4920 with bend sensor 4919 and ankle 4924 with sensor 4921 on the instep 4922 and with sensor 4923 on the side of the ankle. It is also convenient to use the single-axis bend sensors to measure the angles of the joints of the hand. A CyberGlove by Virtual Technologies, Inc. of Palo Alto, Calif. provides such sensing means in an elastic glove.

Figure 50A:
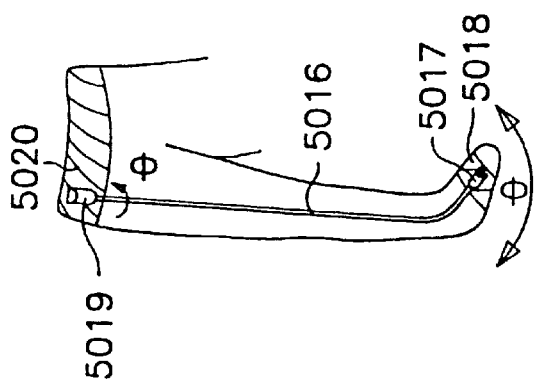
FIGS. 50A–50D are diagrammatic illustrations showing a flexible device for measuring axial rotation.
Figure 50B:
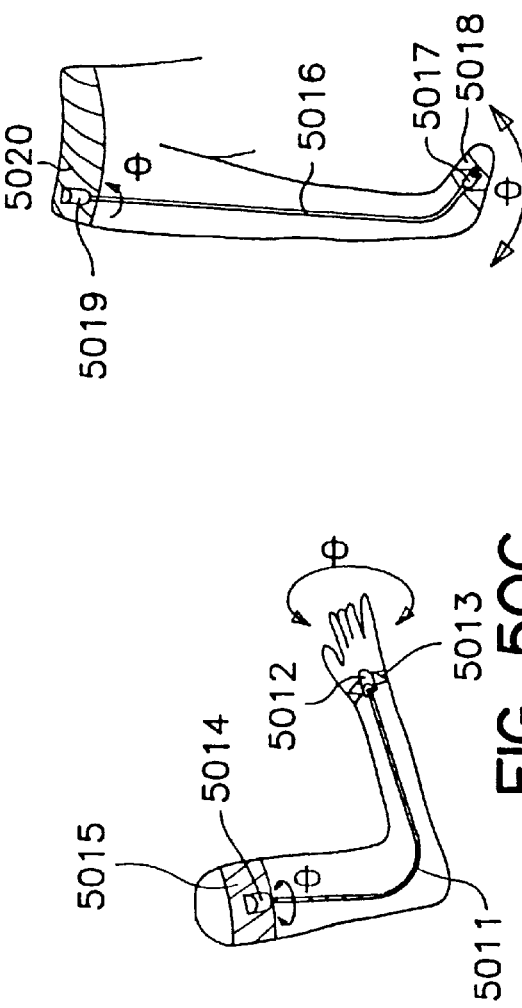
Figure 50C:
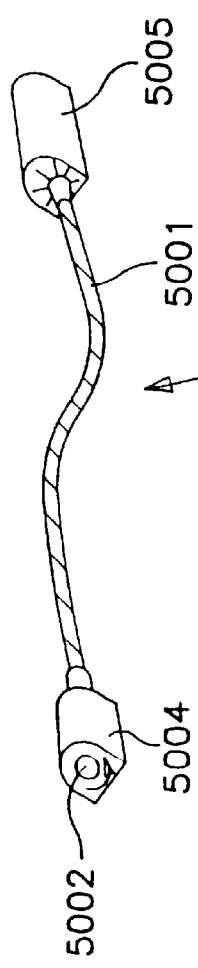
Figure 50D:
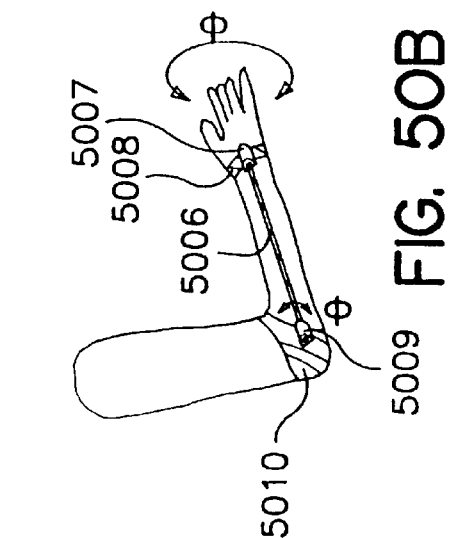

FIGS. 50A–50D provide a device 5000 for measuring axial rotation of a human body part such as the forearm (FIGS. 50B and 50C), waist, head and leg (FIG. 50D). Device 5000 comprises a flexible transmission cable or flexible shaft 5001 which is flexible in bending, but stiff in torsion. That is, it is able to transmit torsion. Such cables are often used for flexible couplings and drive shafts, such as may be used for radio-controlled boats. One end 5005 of cable 5001 is attached to a first body part, while the other end of the cable rotates relative to housing 5002, which is secured on a second body part which is capable of rotating relative to the first body part. A goniometer is associated with housing 5002 which can determine the rotation of the cable. Typical goniometers include resistive bend sensors, Hall-effect sensors, optical encoders, potentiometers, resolvers, and the like. Since the cable is flexible, it is comfortable and can bend around joints which are not intended to affect the rotation of the cable, while still measuring the rotation of a body part due to the axial transmission of the rotation via the cable.

As shown in FIG. 50B, one end 5007 of the cable 5006 is secured to the wrist of an arm by strap 5008, while the other end 5009 of the cable is attached to the arm, for instance near the elbow, by strap 5010. Either end 5007 or 5009 may include the goniometer. If the goniometer adds weight or bulk to the end of the cable, that end is typically placed nearer the torso for better support and to reduce the effect of inertia. FIG. 50C shows another nearer useful embodiment where one end 5014 of the cable 5011 is attached via strap 5015 to the humerus. The other end 5012 is again attached near the wrist with strap 5013. FIG. 50D shows a useful embodiment where one end 5017 of cable 5016 is attached by strap 5018 to the foot, and the other end 5019 is attached to the waist by securing means 5020. As mentioned above, either end may contain a goniometer for measuring the rotation of the cable. If preferred, a goniometer may be employed in both ends of the cable structure.

This flexible-cable sensing technique allows sensing of relative rotation (nominally axial to the cable or flexible shaft) between two body links that can also articulate relative to each other about an axis other than the cable axis. The flexible-cable sensor 5000 may be used to measure rotation of inanimate machines or objects, and animate bodies other than human bodies.

Figure 51:
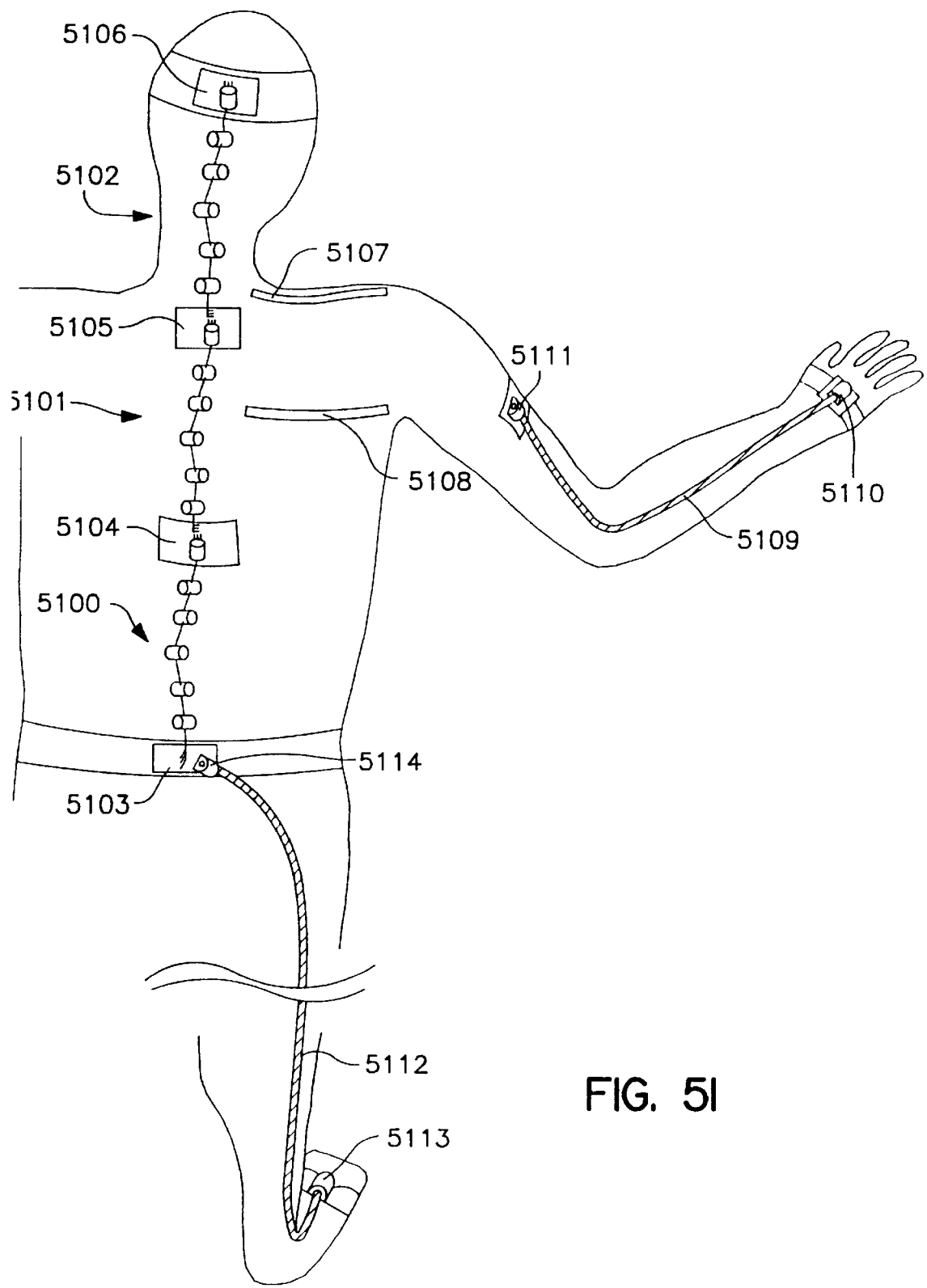
FIG. 51 is a diagrammatic illustration showing the use of the flexible axial rotation sensor to measure the rotation of the forearm and leg.

FIG. 51 is similar to FIG. 48, but is also shows the use of the flexible-cable sensor for measuring the forearm rotation and the leg rotation. Cable 5109 is connected by ends 5111 and 5110 to the humerus and wrist regions, respectively; cable 5112 is connected by ends 5113 and 5114 to the foot and pelvis, respectively; canonical six-joint sensing assembly 5100 is connected at its ends to securing mount 5103 and 5104; assembly 5101 is connected to mount 5104 and 5105; assembly 5102 is connected to mount 5105 and 5106. Flat, flexible resistive bend sensors 5107 and 5108 are placed in functional relation to the shoulder to measure the sternoclavicular elevation (pitch) and azimuth (yaw), respectively. Such a sensing assembly can measure the movement of the lumbar, thoracic and neck regions of the back, the shoulder and hip movements and the forearm and leg rotations. Obviously, other sensors may be conveniently used to measure other desired degrees of freedom of the human body.

Figure 52:
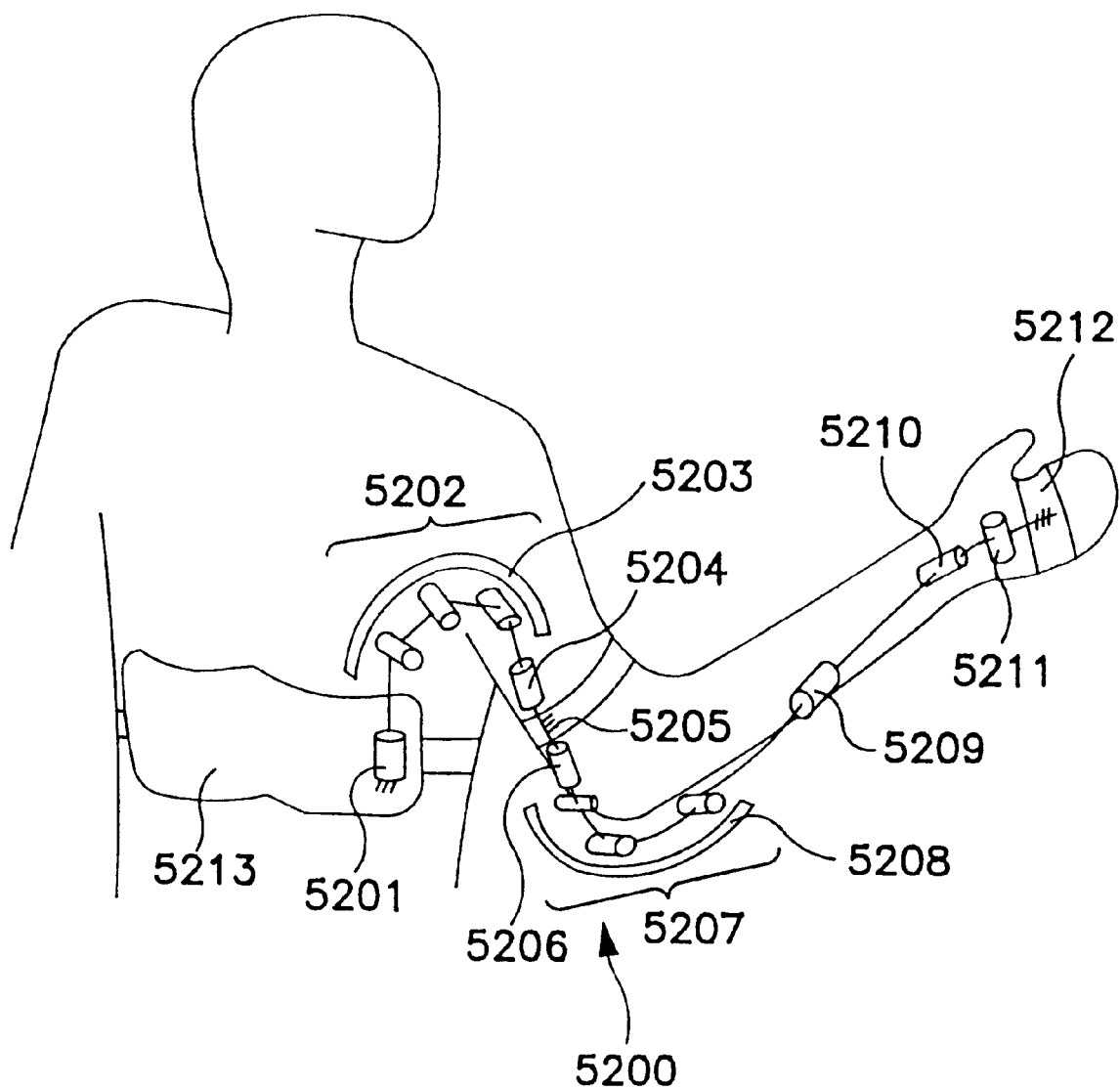
FIG. 52 is a diagrammatic illustration showing another embodiment for measuring forearm rotation.

FIG. 52 provides another way to measure the rotation of the forearm using axial revolute joint 5209 as part of assembly 5200. Here joint 5201 is secured to mount 5213 which is secured to the torso, typically by straps or elastic material. Joint set 5202, measured by resistive bend sensor 5203 is connected to joint 5201 and to axial joint 5204. Joint 5204 is secured at location 5205, which is further connected to axial joint 5206. Joint 5206 is connected to joint set 5207 and sensed by sensor 5208. Set 5207 is connected to axial revolute joint 5209 which is connected to wrist abduction joint 5210 which is connected to wrist flexion joint 5211 which is terminated on the hand region by securing means 5212. As such, the axial rotation of the forearm is measured by axial joint 5209. Various modification may be made to the kinematic structure of this mechanism without departing from the intended scope of the subject invention.

Figure 53B:
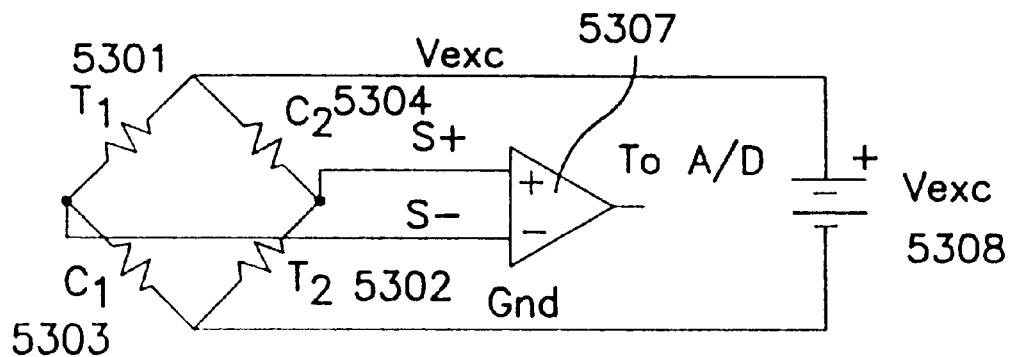
FIG. 53 is a diagrammatic illustration showing the construction of a resistive bend sensor comprising four resistive strain-sensing element.
Figure 53A:
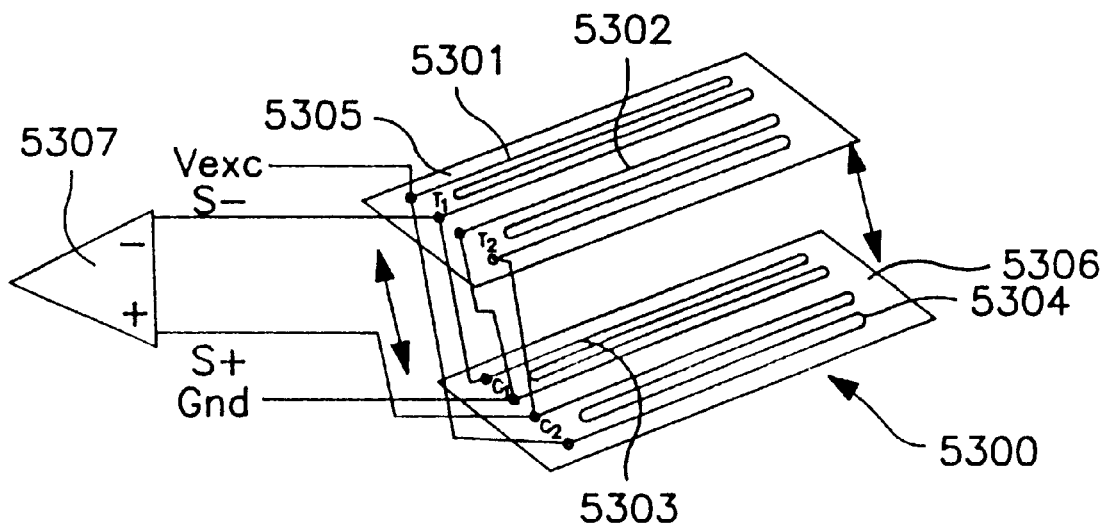

FIG. 53A shows the construction of a resistive bend sensor 5300 comprising four variable resistance sensing elements, such as a strain gage. The elements 5301 and 5301 are located on one side of flexible, incompressible backing 5305, while elements 5303 and 5304 are located on the other side of backing 5306, where both sides are combined back to back, typically by adhering or monolithic construction, the resulting sensor provides in a single unit, all elements necessary for a fully-balanced Wheatstone bridge circuit. Thus, the sensor is very insensitive to temperature fluctuations, electrical noise, changes in the mechanical properties of the materials, and the like. The sensor assembly also doubles the sensing signal over the case when only a single sensing element on each backing is used, and a constant-resistance reference half-bridge is employed. In FIG. 53A, the two sides of the sensor are shown apart so the construction of the sensor can be more easily demonstrated. The "top" and "bottom" element grids may have solder tabs or though-holes aligned to make lead conductor attachment more convenient, e.g., where a single soldering step is needed. FIG. 53B provides the electrical connections of the sensing elements in a Wheatstone circuit, where differential amplifier 5307 provides an analog output proportional to the angle between the tangents at the ends of the sensor 5300. The bridge circuit has excitation voltage 5308.

Figure 54A:
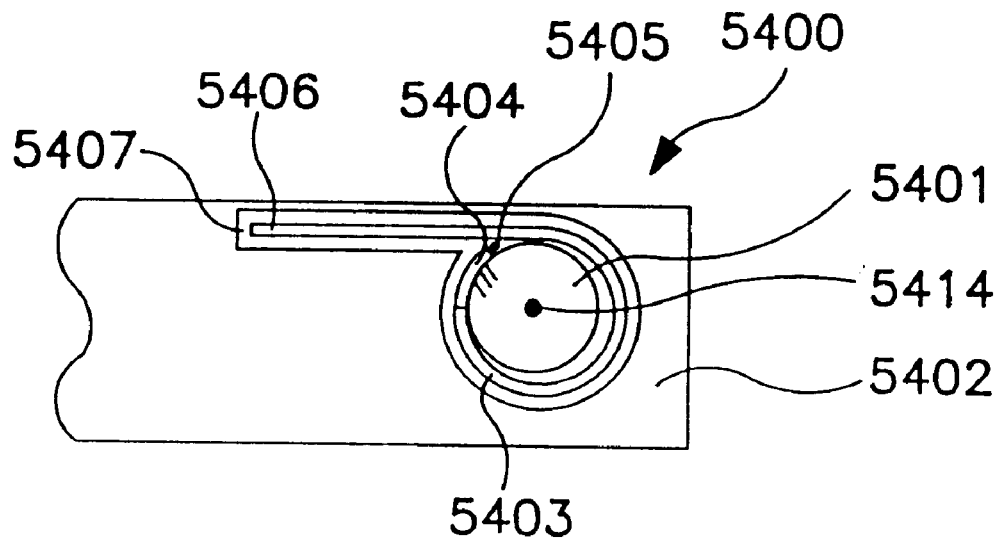
FIGS. 54A and 54B are diagrammatic illustrations showing two axial sensors.
Figure 54B:
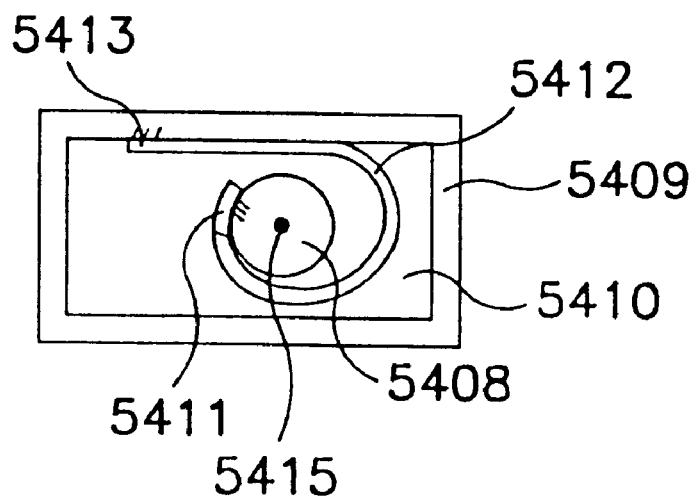

FIGS. 54A and 54B provide an axial sensors constructed using a flexible resistive strain-sensing bend sensor. Axial sensor 5400 comprises rotary portion 5401 which rotates about axis 5414 relative to housing 5402. Bend sensor 5403 is connected at end 5404 to rotary portion 5401, where sensor end 5406 is free to slide in guiding channel 5407. Sensor wires 5405 may exit the assembly in any convenient manner, such as along the direction of axis 5414. Since the bend sensor measures the angle between the tangents at its ends, as rotary portion 5401 rotates relative to housing 5402, the sensor signal changes proportionally.

FIG. 54B provides another embodiment to provide axial measurement. Rotary component 5408 rotates relative to housing 5409 about axis 5415. End 5411 of resistive bend sensor 5412 is affixed to rotary component 5408, while end 5413 is affixed to housing 5410. The amount of "slack" in the sensor determines how many degrees of rotation can be sensed.

Figure 55:
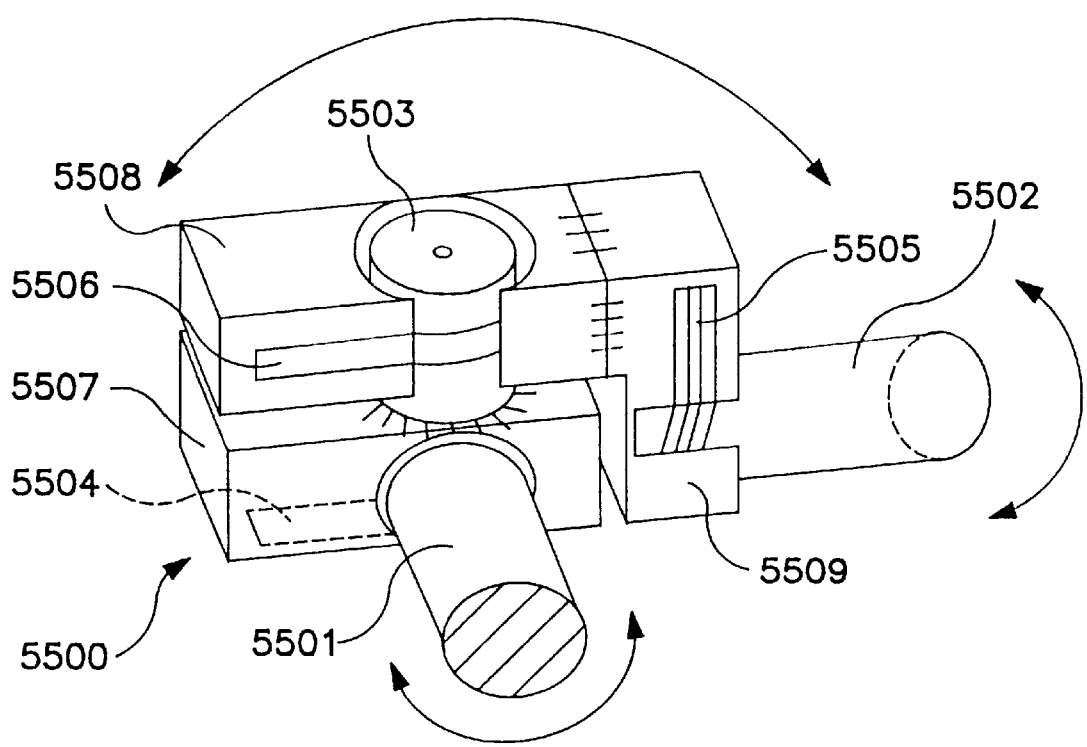
FIG. 55 is a diagrammatic illustration showing a "ball joint" sensor.

FIG. 55 provides an embodiment 5500 whereby three degrees of freedom of orientation between two links 5501 and 5502 can be measured. Link 5501 rotates relative to housing 5507, where sensor 5504, shown on the bottom surface, measures the rotary angle. Cylinder 5503 is attached to housing 5507 and rotates relative to housing 5508, where sensor 5506 measures the angle of rotation. Housing 5508 is attached to housing 5509 relative to which link 5502 rotates, which rotation is measured by sensor 5505. This structure is shown as such to provide a functional description of how to create a 3-degree-of-freedom orientation sensor from rotary joints, and where the axes of the rotary joints all converge at a single point, i.e., a "ball joint" is effectively created. Modifications may be made to this design as convenient.

Figure 56:
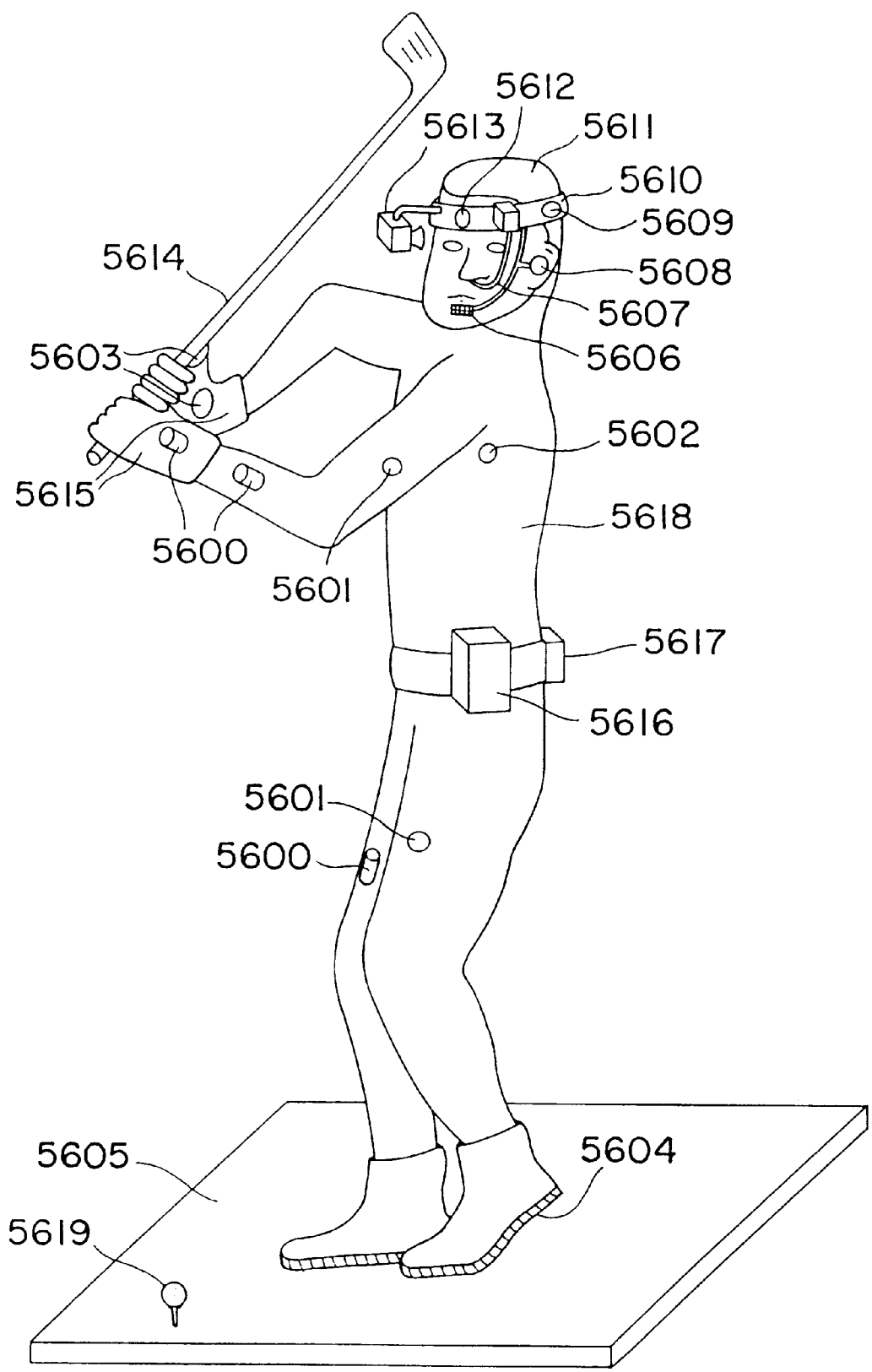
FIG. 56 is a diagrammatic illustration showing a sensing system which senses body functions and provides feedback.

FIG. 56 shows a variety of body-function sensing and feedback devices that may be used with a body-sensing apparatus 5618 as provided by the subject invention. In particular, a useful feedback device is a vibro-tactile element 5600, similar to a pager motor, which may be placed at any convenient location about the body and programmed to a desirable frequency of vibration by a control program. A useful body-function-sensing element is an EMG 5601 sensor, so muscle electrical activity may be correlated to resulting joint motion. Another useful parameter to be measured is ground reaction force as measured optionally by force/presure pads 5604 on the bottom of a foot. Other sensing and feedback elements associated with the apparatus 5618 include a force/pressure-sensing platform 5605, a data-logging communication module and local computer 5616, a body-position and orientation sensor 5617 (e.g., inertial or electromagnetic, optical or ultrasonic), EKG sensor 5602, microphone 5606, respiration sensor 5607, earphone 5608, EEG sensor 5609 attached to headband 5610 or to hood 5611 of suit, EOG sensor 5612, eye tracker and/or facial expression monitor 5613 and forcelpressure/contact sensors 5603 on hands. Other elements included in the figure include a golf ball 5619, golf club 5614 and instrumented glove 5615, such as a CyberGlove. Such a body-sensing and feedback suit finds utility in sports analysis, virtual reality, motion capture, biomechanics, and the like.

FIGS. 57A–57C add angle sensors and plates to the axial rotation sensor of FIG. 50. Plates 5704 and 5705, which are flexible about their minimum-moment-of-inertia axis, and resistant to bending about the other two axes, are affixed to the flexible transmission cable 5701. The cable has ends 5702 and 5703, at least one of which has a goniometer to measure the relative rotation of the ends of the cable. As shown in FIG. 57C, each plate 5710 is affixed only at one end 5711 to the cable 5709, whereas the other end of the plate is allowed to slide relative to the cable, typically by employing cable loops 5712. The plates act to protect the flexible resistive bend sensors associated with each plate. Each plate has a guiding means associated with it to guide the associated sensor. FIG. 57B shows a simplified discrete link-joint structure model of the cable sensor of FIG. 57A, where the sensors and plates are positioned alternating at 90 degrees to each other. To calculate the orientation of the endpoints 5702 and 5703 of the cable, it is typically assumed that the cable flexes with a constant arc over the region of each bend sensor. For this configuration, each bend sensor should be sensed independently of the others. All sensors along the cable, may, however, be attached to its neighbor on a flexible circuit substrate, such as is provided in FIGS. 42A and 42B.

FIGS. 58A–58C provide various specialty joint-sensing devices. FIG. 58A provides a knee-angle monitor 5800 comprising body mounting strap 5801, which may be a commercial elastic knee brace, a resistive bend sensor 5802 in a guide on strap 5801 which holds the ends of the sensor tangent to the thigh and shin. A monitor 5803 may be attached to device 5800, or may be located in convenient proximity thereto, or mounted near the waist in a larger monitor pack 5804. The monitor may calculate the joint angle and may perform various functions such as via an LCD screen or voice synthesizer it may inform the wearer of various states of their joint. The monitor may have LEDs to provide information, and may provide such joint information and functions as average angle, minimum and maximum angles, reset, start/stop data acquisition, repetition rate, and the like. In a rehabilitation function, the monitor may request that the wearer perform range-of-motion exercises and encourage improved performance based on desired movements. The monitor may also warn the wearer if an acceptable joint ranges were being exceeded, for instance using a tone or buzz. An ankle monitoring device 5805 is also shown in FIG. 58A, where ankle strap 5807 comprises a sensor guide to guide sensor 5806 to measure the angle of flexion of the ankle. The ankle strap may be similar to a commercial ankle brace. The knee and ankle monitoring systems may be used independently or together, or with other joint sensing devices.

FIG. 58B provides an elbow-sensing device 5808, similar in nature to the knee and ankle-sensing devices of FIG. 58A. Elbow-sensing device 5808 comprises an elbow strap 5810 with a sensor guide to guide the resistive bend sensor 5809 over the elbow joint, keeping the tangents at the ends of the sensor tangent to the humerus and forearm. A monitor 5811 may also be used. FIG. 58C provides a wrist-sensing device 5812 comprising two wrist sensors 5813 for measuring wrist flexion and abduction. The sensors are guided along the wrist by guides in hand strap 5814. A monitor 5815 may be used similarly to the previous specialty joint sensors.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An apparatus for measuring the relative position of two terminal links, said apparatus comprising:
    a kinematic structure comprising a plurality of device links having terminal links and connected by at least two device revolute joints;
    at least one bend sensor extending over at least one of said device revolute joints, said bend sensor generating an electrical signal;
    a mount to mount said apparatus so that it is capable of moving in relation to a body part; and
    a circuit receiving the electrical signal from said bend sensor and generating a sensed signal,
    whereby a signal processor may receive said sensed signal and generate an output signal indicative of the relative position of portions of said kinematic structure.

2. The apparatus in claim 1, further comprising said signal processor and wherein said signal processor generates said output signal using forward kinematics.

3. The apparatus in claim 1, wherein the mount comprises an elastic garment comprising one or more pockets.

4. The apparatus in claim 3, wherein the mount further comprises one or more mounting plates receivable in the pockets.

5. The apparatus in claim 1, wherein the mount comprises a mounting plate attachable to the body part.

6. The apparatus in claim 1, further comprising means for determining the relative orientation of portions of the kinematic structure.

7. The apparatus in claim 1, wherein the bend sensor is a resistive bend sensor.

8. The apparatus in claim 1, wherein the mount is adapted to mount the apparatus on a body part.

9. The apparatus in claim 1, further comprising a holder attaching said sensor in functional juxtaposition to said kinematic structure.

10. The apparatus in claim 1, further comprising means for measuring one or more of muscle electrical activity of the body, ground reaction forces of the body, heart electrical activity of the body, sound, respiration of the body, and brain electrical activity of the body.

11. The apparatus in claim 10, further comprising means for providing feedback to the body.

12. The apparatus in claim 11, wherein the means for providing feedback to the body comprises means for providing vibro-tactile feedback to the body.

13. The apparatus in claim 1, further comprising means for providing feedback to the body.

14. The apparatus in claim 13, wherein the means for providing feedback to the body comprises means for providing vibro-tactile feedback to the body.

15. The apparatus in claim 1, wherein the bend sensor is a resistive bend sensor comprising four variable resistance sensing elements wherein each sensing element is a leg of a wheatstone bridge circuit.

16. The apparatus in claim 1, further comprising a second bend sensor extending over a second device revolute joint.

17. The apparatus in claim 1, wherein the at least one bend sensor extends over at least two device revolute joints.

18. An apparatus for measuring the relative position of body parts of a human body, the apparatus comprising:
    a garment adapted to be worn on the human body;
    a kinematic structure in or on the garment, the kinematic structure extendable across a joint of the human body, the kinematic structure comprising a plurality of links having terminal links connected by at least two revolute joints; and
    a sensing device capable of generating a signal related to the relative position of the terminal links,
    whereby a signal processor may receive the signal and generate an output signal indicative of the relative position of body parts of the human body.

19. The apparatus in claim 18, wherein the sensing device comprises a resistive bend sensor.

20. The apparatus in claim 18, wherein the sensing device comprises a Hall effect sensor.

21. An apparatus for measuring the relative position of body parts of a human body, the apparatus comprising:
    a garment adapted to be worn on the human body to at least partially cover a first joint and a second joint;
    one or more first sensors positionable in or on the garment and capable of generating a signal related to the movement of the first joint in at least one degree of freedom;
    a kinematic structure in or on the garment, the kinematic structure extendable across the second joint and comprising terminal links connected to one another so as to be relatively moveable in at least two degrees of freedom; and
    one or more second sensors capable of generating a signal related to the movement of the terminal links in the at least two degrees of freedom.

22. The apparatus in claim 21, wherein the first or second sensors comprise a resistive bend sensor.

23. The apparatus in claim 21, wherein the first joint comprises one or more of an elbow and a knee, and the second joint comprises one or more of a shoulder, a hip, an ankle, a wrist, and a portion of a spine.

* * * * *